US007179957B1

(12) United States Patent
Zhao et al.

(10) Patent No.: US 7,179,957 B1
(45) Date of Patent: Feb. 20, 2007

(54) METHOD FOR ALTERING NITROGEN OR OIL CONTENT OF SEEDS BY DOWN REGULATING AGL11 EXPRESSION OR ACTIVITY

(75) Inventors: Jianmin Zhao, St. Louis, MO (US); Scott E. Andersen, St. Louis, MO (US); Wenpei Su, San Diego, CA (US); Shiping Wang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/842,653

(22) Filed: May 10, 2004

Related U.S. Application Data

(60) Provisional application No. 60/469,297, filed on May 9, 2003.

(51) Int. Cl.
  *C12N 15/82* (2006.01)
  *C12N 15/87* (2006.01)
  *C12N 15/90* (2006.01)
(52) U.S. Cl. .................. 800/285; 800/281; 800/286
(58) Field of Classification Search ............... 536/23.1; 800/295, 278, 285, 286; 435/320.1
See application file for complete search history.

(56) References Cited

U.S. PATENT DOCUMENTS

| 6,198,024 | B1 | 3/2001 | Yanofsky et al. | ............ 800/287 |
| 6,288,305 | B1 | 9/2001 | Yanofsky et al. | ............ 800/290 |
| 6,410,826 | B1 | 6/2002 | Yanofsky et al. | ............ 800/278 |
| 6,768,042 | B2 | 7/2004 | Yanofsky et al. | ............ 800/290 |
| 6,781,036 | B2 | 8/2004 | Yanofsky et al. | ............ 800/290 |
| 6,841,721 | B2 | 1/2005 | Yanofsky et al. | ............ 800/290 |
| 6,846,677 | B2 | 1/2005 | Yanofsky et al. | ............ 435/468 |

FOREIGN PATENT DOCUMENTS

WO   WO99/00503   *   1/1999

OTHER PUBLICATIONS

Rounsley et al . The Plant Cell. 1995. vol. 7. pp. 1259-1269.*
Mette et al., EMBO J., 2000, vol. 19, pp. 5194-5201.*
Mette et al., EMBO J., 1999, vol. 18, pp. 241-248.*
Fan et al., "Specific Interactions Between the K Domains of AG and AGLs, Members of the MADS Domain Family of DNA Binding Proteins", The Plant Journal, 12(5):999-1010 (1997).
Flanagan et al., "Specific Expression of the AGL1 MADS-box Gene Suggests Regulatory Functions in *Arabidopsis* Gynoecium and Ovule Development", The Plant Journal, 10(2):343-353 (1996).
Gu et al., "The Fruitfull MADS-box Gene Mediates Cell Differentiation During *Arabidopsis* Fruit Development", development, 125:1509-1517 (1998).
Heck et al., "AGL15, a MADS Domain Protein Expressed in Developing Embryos", The Plant Cell, 7:1271-1282 (1995).
Ma et al., "AGL1-AGL6, An *Arabidopsis* Gene Family With Similarity to Floral Homeotic and Transcription Factor Genes", Genes & Development, 5:484-495 (1991).
Mandel et al., "The *Arabidopsis* AGL8 MADS Box Gene is Expressed in Inflorescence Meristems and is Negatively Regulated by APETALA1", The Plant Cell, 7:1763-1771 (1995).
Mizukami et al., "Functional Domains of the Floral Regulator AGAMOUS: Characterization of the DNA Binding Domain and Analysis Negative Mutations", The Plant Cell, 8:831-845 (1996).
Purugganan et al., "Molecular Evolution of Flower Development: Diversification of the Plant MADS-Box Regulatory Gene Family", Genetics, 140:345-356 (1995).
Rounsley et al., "Diverse Roles for MADS Box Genes in *Arabidopsis* Development", The Plant Cell, 7:1259-1269 (1995).
Savidge et al., "Temporal Relationship Between the Transcription of Two *Arabidopsis* MADS Box Genes and the Floral Organ Identity Genes", The Plant Cell, 7:721-733 (1995).
Theiben et al., "Structural Characterization, Chromosomal Localization and Phylogenetic Evaluation of Two Pairs of AGAMOUS-like MADS-box Genes From Maize", Gene, 156:155-166 (1995).
Yanofsky et al., "The Protein Encoded by the *Arabidopsis* Homeotic Gene Agamous Resembles Transcription Factors", Nature, 346:35-39 (1990).
Yanofsky et al., "Floral Meristems to Floral Organs: Genes Controlling Early Events in *Arabidopsis* Flower Development", Annual Rev. Plant Physiol. Plant Mol. Biol., 46:167-188 (1995).

* cited by examiner

*Primary Examiner*—Ashwin Mehta
(74) *Attorney, Agent, or Firm*—Fulbright & Jaworski L.L.P.

(57) ABSTRACT

The present invention relates to the genetic manipulation of the expression of the AGL11 gene and homologs thereof in order to alter protein or oil levels in a seed of a crop plant. The downregulation of AGL11 is associated with an increase in protein concentration in the plant seed. Conversely, upregulating the AGL11 gene is associated with an increase in oil concentration in the plant seed.

6 Claims, 25 Drawing Sheets

METHOD FOR ALTERING NITROGEN OR OIL CONTENT OF SEEDS BY DOWN REGULATING AGL11 EXPRESSION OR ACTIVITY

This application claims the benefit of U.S. Provisional Application No. 60/469,297, filed May 9, 2003, incorporated herein by reference.

The present invention is in the field of plant genetics and biochemistry. More specifically, the present invention relates to methods of modulating various nutrients in plants, including, for example, protein or oil.

Tillable land available for production of food crops continues to diminish because each year more acreage is devoted to alternative uses. At the same time, the human population is rapidly increasing, predicted to reach 10 billion by the year 2050. Therefore, it is essential to increase agricultural productivity to meet the nutritional needs of the world's burgeoning population. Agricultural productivity may be increased by attaining a higher yield of seed per unit land area or by improving the nutritional quality of the seed.

High concentration of protein, oil, or carbohydrate is considered an important quality trait for most major crops, including soybean, corn, and wheat. Varieties of high protein corn, wheat, and soybeans, for example, have been identified through traditional breeding. However, most of the high protein lines developed this way have yield drag or other agronomic disadvantages. Similarly, when plants are bred for increasing the concentration of other important nutritional component, such as oil or carbohydrate, yield drag, and other agronomic disadvantages are found as in the aforementioned high protein breeding.

Despite the importance of increasing protein, oil, or carbohydrate levels in seed crops and the significant research effort addressing this problem, no genes have been identified that increase protein levels, for example, without also negatively impacting yield or other agronomic traits. Such a gene would provide a great benefit to meet the nutritional needs for the world's population.

BRIEF SUMMARY OF THE INVENTION

In particular, the present method relates to a method of altering nitrogen or oil contained in a seed of a plant. The method includes regulating the activity or concentration of an AGL11 gene product in a plant. In one embodiment of the present invention, the nitrogen content is altered, which nitrogen is a component of an amino acid, and which amino acid can be free or included in a protein; the nitrogen is preferably found in a protein in the seed. In another embodiment of the present invention, the oil is altered relative to the oil of a substantially related plant whose activity or concentration of the AGL11 gene product has not been altered. When the nitrogen is increased upon implementation of the present invention, wherein the activity of the AGL11 gene product is decreased, the oil is either substantially the same or decreased when compared to a substantially related plant whose activity or concentration of the AGL11 gene product has not been so regulated; preferably, the seed oil is decreased in concentration. When the oil is increased upon implementation of the present invention, wherein the activity of the AGL11 gene product is increased, the nitrogen is either substantially the same or decreased when compared to a substantially related plant whose activity or concentration of the AGL11 gene product has not been so regulated; preferably, the seed nitrogen is decreased in concentration.

The inventive method for increasing seed nitrogen, wherein the AGL11 gene product is decreased in concentration, is preferably implemented by down regulating the AGL11 gene. Down regulating the AGL11 gene can be accomplished by any protocol wherein suppression of the transcription of the AGL11 gene is involved. Such gene suppression protocols include any of the well-known methods for suppressing transcription of a gene or the accumulation of the mRNA corresponding to that gene thereby preventing translation of the transcript into protein. The preferred protocol for attaining posttranscriptional gene suppression is mediated by transcription of integrated recombinant DNA to form double-stranded RNA (dsRNA) having homology to a gene targeted for suppression, e.g., AGL11. This formation of dsRNA is a common feature of gene suppression methods known as anti-sense suppression, co-suppression, and RNA interference (RNAi). Transcriptional suppression can also be mediated by a transcribed dsRNA having homology to a promoter DNA sequence to effect what is called promoter trans suppression. The nitrogen is increased in concentration in the seed from a plant that is subjected to the inventive gene suppression method from about 3% to about 50% relative to a seed from a substantially related plant that has not been transformed to down regulate its AGL11 gene or reduce the activity of its AGL11 gene product.

In particular, the present invention includes a method of altering the nitrogen or oil content of a seed of a transgenic plant as compared to the seed of a plant of the same species without such alteration comprising inserting a DNA molecule that comprises a promoter, an AGL11-specific polynucleotide selected from the group consisting of the 5' untranslated region, a coding region comprising a sequence selected from the group consisting of SEQ ID NOs: 6, and 9–14, the 3' untranslated region, and a 3' termination element, wherein expressing the DNA molecule regulates the activity or concentration of an AGL11 gene product.

The plant that is used in the context of the present inventive method is selected from the group consisting of maize, wheat, rice, soy, and canola.

In another preferred embodiment, a substantially purified polynucleotide comprising a polynucleotide selected from the group consisting of: a) a polynucleotide sequence encoding a polypeptide having an amino acid sequence selected from the group consisting of SEQ ID NOs: 17–22 and complements thereof; b) polynucleotide comprising a sequence selected from the group consisting of SEQ ID NOs: 9–14, and complements thereof; c) a polynucleotide having at least 60% sequence identity to a polynucleotide of (a) or (b); and d) a polynucleotide that hybridizes to any of (a) or (b) or (c) under stringent conditions.

The substantially purified polynucleotide in yet another preferred embodiment further comprises at least one of the groups consisting of a promoter and an enhancer. Preferred promoters for this embodiment include both tissue- and temporal-specific promoters that cause gene expression to occur predominantly in a particular tissue or at a particular time in development, or both. Alternatively, a preferred promoter is constitutive. Also preferred are homologous promoters related to the AGL11 gene and its homologs.

A particularly preferred embodiment of the present invention is a substantially isolated polynucleotide comprising SEQ ID NO: 73, which can function as a promoter. Indeed a most preferred aspect of the present invention is the combination of this promoter operably coupled to a coding region provided that the coding region is heterologous to the AGL11 gene.

The present invention also includes a plant that includes an introduced AGL11 gene, comprising a sequence selected from the group consisting of SEQ ID NOs: 9–14 or complement thereof, or fragment of either the AGL11 gene, or complement thereof. This embodiment preferably has an enhanced or reduced concentration of protein or oil in its seeds as compared to the concentration of, respectively, protein or oil in the seeds of a substantially related plant that does not include the introduced AGL11 gene, or complement thereof, or fragment of either the AGL11 gene, or complement thereof.

In a another preferred embodiment, the present invention is a plant that has reduced concentration of protein in its seeds, wherein the plant includes a gene construct that increases AGL11 gene expression; and wherein the protein is preferably reduced in relative concentration in the seed by from about 5% to about 50% less relative to a substantially related plant that has not been transformed with a construct designed to increase AGL11 expression. In an alternative preferred embodiment, the present invention has enhanced concentration of protein or oil in its seeds, wherein the plant preferably includes a gene construct that decreases AGL11 gene expression or decreases the activity of the AGL11 gene product; and wherein the protein is preferably increased in relative concentration in the seed by from about 5% to about 50% more relative to a substantially related plant that has not been transformed with a construct designed to decrease AGL11 expression.

The plant of the present invention is preferably selected from the group consisting of alfalfa, *Arabidopsis thaliana*, barley, *Brassica campestris*, oilseed rape, broccoli, cabbage, citrus, canola, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, *Phaseolus*, crambe, mustard, castor bean, sesame, cottonseed, linseed, safflower, and oil palm. The plant of the present invention may also be selected from the group consisting of canola, corn, *Brassica campestris*, oilseed rape, rapeseed, soybean, crambe, mustard, castor bean, peanut, sesame, cottonseed, linseed, safflower, oil palm, flax, and sunflower.

In yet another preferred embodiment, the present invention relates to a plant that includes an AGL11-specific sequence for altering AGL11 activity, wherein the yield of the plant is increased relative to a substantially related plant that does not comprise an introduced AGL11 gene, or complement thereof, or fragment of either the AGL11 gene, or complement thereof. Many agronomic traits can affect "yield". For example, such traits could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. For example, such traits could also include, without limitation, efficiency of germination (including germination in stressed conditions), growth rate (including growth rate in stressed conditions), ear number, seed number per ear, seed size, composition of seed (starch, oil, protein), characteristics of seed fill. "Yield" can be measured in many ways, including, for example, test weight, seed weight, seed number per plant, seed number per unit area (i.e. seeds, or weight of seeds, per acre), bushels per acre, tonnes per acre, tons per acre, kilo per hectare. In one embodiment, a plant of the present invention might exhibit an enhanced trait that is a component of yield. An enhanced trait is a trait, or phenotype of a plant, that is changed in a way that could be viewed as an agronomic improvement when compared to a non-transgenic plant of the same, or very similar, genotype, as in when the AGL11 gene activity is impacted transgenically.

Another embodiment of the present invention includes: a plasmid comprising a) a polynucleotide sequence encoding a polypeptide having an amino acid sequence selected from the group consisting of SEQ ID NOs: 17–22 and complements thereof; b) polynucleotide comprising a sequence selected from the group consisting of SEQ ID NOs: 9–14, and complements thereof; c) a polynucleotide having at least 60% sequence identity to a polynucleotide of (a) or (b); and d) a polynucleotide that hybridizes to any of (a) or (b) or (c) under stringent conditions. Other embodiments include: a chimeric gene comprising one of the substantially purified polynucleotides set forth herein above and operably linked to at least one regulatory sequence not associated in nature with the substantially purified polynucleotide; a plant cell transformed with such a chimeric gene; and a microbial cell transformed with such a chimeric gene.

Another aspect of the present invention relates to seed that includes an introduced AGL11 gene comprising a sequence selected from the group consisting of SEQ ID NOs: 9–14, or complement thereof, or fragment of either the AGL11 gene, or complement thereof; preferably wherein the seed has an enhanced or reduced concentration of protein or oil as compared to the concentration of, respectively, protein or oil in the seed of a substantially related plant that does not include the introduced AGL11 gene, or complement thereof, or fragment of either the AGL11 gene, or complement thereof; and further preferably wherein the seed is increased in size relative to the seed of a substantially related plant that does not include the introduced AGL11 gene, or complement thereof, or fragment of either the AGL11 gene, or complement thereof. The present invention also relates to animal feed comprising the aforementioned seed, or a component of such seed.

BRIEF DESCRIPTION OF THE SEQUENCES

Figure 1:
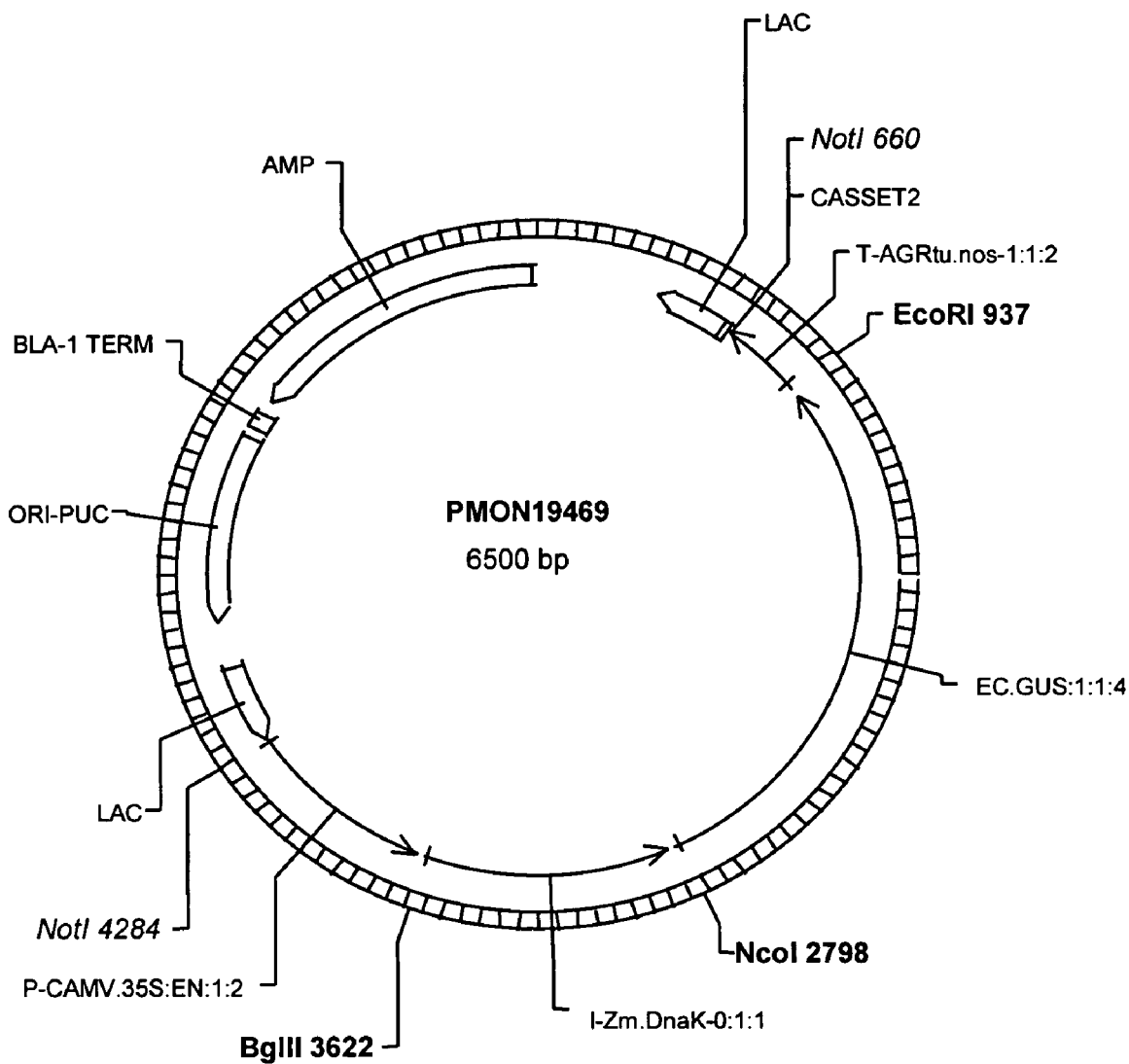
FIG. 1 is a diagram of the physical map of plasmid pMON19469.

SEQ ID NO: 1 is a DNA identified as f35, used as a primer for a PCR reaction.

SEQ ID NO: 2 is a DNA identified as AP1, used as a primer for a PCR reaction.

SEQ ID NO: 3 is a DNA identified as n35, used as a primer for a PCR reaction.

SEQ ID NO: 4 is a DNA identified as AP2, used as a primer for a PCR reaction.

SEQ ID NO: 5 is a DNA found flanking T-DNA contained in the hpr-6 mutant.

SEQ ID NO: 6 is a DNA that encodes a full-length cDNA of the AGL11 gene of *Arabidopsis thaliana*.

SEQ ID NO: 7 is a maize cDNA that is related to the *Arabidopsis* AGL11 gene, identified as ZEAMA-06JUN02-CLUSTER1808_2.

SEQ ID NO: 8 is a second maize cDNA that is related to the *Arabidopsis* AGL11 gene, identified as ZEAMA-06JUN02-CLUSTER84_1.

SEQ ID NO: 9 is a third maize cDNA that is related to the *Arabidopsis* AGL11 gene, identified as ZEAMA-06JUN02-CLUSTER53_5.

SEQ ID NO: 10 is a fourth maize cDNA that is related to the *Arabidopsis* AGL11 gene, identified as ZEAMA-06JUN02-CLUSTER1808_1.

SEQ ID NO: 11 is a fifth maize cDNA that is related to the *Arabidopsis* AGL11 gene, identified as ZEAMA-06JUN02-CLUSTER1442_1.

SEQ ID NO: 12 is a sixth maize cDNA that is related to the *Arabidopsis* AGL11 gene, identified as ZEAMA-06JUN02-CLUSTER2121_2.

SEQ ID NO: 13 is a seventh maize cDNA that is related to the *Arabidopsis* AGL11 gene, identified as ZEAMA-06JUN02-CLUSTER1145_1.

SEQ ID NO: 14 is an eighth maize cDNA that is related to the *Arabidopsis* AGL11 gene, identified as ZEAMA-06JUN02-CLUSTER30771_1.

SEQ ID NO: 15 is an amino acid translation of SEQ ID NO: 7.

SEQ ID NO: 16 is an amino acid translation of SEQ ID NO: 8.

SEQ ID NO: 17 is an amino acid translation of SEQ ID NO: 9.

SEQ ID NO: 18 is an amino acid translation of SEQ ID NO: 10.

SEQ ID NO: 19 is an amino acid translation of SEQ ID NO: 11.

SEQ ID NO: 20 is an amino acid translation of SEQ ID NO: 12.

SEQ ID NO: 21 is an amino acid translation of SEQ ID NO: 13.

SEQ ID NO: 22 is an amino acid translation of SEQ ID NO: 14.

SEQ ID NO: 23 is a unique PCR fragment cloned from SEQ ID NO: 7.

SEQ ID NO: 24 is a unique PCR fragment cloned from SEQ ID NO: 8.

SEQ ID NO: 25 is a unique PCR fragment cloned from SEQ ID NO: 9.

SEQ ID NO: 26 is a unique PCR fragment cloned from SEQ ID NO: 10.

SEQ ID NO: 27 is a unique PCR fragment cloned from SEQ ID NO: 11.

SEQ ID NO: 28 is a unique PCR fragment cloned from SEQ ID NO: 12.

SEQ ID NO: 29 is a unique PCR fragment cloned from SEQ ID NO: 13.

SEQ ID NO: 30 is a unique PCR fragment cloned from SEQ ID NO: 14.

SEQ ID NOs: 31–66, inclusive, are DNA fragments used as primers in PCR reactions, specific for AGL11 in *Arabidopsis* or maize.

SEQ ID NO: 67 is the *Arabidopsis* full-length open reading frame.

SEQ ID NO: 68 is the soybean full-length open reading frame.

SEQ ID NO: 69 is the maize full-length open reading frame.

SEQ ID NO: 70 is the rice full-length open reading frame.

SEQ ID NOs: 71 and 72 are DNA fragments used as primers in PCR reactions, specific for the AGL11 promoter in *Arabidopsis*.

SEQ ID NO: 73 is a DNA sequence that includes the promoter region of AGL11 of *Arabidopsis thaliana*.

DEFINITIONS

The following terms as used in this disclosure shall have the definitions set forth in this section:

A "polynucleotide" is a nucleotide sequence such as a nucleic acid fragment. A polynucleotide may be a polymer of RNA or DNA or both that is single- or double-stranded, that optionally contains synthetic, non-natural, or altered nucleotide bases. A polynucleotide in the form of a polymer of DNA may be comprised of one or more segments of cDNA, genomic DNA, or synthetic DNA.

An "isolated polynucleotide" or an "isolated DNA segment" having a sequence that encodes a plant transcription factor is a polynucleotide that contains the coding sequence of the plant transcription factor: i) in isolation, ii) in combination with additional coding sequences, such as fusion protein or signal peptide, in which the plant transcription factor coding sequence is the dominant coding sequence, iii) in combination with non-coding sequences, such as control elements, such as promoter and terminator elements, effective for expression of the coding sequence in plant cells, and/or iv) in a vector or host environment, in which the plant transcription factor coding sequence is a heterologous gene.

The term "plasmid" refers to a circular double-stranded (ds) DNA construct that is used as a cloning vector, and that forms an extrachromosomal self-replicating genetic element in many bacteria and some eukaryotes.

The term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A nucleic acid sequence is "heterologous" with respect to a promoter or enhancer sequence (e.g., a control sequence) when it does not function in nature to regulate the same gene the expression of which it is currently regulating. Generally, heterologous nucleic acid constructs are introduced into the cell or part of the genome in which they are present, and have been added to the cell, by transfection, microinjection, electroporation, or the like. The sequences may contain a control sequence/DNA coding sequence combination that is the same as, or different from, a control sequence/DNA coding sequence combination found in the native plant.

"Substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through, for example, antisense or co-suppression technology. "Substantially similar" also refers to modifications of the nucleic acid fragments of the instant invention, such as deletion or insertion of one or more nucleotides that do not substantially affect the functional properties of the resulting transcript vis-à-vis the ability to mediate gene silencing or alteration of the functional properties of the resulting protein molecule. It is therefore, understood that the present invention encompasses more than the specific exemplary nucleotide or amino acid sequences and includes functional equivalents thereof.

"Substantially related plant" refers to plants of the same laboratory or field stock that only differ in genotype and/or phenotype due to insertion of an exogenous gene construct; as in, for example and without limitation, isogenic plants. Alternatively, the substantially related plant is one that is related to a statistically significant extent with respect to a plant of interest.

Substantially similar nucleic acid fragments may be selected by screening nucleic acid fragments representing subfragments or modifications of the nucleic acid fragments of the instant invention, wherein one or more nucleotides are substituted, deleted, and/or inserted, for their ability to affect the level of the polypeptide encoded by the unmodified nucleic acid fragment in a plant or plant cell. For example, a substantially similar nucleic acid fragment representing at least one of 25 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

Moreover, alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine.

Similarly, changes that result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Consequently, an isolated polynucleotide comprising a nucleotide sequence of at least one of 60 (preferably at least one of 40, most preferably at least one of 25) contiguous nucleotides derived from a nucleotide sequence selected from the group consisting of SEQ ID NOs: 6, and 9–14, and the complement of such nucleotide sequences, may be used in methods of selecting an isolated polynucleotide that affects the expression of a polypeptide in a plant cell. A method of selecting an isolated polynucleotide that affects the level of expression of a polypeptide in a host cell (eukaryotic, such as plant or yeast, prokaryotic such as bacterial, or viral) may comprise the steps of constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize to a known standard. Estimates of such homology are provided by either DNA—DNA or DNA-RNA hybridization under conditions of stringency as is well understood by those skilled in the art (see, for example, Hames and Higgins, Eds. (1985) Nucleic Acid Hybridization, IRL Press, Oxford, U.K.). Stringency conditions can be adjusted to screen for moderately similar fragments, such as homologous sequences from distantly related organisms to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures, in which the washes are identical to those above except for the temperature of the final two 30 minute washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. An "identity fraction" for aligned segments of test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The percent of sequence identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (*Mol. Bio.*, 48:443–453 (1970)) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (*Adv. Applied Mathematics*, 2:482–489 (1981); Smith et al., *Nucleic Acids Res.*, 11:2205–2220 (1983)). The percent identity is most preferably determined using the "Best Fit" program using default parameters.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer based sequence comparison and identification tools that employ algorithms such as BLAST (Basic Local Alignment Search Tool; Altschul et al., *J. Mol. Biol.*, 215:403–410 (1993)). In general, a sequence of 10 or more contiguous amino acids or 30 or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments, which may then be enzymatically assembled to construct the entire desired nucleic acid fragment. "Chemically synthesized," as related to nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism or chimeric genes. A "transgene" is a gene that has been introduced into the genome by a transformation procedure.

"Coding sequence" or "structural gene" refers to a nucleotide sequence that encodes a specific amino acid sequence or a functional RNA (such as, for example, RNAs associated with ribosome structure or a transfer RNA (tRNA). "Regulatory sequences" or "regulatory genes" refer to nucleotide sequences located upstream (5' non-coding sequences), within, or downstream (3' non-coding sequences) of a coding sequence, and that influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence, which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, *Biochemistry of Plants*, 15:1–82 (1989). It is further recognized in the art that the exact boundaries of regulatory sequences generally have not been completely defined, accordingly, nucleic acid fragments of varying lengths that are upstream of (i.e., 5' to) a coding sequence may have identical promoter activity.

The term "fragment," when referring to a gene sequence, means a polynucleotide having a nucleic acid sequence that is the same as part of, but not all of, the nucleic acid sequence of the full-length gene. The fragment preferably includes at least about 25 contiguous bases of the gene, preferably at least from about 20 to about 30 contiguous bases. With reference to interaction with a transcription factor, the sequence must be of sufficient length to interact with the transcription factor.

The terms "transformed," "stably transformed," or "transgenic" with reference to a plant cell means the plant cell has a non-native (heterologous) nucleic acid sequence integrated into its genome that is maintained through one or more generations.

The term "introduced" in the context of inserting a nucleic acid sequence into a cell, means transfection, transformation, or transduction and includes reference to the incorporation of a nucleic acid sequence into a eukaryotic or prokaryotic cell, where the nucleic acid sequence may be incorporated into the genome of the cell (for example, chromosome, plasmid, plastid, or mitochondrial DNA), converted into an autonomous replicon, or transiently expressed (for example, transfected mRNA).

The term "effector" refers to plant transcription factors that "effect" the transcription of genes having the appropriate response sequence.

"Plant cell" refers to any cell derived from a plant, including undifferentiated tissue (e.g. callus) as well as plant seeds, pollen, propagules, and embryos.

"Mature plant" refers to a fully differentiated plant.

"Native" and "wild-type" relative to a given plant trait or phenotype associated with a transgenic event refers to the form in which that trait or phenotype is found in the same variety of plant in nature.

"Plant" includes reference to whole plants, plant organs (such as leaves, stems, roots), seeds, plant cells, and their progeny. "Plant cell" includes, without limitation, seeds, suspension cultures, embryos, meristematic regions, callus tissue, leaves, roots, shoots, gametophytes, sporophytes, pollen, and microspores. The class of plants that can be used in the methods of the present invention is generally as broad as the class of higher plants amenable to transformation techniques, including both monocotyledenous and dicotyledonous plants.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability, or translation efficiency. Examples of translation leader sequences have been described (Turner and Foster, *Mol. Biotechnol.*, 3:225–236 (1995)).

The "3" non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell*, 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see, U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Gene suppression" includes any of the well-known methods for suppressing transcription of a gene or the accumulation of the mRNA corresponding to that gene thereby preventing translation of the transcript into protein. Posttranscriptional gene suppression is mediated by transcription of integrated recombinant DNA to form double-stranded RNA (dsRNA) having homology to a gene targeted for suppression. This formation of dsRNA most commonly results from transcription of an integrated inverted repeat of the target gene, and is a common feature of gene suppression methods known as anti-sense suppression, co-suppression, and RNA interference (RNAi). Transcriptional suppression can be mediated by a transcribed dsRNA having homology to a promoter DNA sequence to effect what is called promoter trans suppression.

More particularly, posttranscriptional gene suppression by inserting a recombinant DNA construct with anti-sense oriented DNA to regulate gene expression in plant cells is disclosed in U.S. Pat. No. 5,107,065 (Shewmaker et al.) and U.S. Pat. No. 5,759,829 (Shewmaker et al.). Transgenic plants transformed using such anti-sense oriented DNA constructs for gene suppression can comprise integrated DNA arranged as an inverted repeats that result from insertion of the DNA construct into plants by *Agrobacterium*-mediated transformation, as disclosed by Redenbaugh et al. in "Safety Assessment of Genetically Engineered Flavr Savr™ Tomato, CRC Press, Inc. (1992). Inverted repeat insertions comprises a part or all of the T-DNA construct, e.g. an inverted repeat of a complete transcription unit or an inverted repeat of transcription terminator sequence. Screening for inserted DNA comprising inverted repeat elements can improve the efficiency of identifying transformation events effective for gene silencing whether the transformation construct is a simple anti-sense DNA construct which must be inserted in multiple copies or a complex inverted repeat DNA construct (e.g., an RNAi construct) which can be inserted as a single copy.

Posttranscriptional gene suppression by inserting a recombinant DNA construct with sense-oriented DNA to regulate gene expression in plants is disclosed in U.S. Pat. No. 5,283,184 (Jorgensen et al.) and U.S. Pat. No. 5,231,020 (Jorgensen et al.). Inserted T-DNA providing gene suppression in plants transformed with such sense constructs by *Agrobacterium* is organized predominately in inverted repeat structures, as disclosed by Jorgensen et al., *Mol. Gen. Genet.*, 207:471–477 (1987). See, also, Stam et al., *The Plant Journal*, 12(1):63–82 (1997) who used segregation studies to support Jorgensen's finding that gene silencing is mediated by multimeric transgene T-DNA loci in which the T-DNAs are arranged in inverted repeats. Screening for inserted DNA comprising inverted repeat elements can improve the gene silencing efficiency when transforming with simple sense-orientated DNA constructs. Gene silencing efficiency can also be improved by screening for single insertion events when transforming with an RNAi construct containing inverted repeat elements.

As disclosed by Redenbaugh et al. gene suppression can be achieved by inserting into a plant genome recombinant DNA that transcribes dsRNA. Such a DNA insert can be transcribed to an RNA element having the 3' region as a double stranded RNA. RNAi constructs are also disclosed in EP 0 426 195 A1 (Goldbach et al., 1991) where recombinant DNA constructs for transcription into hairpin dsRNA for providing transgenic plants with resistance to tobacco spotted wilt virus. Double-stranded RNAs were also disclosed in WO 94/01550 (Agrawal et al.) where anti-sense RNA was stabilized with a self-complementary 3' segment. Agrawal et al. referred to U.S. Pat. No. 5,107,065 for using such self-stabilized anti-sense RNAs for regulating gene expression in plant cells; see WO 94/01550. Other double-stranded hairpin-forming elements in transcribed RNA are disclosed in WO 98/05770 (Werner et al.) where the anti-sense RNA is stabilized by hairpin forming repeats of poly (CG) nucleotides. See, also, U.S. Patent Application Publication No. 2003/0175965 A1 (Lowe et al.) which discloses gene suppression using and RNAi construct comprising a gene coding sequence preceded by inverted repeats of 5'UTR. See, also, U.S. Patent Application Publication No. 2002/0048814 A1 (Oeller) where RNAi constructs are transcribed to sense or anti-sense RNA which is stabilized by a poly (T)-poly(A) tail. See, also, U.S. Patent Application Publication No. 2003/0018993 A1 (Gutterson et al.) where sense or anti-sense RNA is stabilized by an inverted repeat of a 3' untranslated region of the NOS gene. See, also, U.S. Patent Application Publication No. 2003/0036197 A1 (Glassman et al.) where RNA having homology to a target is stabilized by two complementary RNA regions.

Gene silencing can also be effected by transcribing RNA from both a sense and an anti-sense oriented DNA, e.g. as disclosed by Shewmaker et al. in U.S. Pat. No. 5,107,065 where in Example 1 a binary vector was prepared with both sense and anti-sense aroA genes. See, also, U.S. Pat. No. 6,326,193 where gene targeted DNA is operably linked to opposing promoters.

Gene silencing can also be affected by transcribing from contiguous sense and anti-sense DNA. In this regard see, Sijen et al., *The Plant Cell*, 8:2277–2294 (1996) discloses the use of constructs carrying inverted repeats of a cowpea mosaic virus gene in transgenic plants to mediate virus resistance. Such constructs for posttranscriptional gene suppression in plants by double-stranded RNA are also disclosed in WO 99/53050 (Waterhouse et al.), WO 99/49029 (Graham et al.), U.S. patent application Ser. No. 10/465,800 (Fillatti), U.S. Pat. No. 6,506,559 (Fire et al.). See, also, U.S. patent application Ser. No. 10/393,347 (Shewmaker et al.) that discloses constructs and methods for simultaneously expressing one or more recombinant genes while simultaneously suppressing one or more native genes in a transgenic plant. See, also, U.S. Pat. No. 6,448,473 (Mitsky et al.) that discloses multi-gene suppression vectors for use in plants. All of the above-described patents, applications, and international publications disclosing materials and methods for posttranscriptional gene suppression in plants are incorporated herein by reference.

Transcriptional suppression such as promoter trans suppression can be affected by expressing a DNA construct comprising a promoter operably linked to inverted repeats of promoter DNA for a target gene. Constructs useful for such gene suppression mediated by promoter trans suppression are disclosed by Mette et al., *The EMBO Journal*, 18(1): 241–148 (1999) and by Mette et al., *The EMBO Journal*, 19(19):5194–5201 (2000), both of which are incorporated herein by reference.

Suppression can also be achieved by insertion mutations created by transposable elements may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest. "Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation.

DETAILED DESCRIPTION OF THE INVENTION

This present invention relates to a method of altering the nutritional composition of a plant seed by way of affecting the expression of certain plant genes, such as the AGL11 gene of *Arabidopsis* and homologs of AGL11 in other plant species, and preferably the AGL11 homologs in maize, rice, wheat, soy, and canola. The present invention provides molecular strategies for controlling the protein levels or oil levels in plant seeds. In particular, altered plants with a reduced activity of an AGL11 polypeptide function, as compared to a wild type, for example, have dramatically increased levels of protein in the seeds. The strategies set forth in this application enable one to manipulate a number of agronomically important traits, such as seed protein, in plant species of agricultural importance.

The AGL11 gene is one of a family of more than 100 MADS-box transcription factors, which have been implicated in floral organogenesis and initiation of flowering, root development, and tissue differentiation. AGL11 controls development of the floral organ, and is preferentially expressed in ovules starting at stage 9, and into seed development. Rounsley et al., *The Plant Cell*, 7:1259–1269 (1995) have reported that no AGL11 RNA was detected in non-ovule floral organs during development earlier or later than fertilization through early seed development. Accordingly, the AGL11 promoter (SEQ ID NO: 73) can be usefully employed to drive expression of coding regions that would be usefully expressed in ovules from stage 9 and into seed development. Useful coding regions that may be so driven include, without limitation, nucleic acids that encode enzymes whose presence or overproduction would increase protein or specific amino acid accumulation, such as, for example, dihydrodipicolinate synthase, amino acid transporters, anthraniline synthase, and the like.

Isolation of the AGL11 gene from *Arabidopsis* and the AGL11 homologs from other crop species is accomplished by laboratory procedures well known and commonly used in the art. Standard techniques are used for cloning, nucleic acid isolation, amplification, and purification. These techniques and various others are generally performed as described in Sambrook et al., *Molecular Cloning—A Laboratory Manual*, Cold Spring Harbor Laboratory, Cold Spring Harbor, N.Y. (1989), herein referred to as Sambrook (1989). Genome walking techniques are performed according to manufacturer's specifications (CLONTECH Laboratories, Inc., Palo Alto, Calif.).

The isolation of AGL11 nucleic acids may be accomplished by a number of techniques. One such technique is the use of oligonucleotide probes based on sequences disclosed in this specification to identify the desired gene in a cDNA or genomic DNA library. To construct genomic libraries, large segments of genomic DNA are generated by digestion with restriction endonucleases and then ligating the resultant segments with vector DNA to form concatemers that can be packaged into an appropriate vector. To prepare a cDNA library, mRNA is isolated from the desired organ, such as seed tissue, and a cDNA library is prepared from the mRNA.

The cDNA or genomic DNA library can be screened using a probe based upon the sequence of a cloned AGL11 gene, as disclosed herein. Probes may be used to hybridize with genomic DNA or cDNA sequences to isolate homologous genes in the same or different plant species. Usefully employed such probes include, without limitation, 5' UTRs which, preferably, function as promoters. Alternatively, antibodies raised against an AGL11 polypeptide can be used to screen an mRNA expression library.

Nucleic acid sequences can be screened for the presence of protein encoding sequence that is homologous to genes of other organisms with known protein encoding sequence using any of a variety of search algorithms. Such search algorithms can be homology-based or predictive-based. Homology-based searches (e.g., GAP2, BLASTX supplemented by NAP and TBLASTX) detect conserved sequences during comparison of DNA sequences or hypothetically translated protein sequences to public and/or proprietary DNA and protein databases. Existence of a gene is inferred if significant sequence similarity extends over the majority of the target gene. Since homology-based methods may overlook genes unique to the source organism, for which homologous nucleic acid molecules have not yet been identified in databases, gene prediction programs are also used. Gene prediction programs generally use "signals" in the sequences, such as splice sites or "content" statistics, such as codon bias, to predict gene structures (Stormo, *Genome Research*, 10:394–397 (2000)).

Alternatively, the nucleic acids of interest can be amplified from nucleic acid samples using amplification techniques. For example, polymerase chain reaction ("PCR") technology can be used to amplify the sequences of the AGL11 genes directly from genomic DNA, from cDNA, from genomic libraries, and cDNA libraries. PCR and other in vitro amplification methods may also be useful, for example, in cloning nucleic acids sequences that code for proteins to be expressed, to make nucleic acids to use as probes for detecting the presence of desired mRNA in samples, for nucleic acid sequencing, or for other purposes.

Appropriate primers and probes for identifying AGL11 and homolog sequences from plant tissues are generated from comparisons of the sequences provided herein. For a general overview of PCR, see, *PCR Protocols: A Guide to Methods and Applications*, Innis, M., Gelfand, D., Sninsky, J., and White, T., eds., Academic Press, San Diego (1990).

As noted above, the nucleic acids used in the context of the present invention are characterized by the presence of sequence encoding an AGL11 polypeptide. Preferably, the nucleic acid used in the context of the present invention encodes a portion of the AGL11 polypeptide that provides its specific functionality, i.e., encodes a functional domain of the gene product. Primers that specifically amplify AGL11 domains of the exemplified genes are particularly useful for identification of particular AGL11 homologs from different crop species. Primers suitable for this purpose based on the sequence of AGL11 genes disclosed here are as follows.

The PCR primers are used under standard PCR conditions preferably using the nucleic acids as identified in GenBank accessions as a template, such as SEQ ID NOs: 6, and 9–14. The PCR products generated by any of the reactions can then be used to identify nucleic acids useful in the context of the present invention (e.g., from a cDNA library) by their ability to hybridize to known AGL11 genes found in GenBank and other databases.

Polynucleotides may also be synthesized by well-known techniques, as described in the technical literature. See, e.g., Carruthers et al., *Cold Spring Harbor Symp. Quant. Biol.*, 47:411–418 (1982), and Adams et al., *J. Am. Chem. Soc.*, 105:661 (1983). Double-stranded DNA fragments may then be obtained either by synthesizing the complementary strand and annealing the strands together under appropriate conditions, or by adding the complementary strand using DNA polymerase with a suitable primer sequence.

Alternatively, primers that specifically hybridize to highly conserved regions in AGL11 genes can be used to amplify sequences from widely divergent plant species such as corn, canola, soybean, and tobacco, for example. Examples of such primers are: SEQ ID NOs: 31–65.

In a preferred embodiment, the AGL11 gene is suppressed.

Isolated sequences prepared as described herein can also be used to introduce expression of a particular AGL11 nucleic acid to enhance or increase endogenous gene expression. Enhanced expression will generally lead to lower seed protein but higher seed oil levels. Where overexpression of a gene is desired, the desired gene from a different species may be used to decrease potential sense suppression effects.

One of skill will recognize that the polypeptides encoded by the genes of the present invention, like other proteins, have different domains that perform different functions. Thus, the gene sequences need not be full length, so long as the desired functional domain of the protein is expressed. For example, AGL11, as a member of the MADS-box family of proteins is believed to have 3 functional domains. There is an N-terminal DNA-binding domain (the MADS-box), a more distal dimerization domain (the K-box), and a C-terminal domain that is usually involved in interactions with other proteins. In plants, the region between the MADS-box and the K-box has been shown to be important for DNA binding, and is commonly referred to as the I-box (Fan et al., *Plant J.*, 12(5):999–1010 (1997)).

Several different classes of constructs are contemplated herein as part of the present invention: First, deletion or inactivation of the MADS-box DNA-binding domain creates proteins that are able to dimerize with their native full-length counterparts as well as other natural dimerization partners. Second, removal of the C-terminal domain allows dimerization with both the native and its natural dimerization partners. In both cases, these types of constructs disable both the target protein and any other protein capable of interacting with the K-box. More severe truncations are also within the scope of the present invention, such as removal of both the K-box and C-terminal regions. Constructs with modified coding regions have been described for AGAMOUS (Mizukami et al., *Plant Cell*, 8(5):831–845 (1996)), lilly AP3 (Tzeng and Yang, *Plant Cell Physiol.*, 42(10): 1156–1168 (2001)), and also for SRF (Belaguli et al., *Mol. Cell. Biol.*, 19(7):4582–4591 (1999)).

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

To use isolated sequences in the above techniques, recombinant DNA vectors suitable for transformation of plant cells are prepared. Techniques for transforming a wide variety of higher plant species are well known and described in the technical and scientific literature. See, for example, Weising et al., *Ann. Rev. Genet.*, 22:421–477 (1988) and Sambrook et al., *Molecular Cloning: A Laboratory Manual*, supra. A DNA sequence coding for the desired polypeptide, for example a cDNA sequence encoding a full length protein, will preferably be combined with transcriptional and translational initiation regulatory sequences that will direct the transcription of the sequence from the gene in the intended tissues of the transformed plant.

In other embodiments of the present invention, it is contemplated that one may employ replicon-competent viral vectors for plant transformation. Such vectors include, for example, wheat dwarf virus (WDV) "shuttle" vectors, such as pW-11 and pW1-GUS (Ugaki et al., *Nucleic Acids Research*, 19(2):371–377 (1991)). The vectors are capable of autonomous replication in maize cells as well as *E. coli*, and as such may provide increased sensitivity for detecting DNA delivered to transgenic cells. A replicating vector also may be useful for delivery of genes flanked by DNA sequences from transposable elements such as Ac/Ds or Mu. It has been proposed that transposition of these elements within the maize genome requires DNA replication (Laufs et al., *Proc. Natl. Acad. Sci.* (U.S.A.), 87(19):7752–7756 (1990)). It is also contemplated that transposable elements would be useful for producing transgenic plants lacking elements necessary for selection and maintenance of the plasmid vector in bacteria, e.g., antibiotic resistance genes, or other selectable markers, and origins of DNA replication. It is also proposed that the use of a transposable element such as Ac, Ds, or Mu would actively promote integration of the desired DNA and hence increase the frequency of stably transformed cells.

It is further contemplated that one may co-transform plants or plant cells with 2 or more genes of interest. Co-transformation may be achieved using a vector containing the marker and another gene or genes of interest. Alternatively, different vectors, e.g., plasmids may contain different genes of interest, and the genes may be delivered to recipient cells concurrently.

Vectors used for plant transformation may include, for example, plasmids, cosmids, yeast artificial chromosomes (YACs), bacterial artificial chromosomes (BACs), plant artificial chromosomes (PACs), or any suitable cloning system. It is contemplated the utilization of cloning systems with large insert capacities will allow introduction of large DNA sequences comprising more than one selected gene. Introduction of such sequences may be facilitated by use of BACs or YACs, or even PACs. For example the use of BACs for *Agrobacterium*-mediated transformation was disclosed by Hamilton et al., *Plant Journal*, 18(2):223–229 (1999).

Particularly useful for transformation are expression cassettes that have been isolated from such vectors. DNA segments used for transforming plant cells will, of course, generally comprise the cDNA, gene or genes that one desires to introduce into and have expressed in the host cells. These DNA segments can further include structures such as promoter, enhancers, 3' untranslated regions (such as polyadenylation sites), polylinkers, or even regulatory genes as desired. The DNA segment or gene chosen for cellular introduction may encode a protein that will be expressed in the resultant recombinant cells resulting in a screenable or selectable trait and/or will impart an improved phenotype to the resulting transgenic plant. However, this may not always be the case, and the present invention also encompasses transgenic plants incorporating non-expressed transgenes. Preferred components are described below.

A number of promoters that are active in plant cells have been described in the literature, and are preferred elements included in the context of the present invention. Such promoters would include but are not limited to those isolated from the following genes: nopaline synthase (NOS; Ebert et al., *Proc. Nat. Acad. Sci.* (U.S.A.), 84:5745 (1987)) and octopine synthase (OCS): cauliflower mosaic virus (CaMV) 19S (Lawton et al., *Plant Mol. Biol.*, 9:31F (1987)) and 35S (Odell et al., *Nature*, 313:810 (1985)), as well as the enhanced CaMV 35S promoter (e35S; described by Kay et al., *Science*, 235:1299–1302 (1987)); figwort mosaic virus (FMV) 35S; the small subunit of ribulose bisphosphate carboxylase (ssRUBISCO, a very abundant plant polypeptide); napin (Kridl et al., *Seed Sci. Res.*, 1:209–219 (1991)); the WEREWOLF promoter (Lee and Schiefelbein, *Cell*, 99:473–483 (1999)); Adh (Walker et al., *Proc. Nat. Acad. Sci.* (U.S.A.), 84:6624 (1987)); sucrose synthase (Yang et al., *Proc. Nat. Acad. Sci.* (U.S.A.), 87:4144 (1990)); tubulin; actin (Wang et al., *Mol. Cell. Biol.*, 12:3399 (1992)); cab (Sullivan et al., *Mol. Gen. Genet.*, 215:431 (1989)); PEP-Case (Hudspeth et al., *Plant Mol. Biol.*, 12:579 (1989)); 7S-alpha'-conglycinin (Beachy et al., *EMBO J.*, 4:3047 (1985)); R gene complex promoters (Chandler et al., *The Plant Cell*, 1:1175 (1989)); tomato E8; patatin; ubiquitin; mannopine synthase (mas); soybean seed protein glycinin (Gly); soybean vegetative storage protein (vsp); waxy; Brittle; Shrunken 2; Branching enzymes I and II; starch synthases; debranching enzymes; oleosins; glutelins; globulin 1; BETL1; and *Arabidopsis* banyuls promoter. The rice actin 1 promoter, the AGL11 promoter, the BETL1 promoter, and the e35S promoter are particularly preferred promoters for use in the practice of the present invention. All of these promoters have been used to create various types of DNA constructs that have been expressed in plants (see, for example, Rogers et al., WO 84/02913).

Promoter hybrids can also be constructed to enhance transcriptional activity (Hoffman, U.S. Pat. No. 5,106,739, herein incorporated by reference), or to combine desired transcriptional activity, inducibility, and tissue or developmental specificity. Promoters that function in plants include but are not limited to promoters that are inducible, viral, synthetic, constitutive as described (Odell et al., *Nature*, 313:810–812 (1985)). Other promoters that are tissue specific, tissue-enhanced, or developmentally regulated are also known in the art and envisioned to have utility in the practice of this present invention.

The promoters used in the present invention may be modified to affect their control characteristic. Promoters can be derived by means of ligation with operator regions, random or controlled mutagenesis, or other means well known in the art. Furthermore the promoter regions can be altered to contain multiple enhancer sequences to assist in elevating gene expression. Examples of such enhancer sequences have been reported (Kay et al., *Science*, 236: 1299–1302 (1987)).

Where an enhancer is used in conjunction with a promoter for the expression of a selected protein, it is believed that it will be preferred to place the enhancer between the promoter and the start codon of the selected coding region. However, one could also use a different arrangement of the enhancer relative to other sequences and still realize the beneficial properties conferred by the enhancer. For example, the enhancer could be placed 5' of the promoter region, within the promoter region, within the coding sequence, or 3' of the coding region. The placement and choice of sequences used as enhancers is known to those of skill in the art in light of the present disclosure. Transformation constructs prepared in accordance with the current invention will typically include a 3' untranslated region (3' UTR), and typically contains a polyadenylation sequence. One type of 3' UTR that may be used is a 3' UTR from the nopaline synthase gene of *Agrobacterium tumefaciens* (NOS 3'-end; Bevan et al., *Nucleic Acid Res.*, 11(2):369–385 (1983)). Other 3' UTR sequences can be used and are commonly known to those of skill in the art.

A number of selectable marker genes are known in the art and can be used in the present invention (Wilmink and Dons, *Plant Molecular Biology Reporter*, 11(2): 165–185 (1993)). By employing a selectable or screenable marker gene in addition to the gene of interest, one can provide or enhance the ability to identify transformants. Particularly preferred selectable marker genes for use in the present invention would include genes that confer resistance to compounds such as antibiotics like kanamycin and herbicides like glyphosate. Other selectable markers known in the art may also be used and would fall within the scope of the present invention.

DNA constructs of the present invention may be introduced into the genome of the desired plant host by a variety of techniques that are well known in the art. For example, the DNA construct may be introduced directly into the genomic DNA of the plant cell using techniques such as electroporation and microinjection of plant cell protoplasts, or the DNA constructs can be introduced directly to plant tissue using DNA particle bombardment.

Microinjection techniques are known in the art and well described in the scientific and patent literature. The introduction of DNA constructs using polyethylene glycol precipitation is described in Paszkowski et al., *Embo J.*, 3:2717–2722 (1984). Electroporation techniques are described in Fromm et al., *Proc. Natl. Acad. Sci.* (U.S.A.), 82:5824 (1985). Ballistic transformation techniques are described in Klein et al., *Nature*, 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example, Horsch et al., *Science*, 233:496–498 (1984) and Fraley et al., *Proc. Natl. Acad. Sci.* (U.S.A.), 80:4803 (1983).

After transformation by any of the above transformation techniques, the transformed plant cells or tissues may be grown in an appropriate medium to promote cell proliferation and regeneration. Plant regeneration from cultured protoplasts is described in Evans et al., Protoplasts Isolation and Culture, Handbook of Plant Cell Culture, pp. 124–176, MacMillilan Publishing Company, NY, 1983; and Binding, Regeneration of Plants, Plant Protoplasts, pp. 21–73, CRC Press, Boca Raton, 1985. For gene gun transformation of wheat and maize, see, U.S. Pat. Nos. 6,153,812 and 6,160, 208. See also, Chistou, *Particle Bombardment for Genetic Engineering of Plants*, pp. 63–69 (maize), pp. 50–60 (rice), Biotechnology Intelligence Unit, Academic Press, San Diego, Calif. (1996), and generally Chistou, *Particle Bom-* bardment for Genetic Engineering of Plants, Biotechnology Intelligence Unit, Academic Press, San Diego, Calif. (1996). See, also, U.S. Pat. Nos. 5,416,011; 5,463,174; and 5,959,179 for *Agrobacterium*-mediated transformation of soy; U.S. Pat. Nos. 5,591,616 and 5,731,179 for *Agrobacterium*-mediated transformation of monocots such as maize; and U.S. Pat. No. 6,037,527 for *Agrobacterium*-mediated transformation of cotton.

The following examples are included to demonstrate specific embodiments of the present invention. It should be appreciated by those of skill in the art that the techniques disclosed in the examples that follow represent techniques discovered by the inventors to function well in the practice of the present invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the present invention.

EXAMPLE 1

This example describes the identification of high protein mutants from an *Arabidopsis* T-DNA insertion mutant population.

A T-DNA insertional mutant population of *Arabidopsis* was generated as described by Galbiati et al., *Funct Integr Genomics*, 1:25–34 (2000). Over 6,000 lines of the T-DNA generated mutant population were established. Individual *Arabidopsis* plants were grown in the growth chamber or greenhouse under 18 hours or 24 hours of light at 200–300 µE. The temperature of the growth chamber and greenhouses was in the range between 20–28° C. The plants were watered with deionized water. Seeds from each line were screened for alteration in nitrogen to carbon (N/C) ratio as compared to wild type *Arabidopsis thaliana* ecotype Columbia. Approximately 5 mg of seeds from each line were analyzed for nitrogen and carbon levels using a NC 2500 combustion nitrogen/carbon analyzer (CE Elantech, Inc., Lakewood, N.J.).

Duplicate batches of 5 atropine standard samples (338–244-00, CE Elantech, Inc.), ranging from 1–10 mg, were weighed into 5×9 mm capsules (240–064-25, CE Elantech, Inc.), using an AT 21 Comparator analytical balance and BalanceLink software from Mettler Toledo. The standard and tissue samples were typically loaded to the auto-sampler of the elemental analyzer in following order: two blanks: standard samples: *Arabidopsis* samples: 5 standard samples. The settings for the elemental analyzer were as follows: Combustion column, 1000° C.; reduction column (Cu column), 780° C.; C/N column of GC, 50° C.; He flow, 120 mL/min.; oxygen flow, 50 mL/min. Sample processing time was 220 seconds/sample.

The N/C ratio of the wild type seeds was approximately 0.05 with a standard deviation of 0.0076. In the primary screen, any plants that showed N/C ratio above 0.06 or below 0.04 were selected as putative mutants for altered protein phenotype. These putative mutants were replanted under similar conditions as described above and their seeds were analyzed for N/C ratio. Mutants confirmed to have elevated protein contents in the secondary screen were taken forward to confirm the phenotype. Six plants from each mutant line were grown in the growth chamber along with 8 wild type plants for each mutant. The plants were placed in a randomized design within the growth chamber to eliminate effects from local growth variation. The high protein mutants (hpr) were grown with or without fertilizer. The fertilizer concentration was about 50 ppm nitrogen using a 20-20-20 fertilizer.

The seeds from these experiments were harvested and analyzed for N/C ratio as described above. The results from this analysis revealed that the mutant identified as hpr6 had significantly higher N/C ratios as compared to the control. In particular, the hpr6 mutant showed a 30% increase in N/C ratio and seed protein levels under growing conditions without fertilizer relative to the wild type control plants (about 20% and 15.5% protein, respectively). Occasionally in studies such as this one, the effect is not reproducible under nutrient replete conditions. When fertilizer was used, the hpr6 mutant showed greater than 15% increase in protein over the wild type control (about 24% and 20.2%, respectively).

The results from the analysis demonstrate that the relative seed protein percentage, as extrapolated from N/C values, was significantly higher in the hpr6 mutant as compared to the control, in both the with and without fertilizer experiments.

EXAMPLE 2

This example sets forth a method of protein and amino acid analysis of seed using HPLC and near infrared measurements.

For seed protein analysis, small bulk samples consisting of 50–100 seeds for each treatment were measured using near infrared reflectance spectroscopy (InfraTec model 1221, Teccator, Hogannas, Sweden). This procedure was based upon the observation that a linear relation exists between the absorption of near infrared radiation and the quantity of chemical constituents comprised in a typical seed sample. Prior to analyzing unknown samples, spectral data was collected with calibration samples that were subsequently analyzed using a primary analysis technique. The primary technique used was nitrogen combustion (Murray, I., and P. C. Williams, 1987, *Chemical Principles of Near-Infrared Technology*, in Near-Infrared Technology in the Agricultural and Food Industries, P. Williams and K. Norris eds.). A multivariate model was developed using the spectral data from the spectrometer and the primary data. In the present case, a PLS-1 (Partial Least Squares Regression Type I) multivariate model was constructed using 152 calibration samples. Each unknown sample was scanned on the spectrometer at least 5 times and its protein content predicted with each scan. Each time the sample was scanned, it was added back to the sample cuvette to minimize multiplicative scattering effects, which are not correlated to the chemical property of interest. The predicted protein was averaged for the multiple scans and then reported for each sample.

The hpr6 mutant seeds were analyzed by NIR to estimate the oil and protein contents using the procedure set forth above. The NIR protein estimates correlated positively with the N/C ratio data.

Controlling for differential growth effects of having the control and hpr6 plants in different trays, an experiment was performed where the hpr6 and control plants were grown in the same tray, seed collected, and measured for oil and protein content by NIR methods set forth above.

The results of this analysis showed that the oil content of hpr6 seed cluster in a range of about 31% to about 32% and the protein content thereof clusters from about 24% to about 26%. In contrast, the control seed had from about 37% to about 39% oil and from about 20% to about 22% protein.

Accordingly, the hpr6 mutant exhibited about a 10% increase in protein, but also exhibited a reduction in oil concentration.

EXAMPLE 3

This example sets forth the identification and sequencing of the hpr6 mutant gene.

DNA was isolated from the *Arabidopsis thaliana* hpr6 mutant by methods known in the art of molecular biology (see, for example, Sambrook et al., supra). The hpr6 mutant gene (AGL11) was identified by isolating the flanking region of T-DNA using the GenomeWalker™ kit (BD Biosciences Clontech, Palo Alto, Calif.) following the conditions set forth by the manufacturer. The primers for the PCR reactions were as follows:

| PrimerID | PrimerName | PrimerSequence |
| --- | --- | --- |
| S0873D10 | f35 | (SEQ ID NO: 1) |
| Adaptor primer 1 | AP1 | (SEQ ID NO: 2) |
| S0873D11 | n35 | (SEQ ID NO: 3) |
| Nested adaptor primer 2 | AP2 | (SEQ ID NO: 4) |

The isolated DNA produced by the PCR reactions were sequenced using standard sequencing methodology known in the art of molecular biology. The so-identified DNAs were sequenced and provide a DNA sequence as illustrated in SEQ ID NO: 5. The SEQ ID NO: 5 had 100% sequence identity with a portion of the sequence of the AGL11 gene from *Arabidopsis thaliana* (SEQ ID NO: 6).

To establish that the T-DNA insertion into the AGL11 gene causes the high protein phenotype as observed in hpr6, linkage analysis is performed. A homozygous *Arabidopsis thaliana* hpr6 mutant line is crossed to a wild type line (*Arabidopsis thaliana* Col-0) to generate F1 seeds. The F1 seeds were planted and selfed to produce F2 seeds. The F2 seeds were then planted, selfed, and harvested to produce F3 seeds. The resulting 200 lines of F3 seeds were analyzed for their protein content by NIR and for the presence of the T-DNA insertion into the AGL11 gene by methods known in the art of molecular biology. The results indicated that all of the lines that contained the T-DNA insertion into the AGL11 gene were also high in seed protein content relative to wild. This establishes the linkage of the AGL11 gene to the high protein phenotype.

EXAMPLE 4

This example describes the identification of AGL11 homologs in maize.

The AGL11 sequence from *Arabidopsis thaliana* (SEQ ID NO: 6) was used to search a DNA sequence database (e.g., Genbank) using a standard BLAST program, namely TBLASTX 2.0.12 (Altschul et al., *Nucleic Acids Res.*, 25:3389–3402 (1997)), was used with a cutoff value of $10^{-8}$. Maize DNA homologs identified by this search are SEQ ID NOs: 7–14.

EXAMPLE 5

This example sets forth amino acid translations of the maize AGL11 homolog DNA sequences (SEQ ID NOs: 7–14) resulting in the polypeptides identified as SEQ ID NOs: 15–22, respectively.

The maize homolog DNA sequences illustrated in Example 4 were translated into protein sequences using a standard translation tool and a cutoff value of $10^{-8}$ (TRANSLATE, SeqLab Version 10.3, Accelrys Inc.). Protein translations of the AGL11 maize homologs identified herein as SEQ ID NOs: 7–14, inclusive, were set forth below as SEQ ID NOs: 15–22, respectively.

A further analysis of SEQ ID NOs: 15–22, revealed unique regions at the C terminus. The unique protein regions were used to find the corresponding cDNA region, which yielded a unique DNA fragment for each DNA homolog. The unique DNA sequences thus identified (SEQ ID NOs: 23–30) were used for gene suppression technologies as described in EXAMPLE 6.

EXAMPLE 6

This example illustrates the use of gene suppression technology, for example double-stranded (dsRNA) constructs with the AGL11 gene from *Arabidopsis* and sequences of corn homologs for suppression or reduction of expression of the AGL11 gene product.

The *Arabidopsis* AGL11 gene and its corn homologs were used to design DNA constructs useful for down regulating gene expression. To construct the transformation vectors that produce RNAs capable of duplex formation with the AGL11 gene, gene-specific sequences in the sense and antisense orientations were linked by the maize Hsp70 intron and placed under the control of a P-VCaMv e35S promoter (U.S. Pat. No. 5,359,142, herein incorporated by reference).

Figure 4:
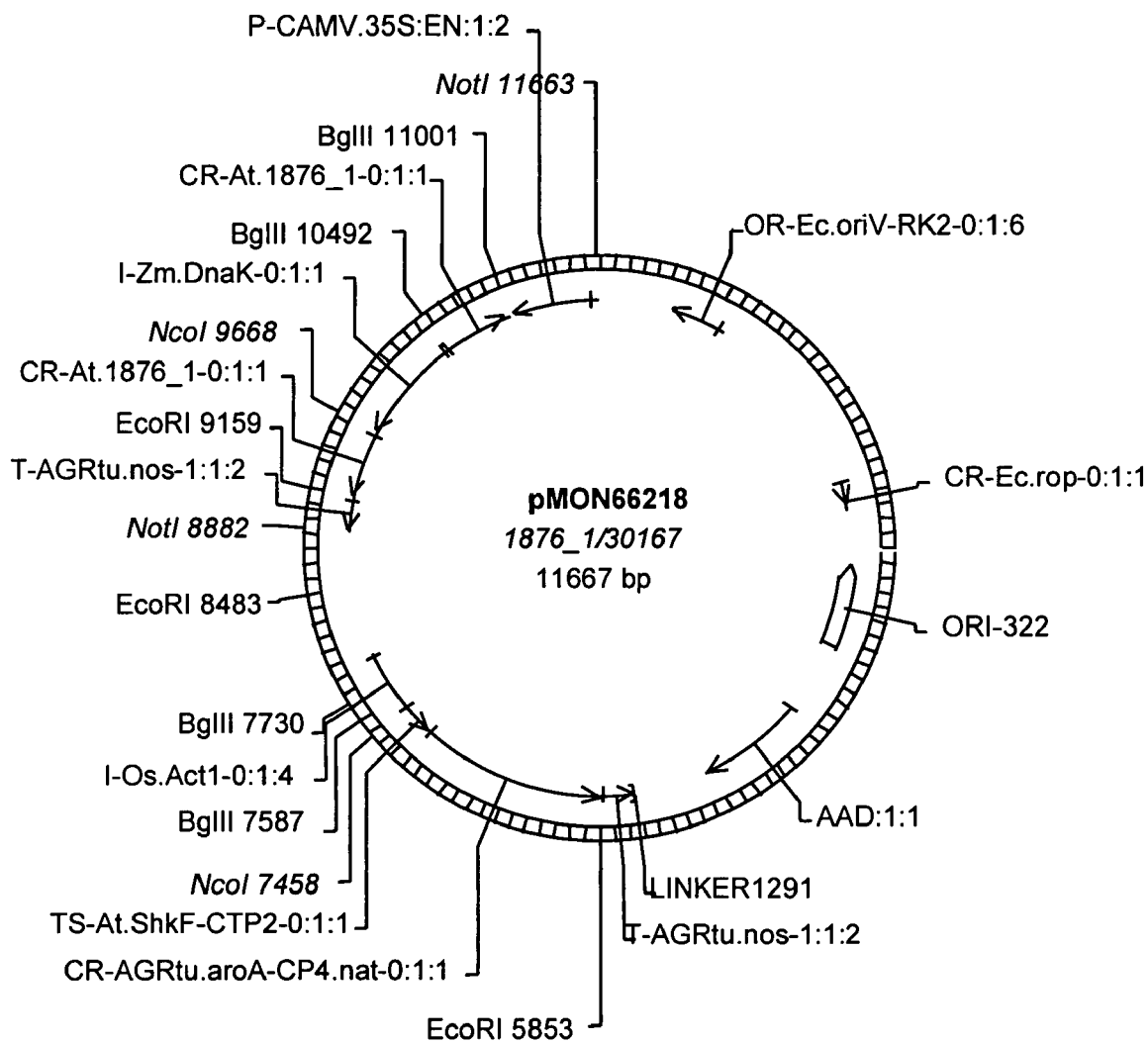
FIG. 4 is a diagram of the physical map of plasmid pMON66218.

The plasmid pMON66218 (FIG. 4) contains a dsRNA cassette against *Arabidopsis* AGL11. pMON66218 was constructed using primers 1876__1FncoI (SEQ ID NO: 31) and 1876__1R EcoRI (SEQ ID NO: 32) in a polymerase chain reaction (PCR) to amplify the DNA that is flanked by the primers. These primers were used to amplify an AGL11 fragment from a cDNA clone of AGL11 from *Arabidopsis*, namely, SEQ ID NO: 6, resulting in an NcoI\EcoRI fragment. Primers 1876__1FbglII (SEQ ID NO: 33) and 1876__1RbglII (SEQ ID NO: 34) were used in the same PCR procedure to amplify the same AGL11 fragment using SEQ ID NO: 6, resulting in a BglII\BglII fragment. The NcoI\EcoRI fragment and BglII\BglII fragments were cloned into the NcoI\EcoRI and BglII sites of pMON19469, respectively. Restriction enzyme digestions and sequencing were used to identify the correct clone that contains the AGL11 dsRNA cassette. The AGL11 dsRNA cassette from pMON19469 was excised using NotI and inserted into a corn transformation binary vector PMON30167.

Figure 2:
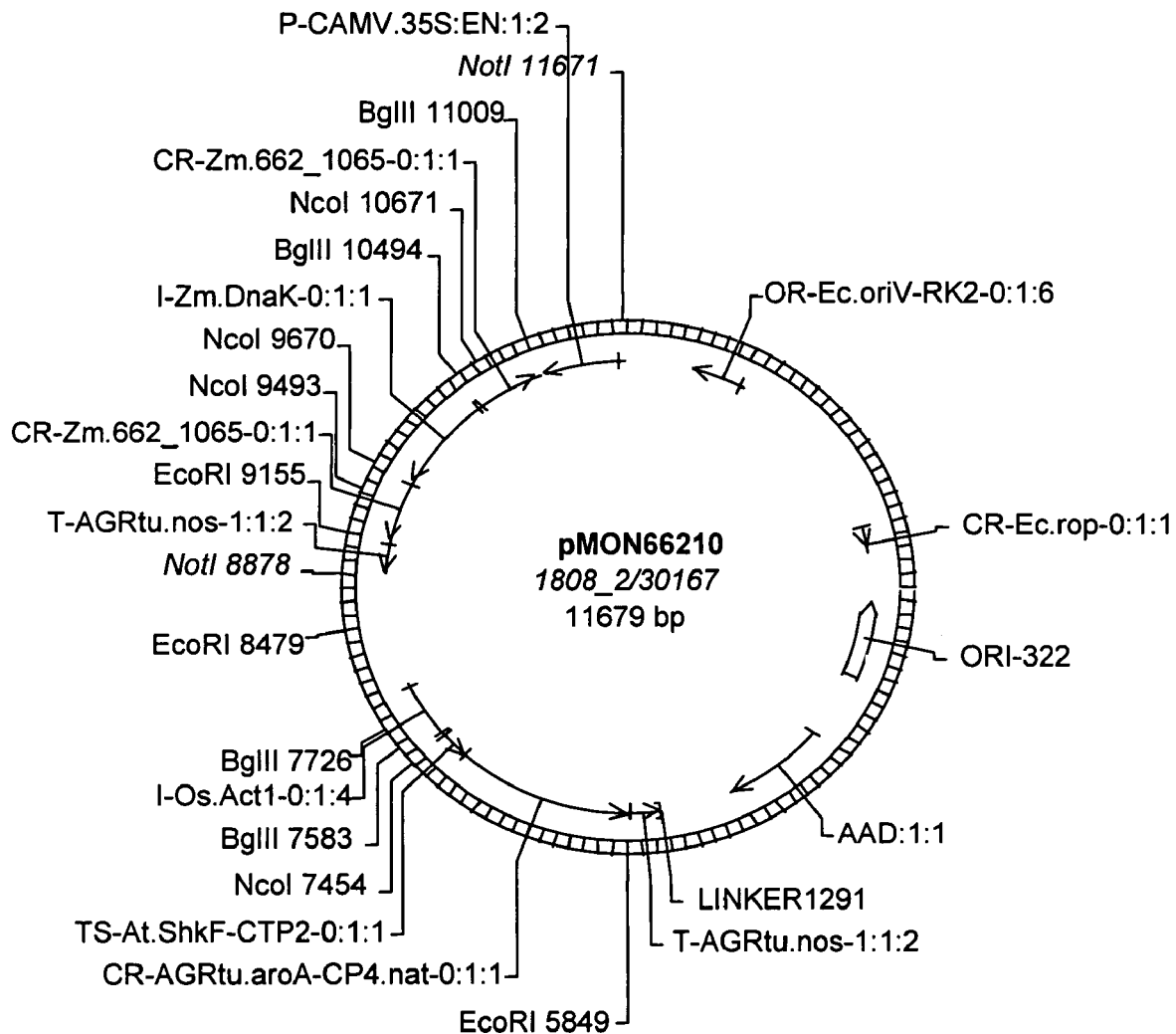
FIG. 2 is a diagram of the physical map of plasmid pMON66210.

Another plasmid was prepared that contained a dsRNA cassette, namely pMON66210 (FIG. 2). This plasmid contained a dsRNA cassette against corn AGL11 homolog cluster 1808__2 (SEQ ID NO: 7). Primers 662__1065RecoRI (SEQ ID NO: 35) and 662__1065FNcoI (SEQ ID NO: 36) were used in the same PCR procedure to amplify the 1808__2 fragment. The PCR product was inserted between the NcoI and EcoRI sites of pMON19469 (FIG. 1). Primers 662__1065RBglII (SEQ ID NO: 37) and 662__1065FBglII (SEQ ID NO: 38) were used in the same PCR procedure to amplify the 1808__2 fragment using a cDNA clone (SEQ ID NO: 7). The resulting PCR product was inserted into the BglII site of pMON19469. Restriction enzyme digestions and sequencing were used to identify the correct clone, using well-known procedures. The cassette was cut out using NotI and inserted into a corn transformation binary vector (pMON30167) to produce pMON66210 (FIG. 2).

Figure 3:
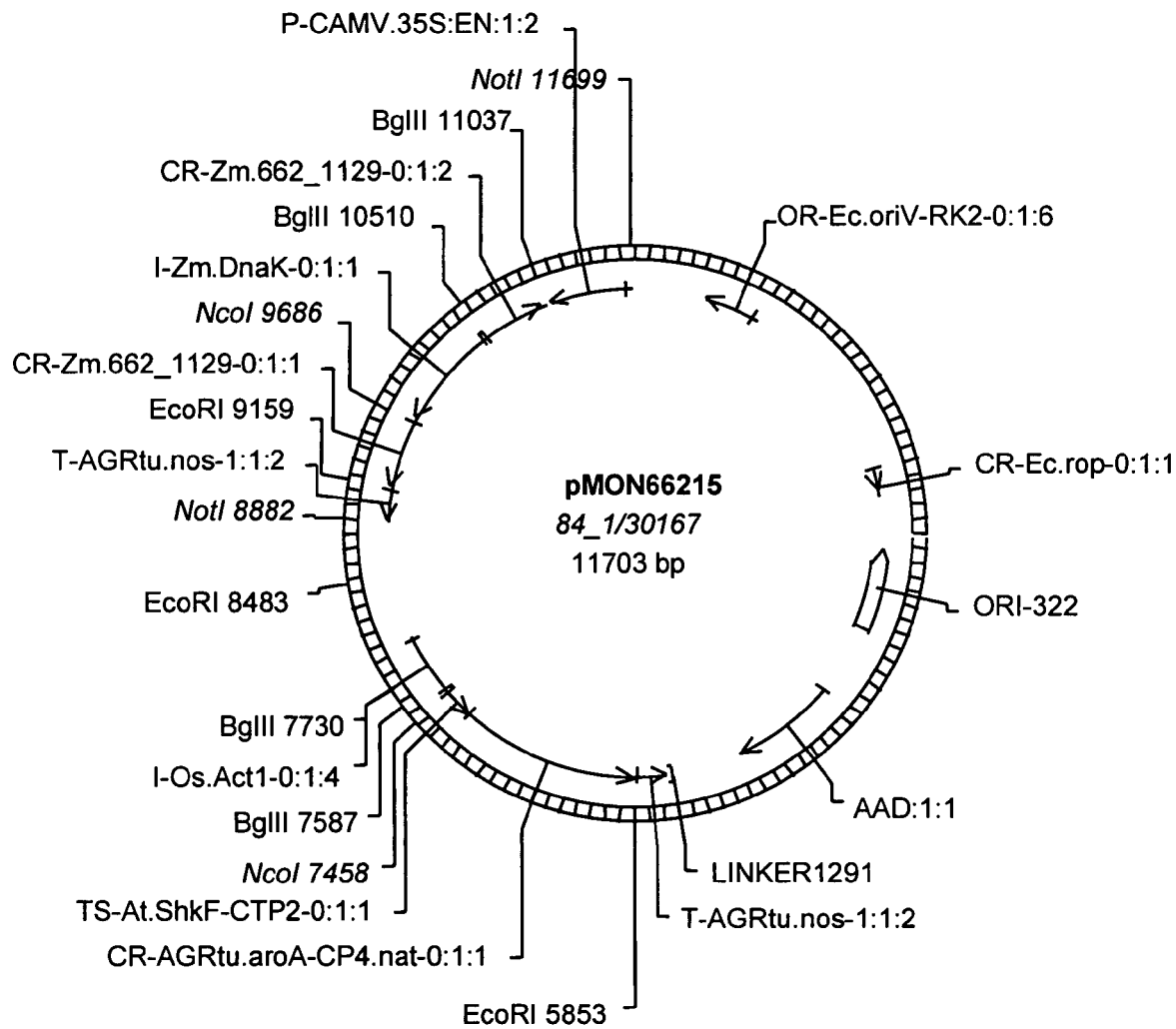
FIG. 3 is a diagram of the physical map of plasmid pMON66215.

A third plasmid was also prepared, namely pMON66215 (FIG. 3), which contains an dsRNA cassette against corn homologue cluster 84_1 (SEQ ID NO: 8). The same protocol as above was used for the vector construction using primers SEQ ID NOs: 39–42.

Figure 7:
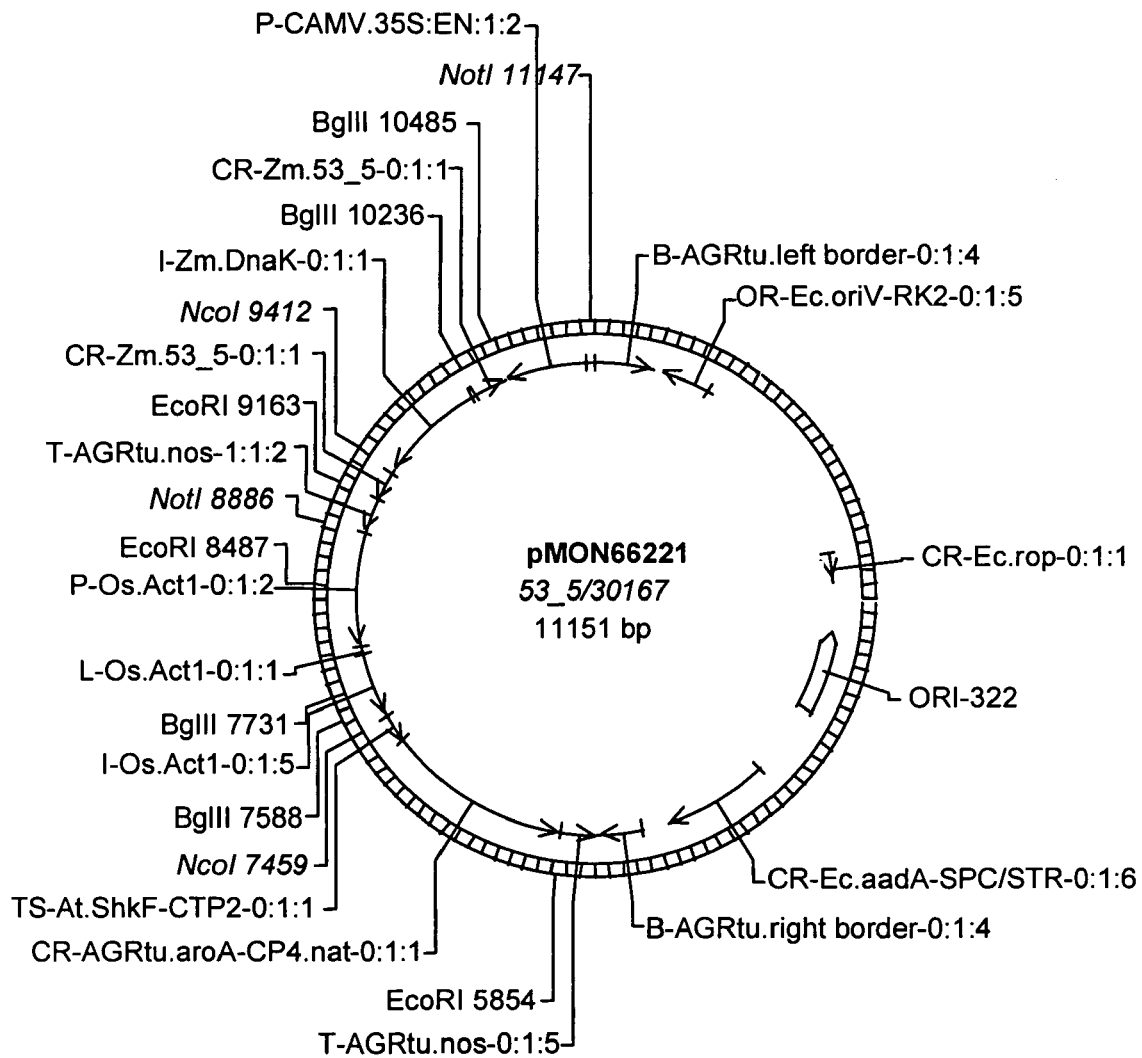
FIG. 7 is a diagram of the physical map of plasmid pMON66221.

A fourth plasmid was also prepared, namely pMON66221 (FIG. 7), which contains a dsRNA cassette against corn homologue cluster 53_5 (SEQ ID NO: 9). The same protocol as above was used for the vector construction using primers SEQ ID NOs: 43–46.

Figure 5:
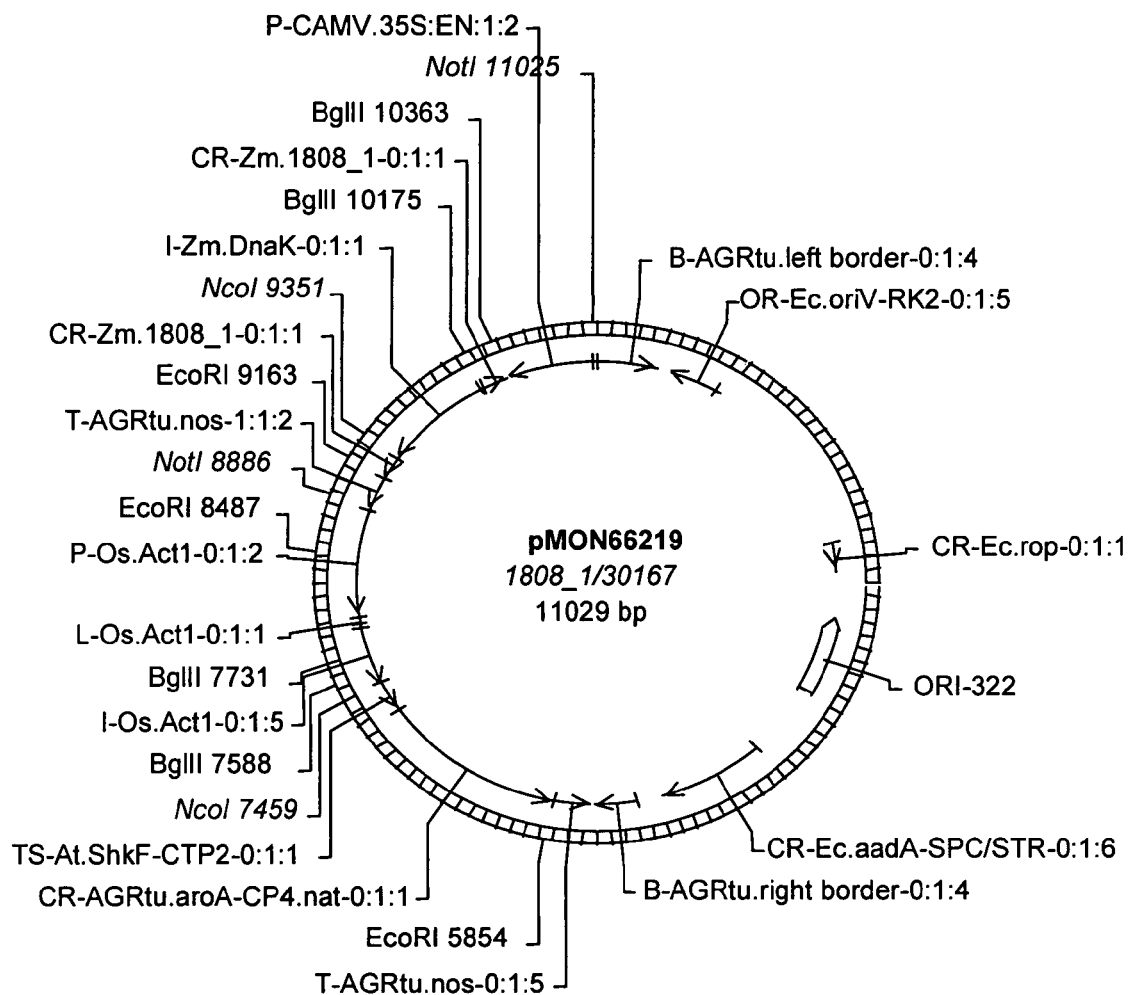
FIG. 5 is a diagram of the physical map of plasmid pMON66219.

A fifth plasmid was also prepared, namely pMON66219 (FIG. 5), which contains a dsRNA cassette against corn homologue cluster 1808_1 (SEQ ID NO: 10). The same protocol as above was used for the vector construction using primers SEQ ID NOs: 47–50.

Figure 10:
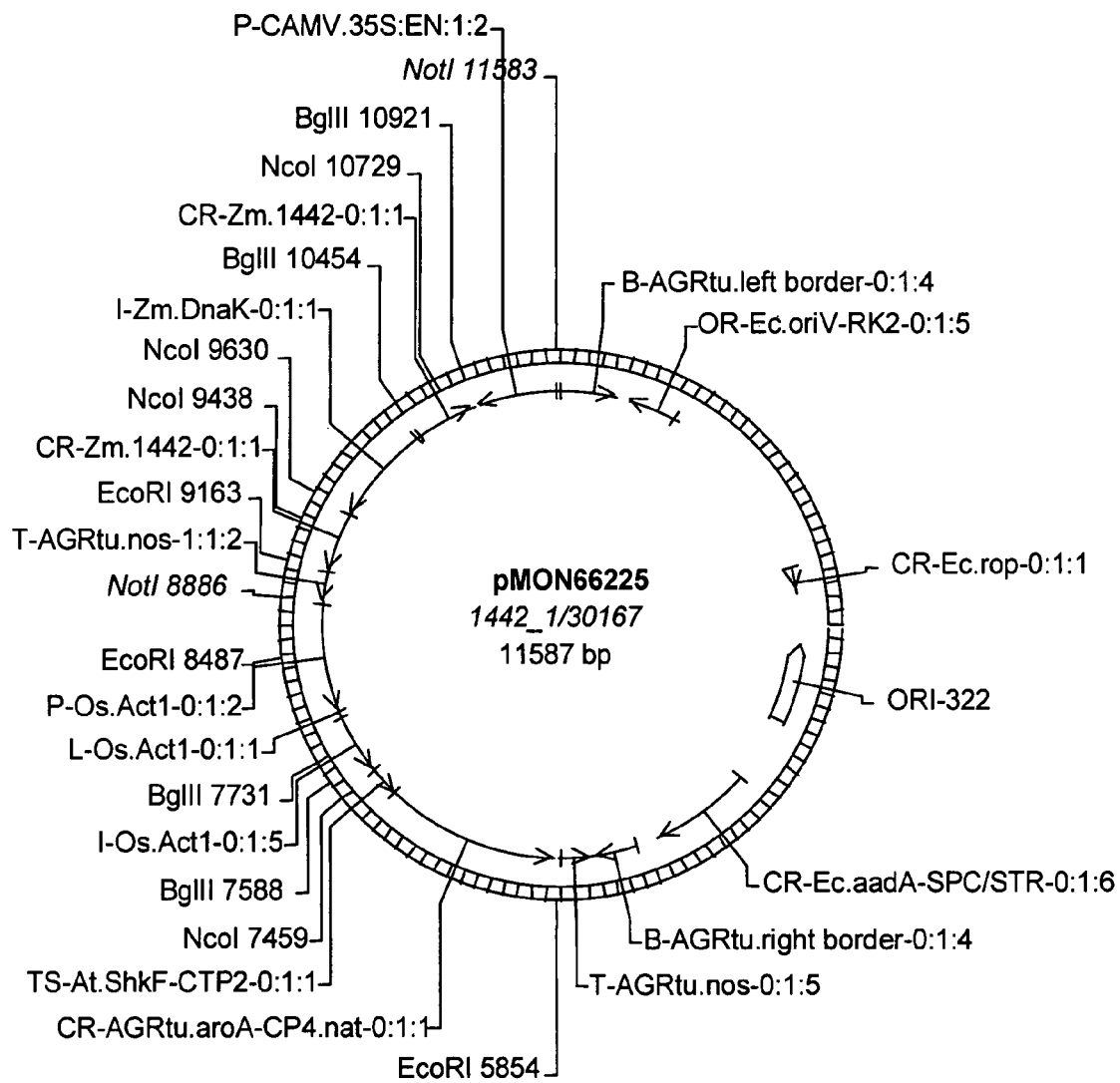
FIG. 10 is a diagram of the physical map of plasmid pMON66225.

A sixth plasmid was also prepared, namely pMON66225 (FIG. 10), which contains a dsRNA cassette against corn homologue cluster 1442_1 (SEQ ID NO: 11). The same protocol as above was used for the vector construction using primers SEQ ID NOs: 51–54.

Figure 6:
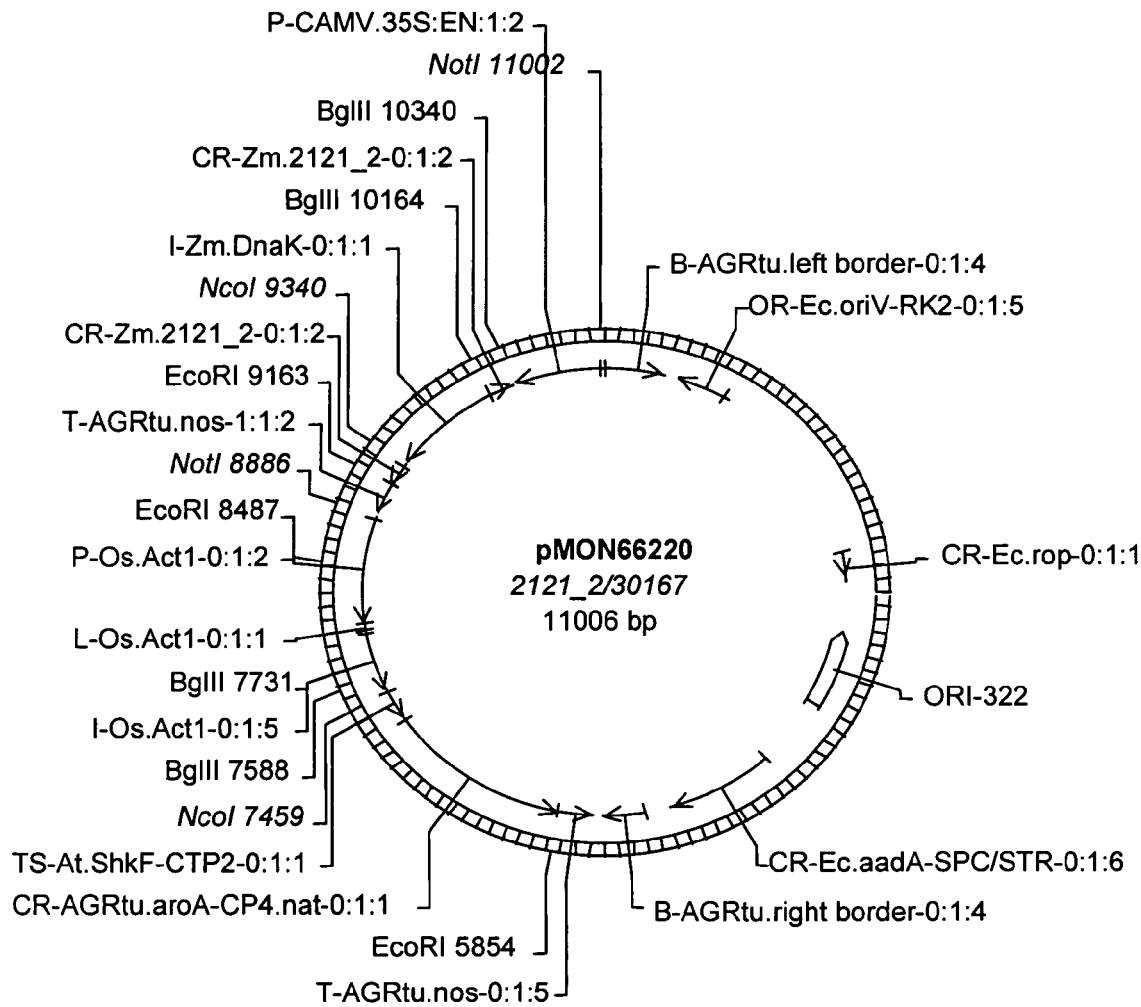
FIG. 6 is a diagram of the physical map of plasmid pMON66220.

A seventh plasmid was also prepared, namely pMON66220 (FIG. 6), which contains a dsRNA cassette against corn homologue cluster 2121_2 (SEQ ID NO: 12). The same protocol as above was used for the vector construction using primers SEQ ID NOs: 55–58.

Figure 8:
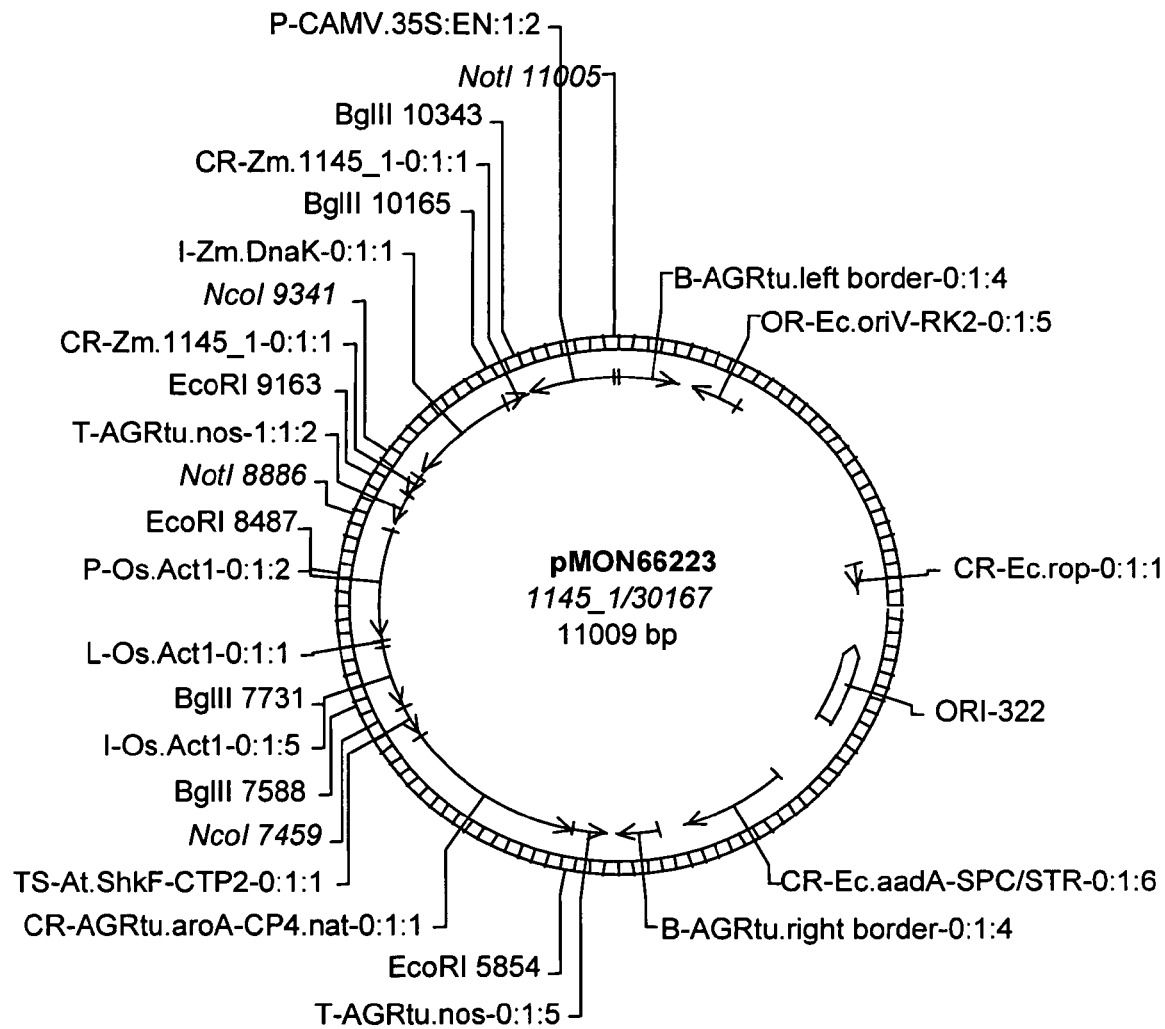
FIG. 8 is a diagram of the physical map of plasmid pMON66223.

An eighth plasmid was also prepared, namely pMON66223 (FIG. 8), which contains a dsRNA cassette against corn homologue cluster 1145_1 (SEQ ID NO: 13). The same protocol as above was used for the vector construction using primers SEQ ID NOs: 59–62.

Figure 9:
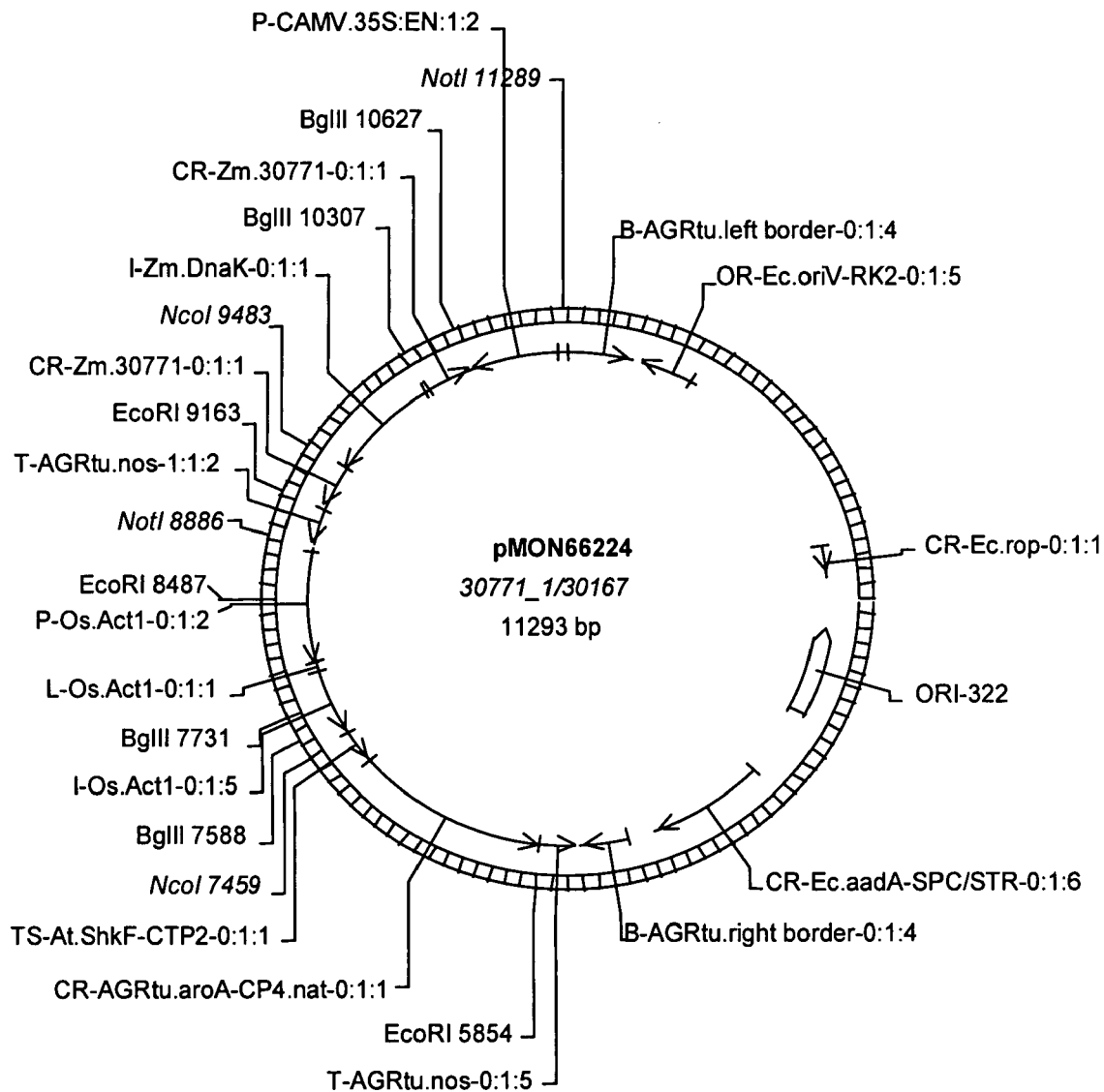
FIG. 9 is a diagram of the physical map of plasmid pMON66224.

A ninth plasmid is also prepared, namely pMON66224 (FIG. 9), which contains a dsRNA cassette against corn homologue cluster 30771_1 (SEQ ID NO: 14). The same protocol as above was used for the vector construction using primers SEQ ID NOs: 63–66.

EXAMPLE 7

This example describes the construction of plant transformation vectors useful in the present invention to provide a high protein phenotype in plants containing these constructs.

A GATEWAY™ (Invitrogen Life Technologies, Carlsbad, Calif.) transformation vector was constructed following the manufacturer's instructions or other methods known to those skilled in the art of molecular biology (Sambrook et al, supra, 2000). The elements of the plant expression vector are all known in the art and the design for which depends on the transformation technology to be deployed. Generally, the plant expression vector comprises a selectable marker expression cassette comprising a cauliflower mosaic virus 35S promoter (U.S. Pat. No. 5,352,605, incorporated herein by reference) operably linked to a gene coding neomycin phosphotransferase II (nptII) (U.S. Pat. No. 6,174,724, incorporated herein by reference). The 3' region of the selectable marker expression cassette comprises the 3' UTR region of the *Agrobacterium tumefaciens* nopaline synthase gene (NOS) followed by the 3' UTR region of the potato proteinase inhibitor II (pinII) gene (An et al., *Plant Cell*, 1:115–122 (1989)). The vector further comprises a plant expression cassette into which an AGL11 gene, or homolog, or fragment thereof, of the present invention is inserted in sense or antisense orientation, using the GATEWAY™ cloning methods. The expression cassette contains a rice actin 1 promoter and intron (U.S. Pat. No. 5,641,876, incorporated herein by reference) and the 3' termination region of the potato pinII gene. Using GATEWAY™ methods, the AGL11 gene or homologs, or fragment thereof inserted into the expression cassette. This vector is particularly useful in methods of plant transformation via direct DNA delivery, such as microprojectile bombardment.

A separate vector is constructed for use in *Agrobacterium tumefaciens*-mediated methods of transformation. This vector has all the same components as described above, but additionally has left and right T-DNA border sequence from *Agrobacterium* added to the plasmid. The right T-DNA border sequence is located 5' to the rice actin 1 promoter and the left border sequence located 3' to the nptII gene. Furthermore, it also contains a backbone comprising an ori V wide host range origin of replication functional in *Agrobacterium*, the rop sequence (the coding sequence for repressors of primer proteins for maintenance of copy number in *E. coli*), a pBR322 origin of replication functional in *E. coli*, and a spectinomycin/streptomycin resistance gene for selection for the presence of the plasmid in both *E. coli* and *Agrobacterium*.

Several different classes of constructs are contemplated in the context of the present invention, wherein the AGL11 homologs are mutated or modified including but not limited to: (1) deletion or inactivation of the DNA-binding domain, which proteins are able to dimerize with their native full length counterparts as well as other natural dimerization partners; (2) removal of the C-terminal domain, to allow dimerization with both the native protein and its natural dimerization partners; and (3) removal of both the K-box and C-terminal region.

Four constructs were built for each target gene: (1) Full length open reading frame (FLORF); (2) N-terminal truncation lacking MADS-box; (3) C-terminal truncation lacking C-terminal region; and (4) C-terminal truncation lacking K-box and C-terminal region.

Figure 11:
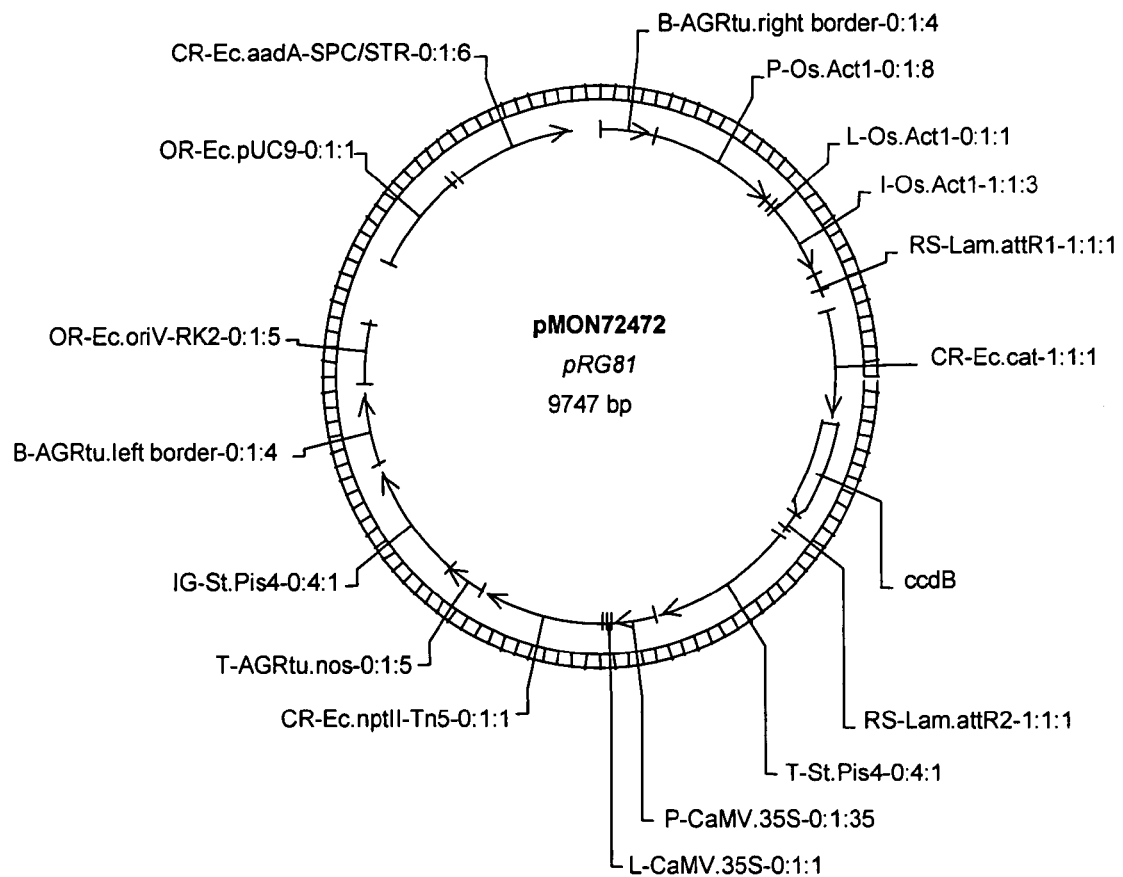
FIG. 11 is a diagram of the physical map of plasmid pMON72472.
Figure 12:
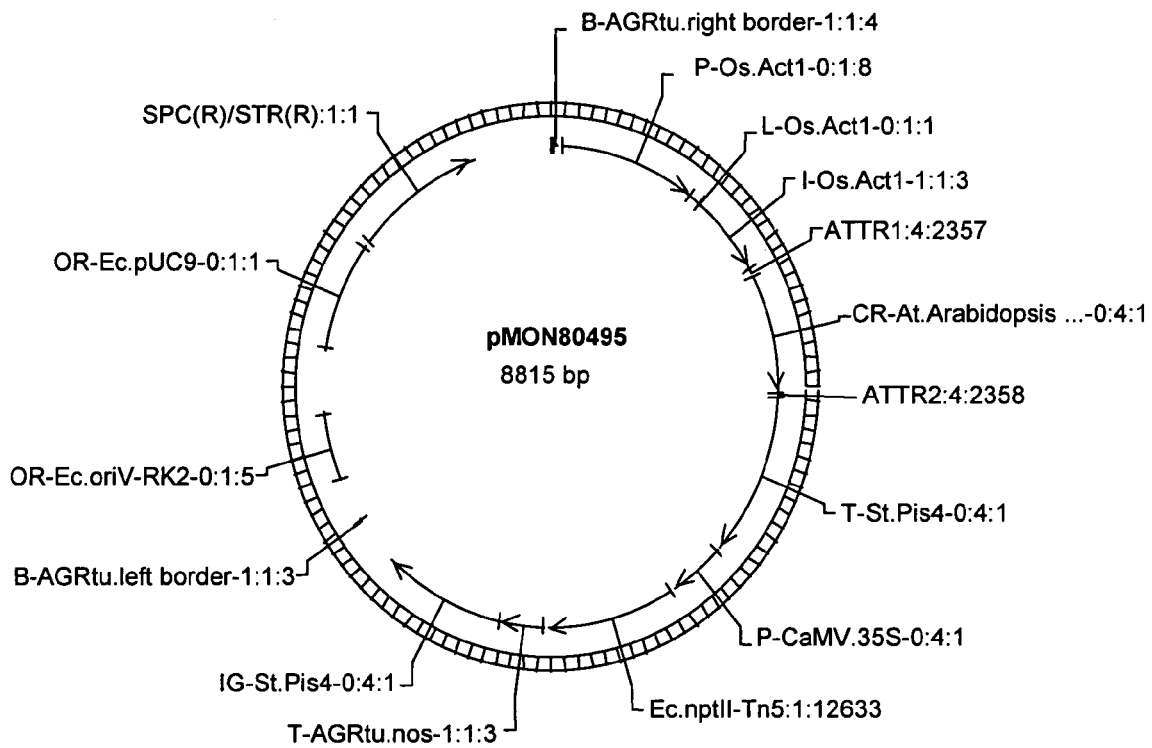
FIG. 12 is a diagram of the physical map of plasmid pMON80495.
Figure 13:
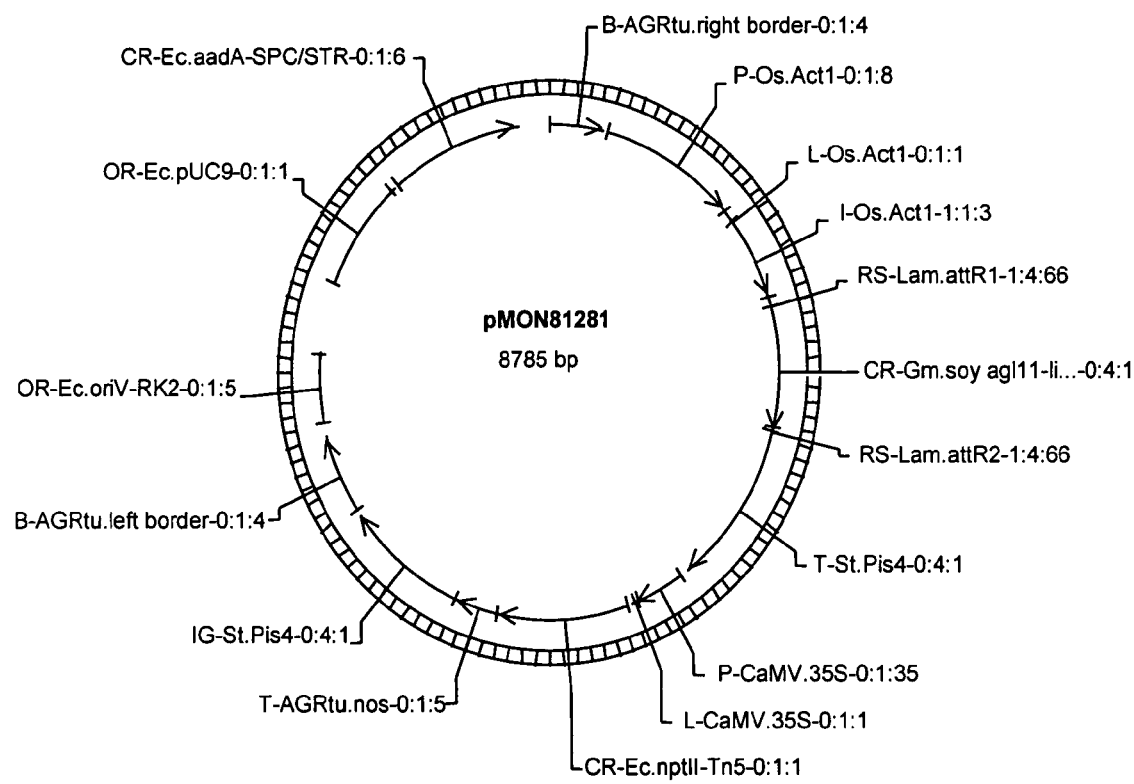
FIG. 13 is a diagram of the physical map of plasmid pMON81281.
Figure 14:
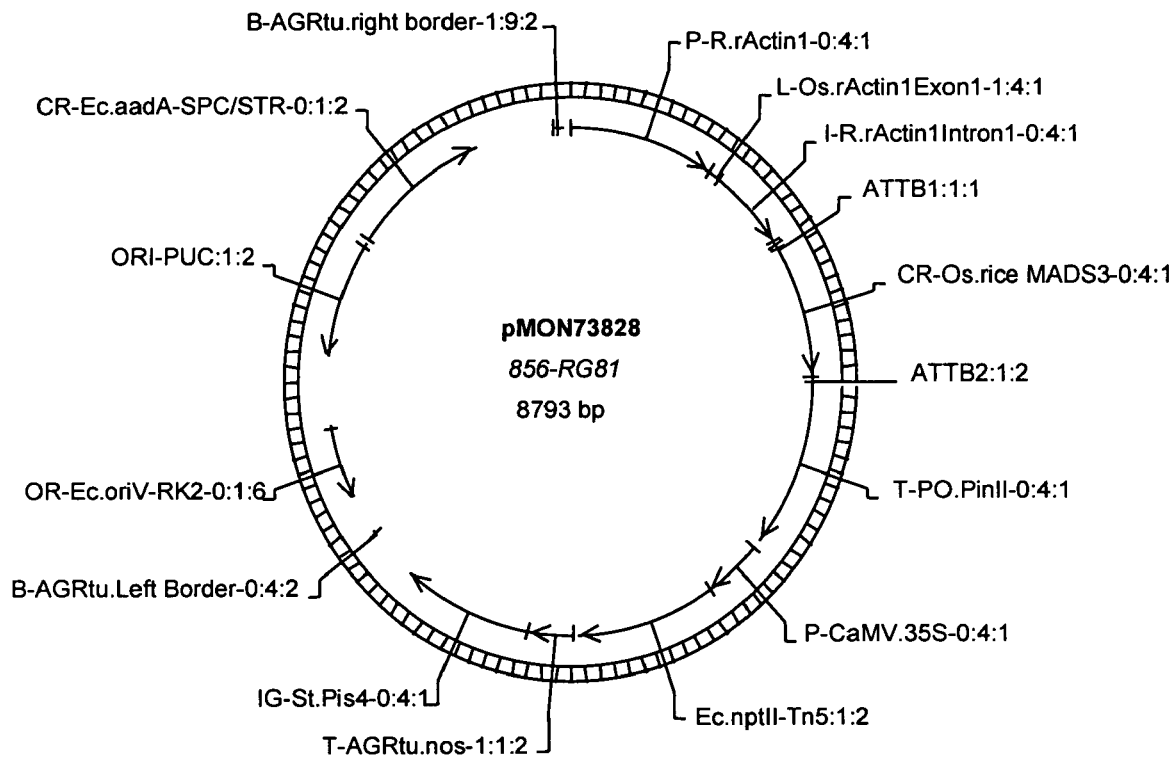
FIG. 14 is a diagram of the physical map of plasmid pMON73828.

Construction of the full-length open reading frame (FLORF) constructs was completed as follows. For the *Arabidopsis* FLORF, bases 1–690 of SEQ ID NO: 67 were cloned, using standard protocols as described above, into the base binary vector pMON72472 (FIG. 11) at the GATEWAY™ site to create plant transformation vector pMON80495 (FIG. 12). The binary vector uses the rice actin promoter and intron to drive its expression. For the soybean FLORF, bases 82–747 of SEQ ID NO: 68 were cloned, using standard protocols as described above, into pMON72472 at the GATEWAY™ site to create plant transformation vector pMON81281 (FIG. 13). For the maize FLORF, bases 96–899 of SEQ ID NO: 69 were cloned, using standard protocols as described above, into the base binary vector pMON72472 (FIG. 11) at the GATEWAY™ site to create the plant transformation vector. For the rice FLORF, bases 235–945 of SEQ ID NO: 70 were cloned, using standard protocols as described above, into pMON72472 to create plant transformation vector pMON73828 (FIG. 14).

Figure 15:
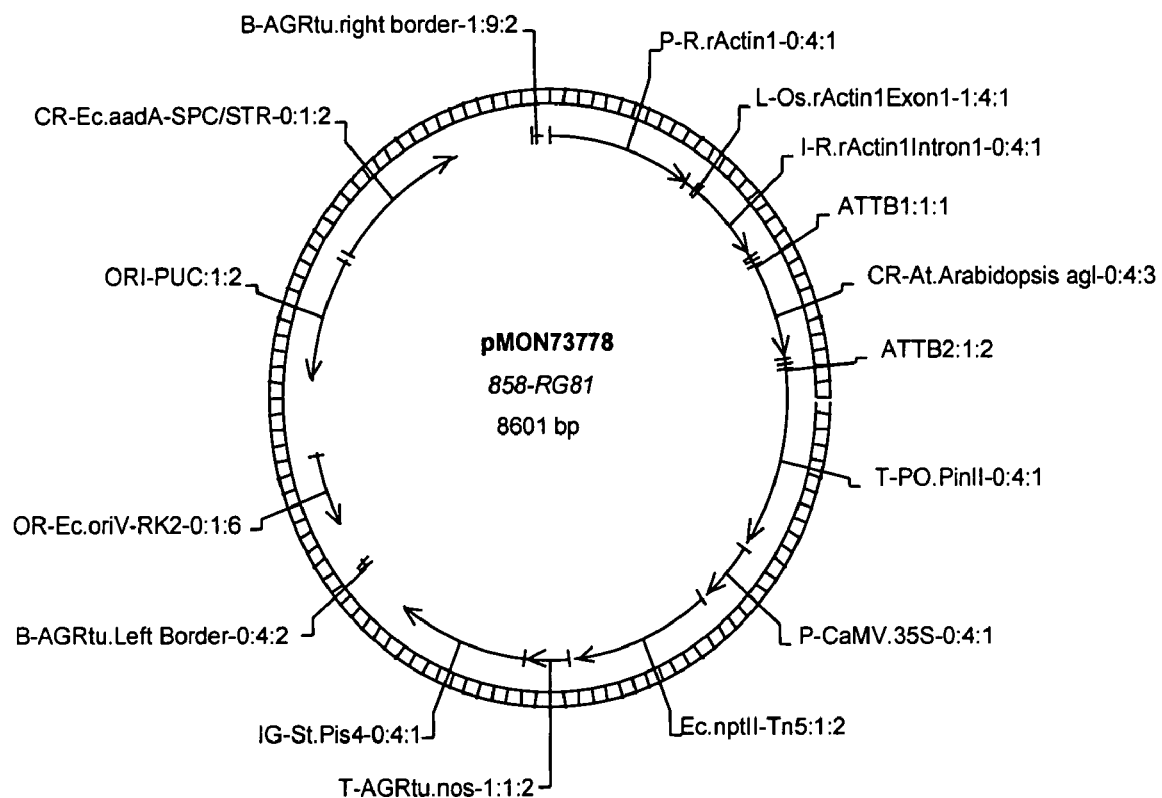
FIG. 15 is a diagram of the physical map of plasmid pMON73778.
Figure 16:
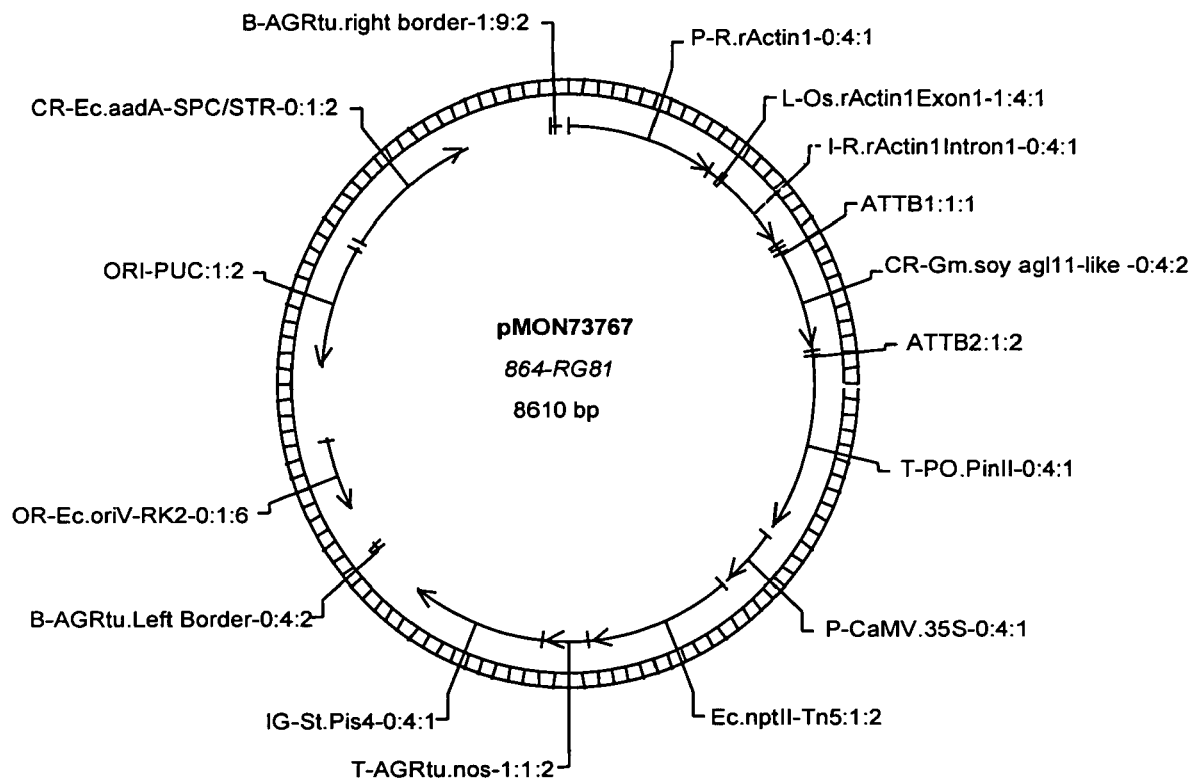
FIG. 16 is a diagram of the physical map of plasmid pMON73767.
Figure 17:
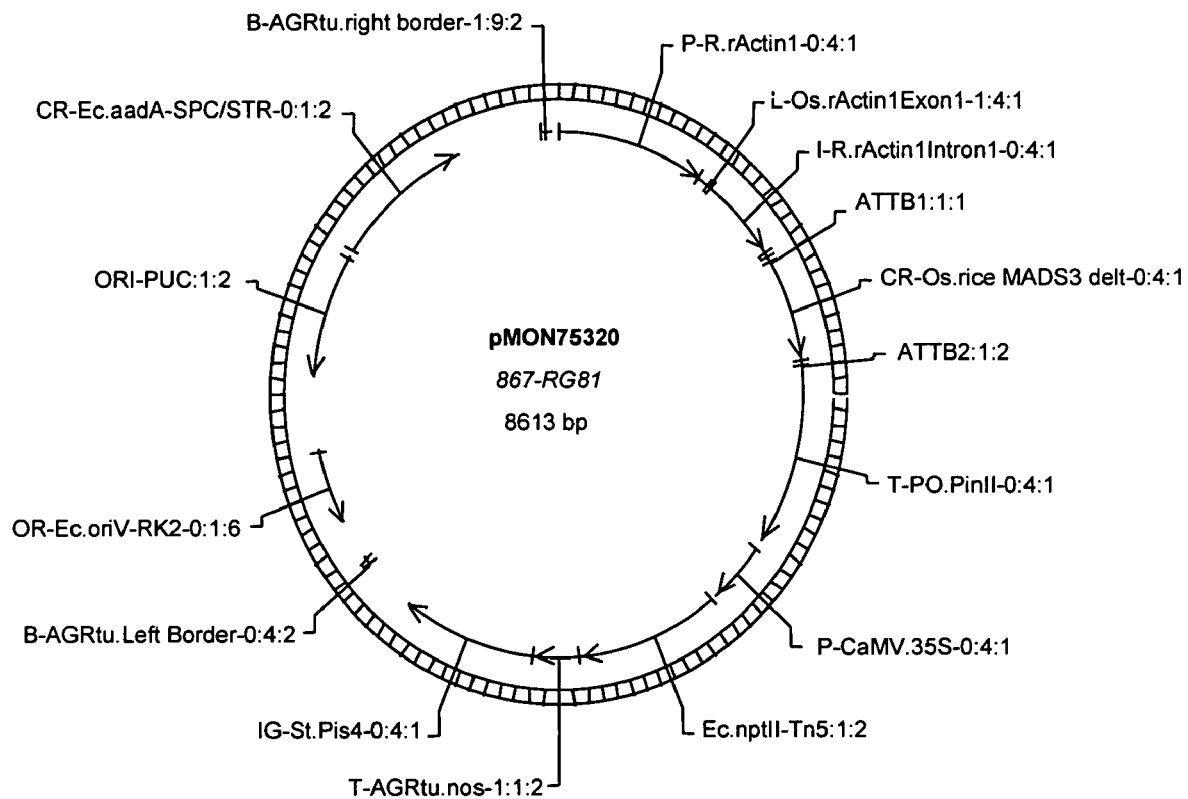
FIG. 17 is a diagram of the physical map of plasmid pMON75320.

Construction of the truncated protein encoding DNA constructs used in the present invention was completed as follows. For the *Arabidopsis* C-terminal truncation, bases 1–519 of SEQ ID NO: 67 were cloned into pMON72472 at the GATEWAY™ site to create plant transformation vector pMON73778 (FIG. 15). For the soybean C-terminal truncation, bases 1–528 of SEQ ID NO: 68 were cloned into pMON72472 at the GATEWAY™ site to create plant transformation vector pMON73767 (FIG. 16). For the maize C-terminal truncation, bases 1–531 of SEQ ID NO: 69 were cloned into pMON72472 at the GATEWAY™ site to create the plant transformation vector. For the rice C-terminal truncation, bases 1–531 of SEQ ID NO: 70 were cloned into pMON72472 at the GATEWAY™ site to create plant transformation vector pMON75320 (FIG. 17).

Figure 18:
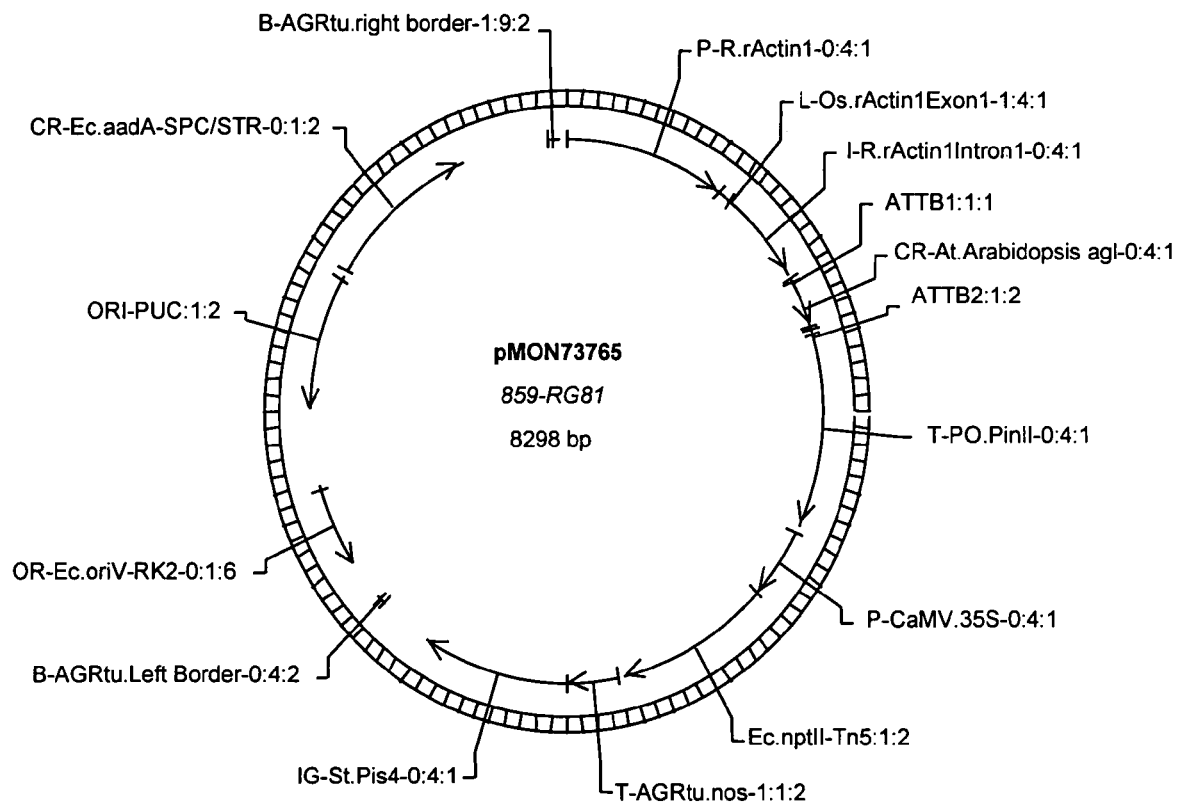
FIG. 18 is a diagram of the physical map of plasmid pMON73765.
Figure 19:
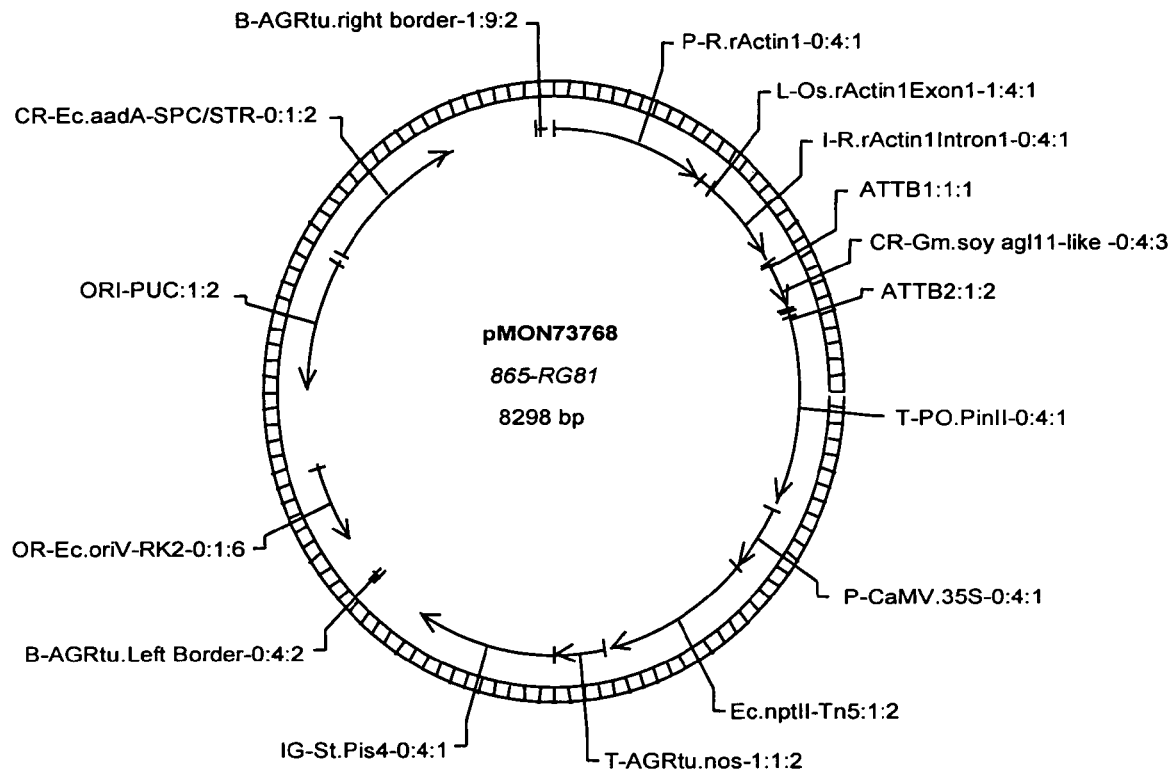
FIG. 19 is a diagram of the physical map of plasmid pMON73768.
Figure 20:
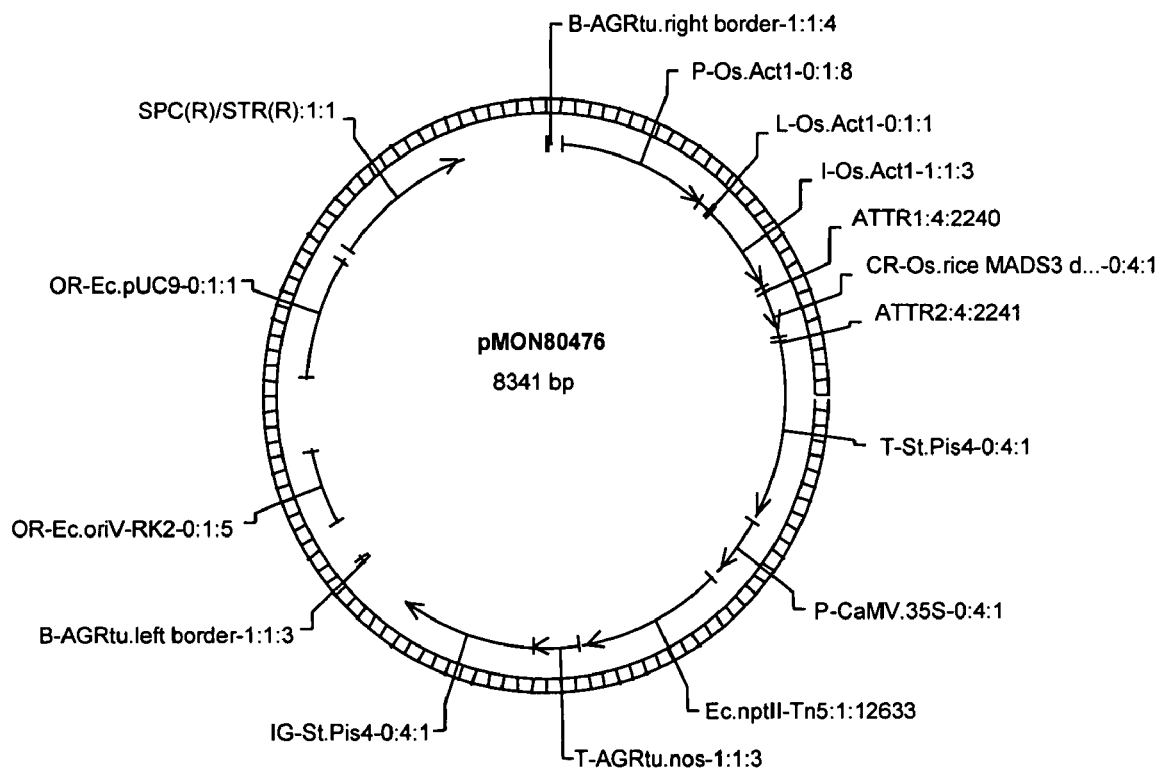
FIG. 20 is a diagram of the physical map of plasmid pMON80476.

For the *Arabidopsis* K-box truncation, bases 1–216 of SEQ ID NO: 67 were cloned into pMON72472, at the GATEWAY™ site to create plant transformation vector pMON73765 (FIG. 18). For the soybean K-box truncation, bases 1–216 of SEQ ID NO: 68 were cloned into pMON72472 at the GATEWAY™ site to create plant transformation vector pMON73768 (FIG. 19). For the maize K-box truncation, bases 1–216 of SEQ ID NO: 69 were cloned into pMON72472 at the GATEWAY™ site to create the plant transformation vector. For the rice K-box truncation, bases 1–216 of SEQ ID NO: 70 were cloned into pMON72472 at the GATEWAY™ site to create plant transformation vector pMON80476 (FIG. 20).

Figure 21:
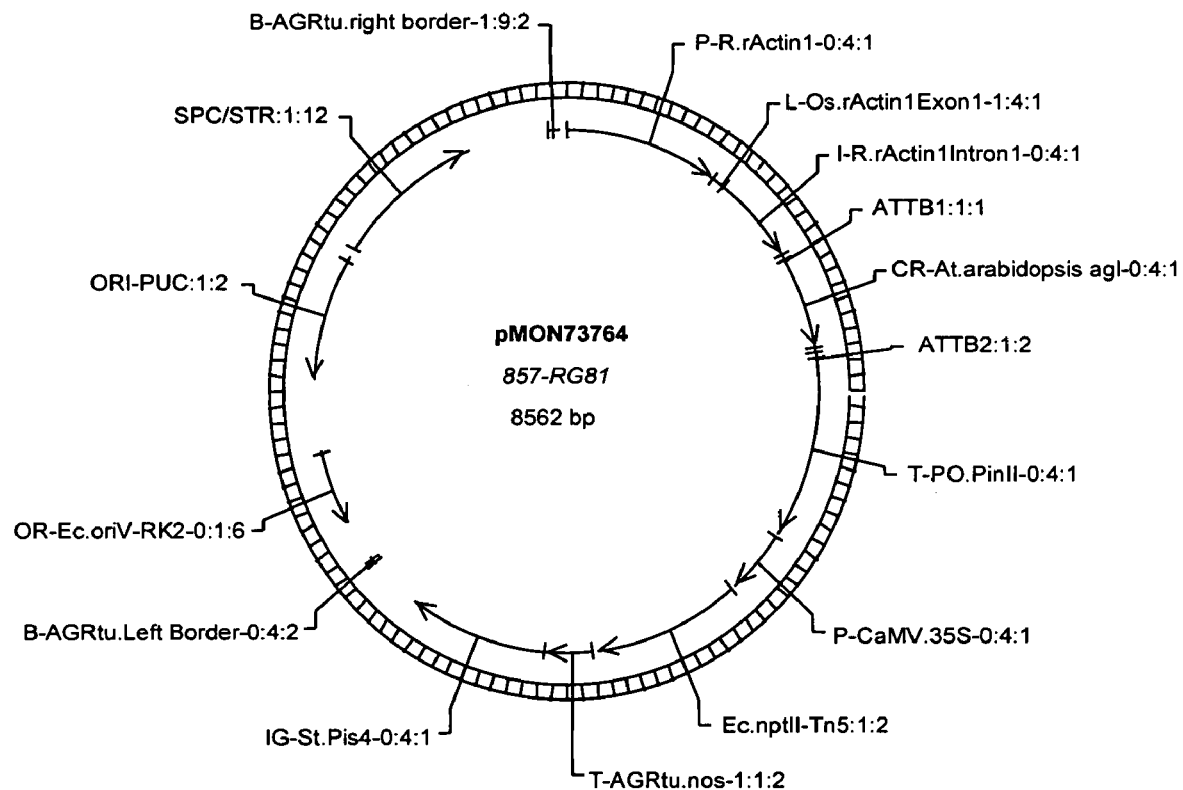
FIG. 21 is a diagram of the physical map of plasmid pMON73764.
Figure 22:
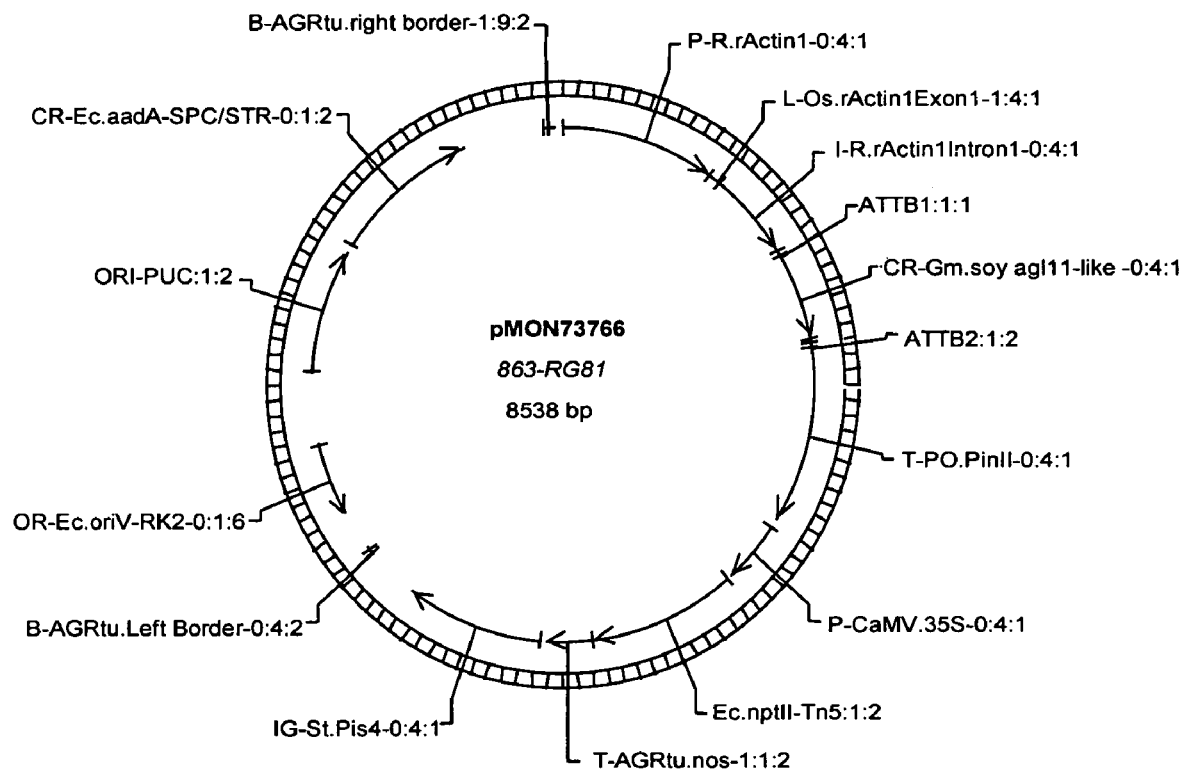
FIG. 22 is a diagram of the physical map of plasmid pMON73766.
Figure 23:
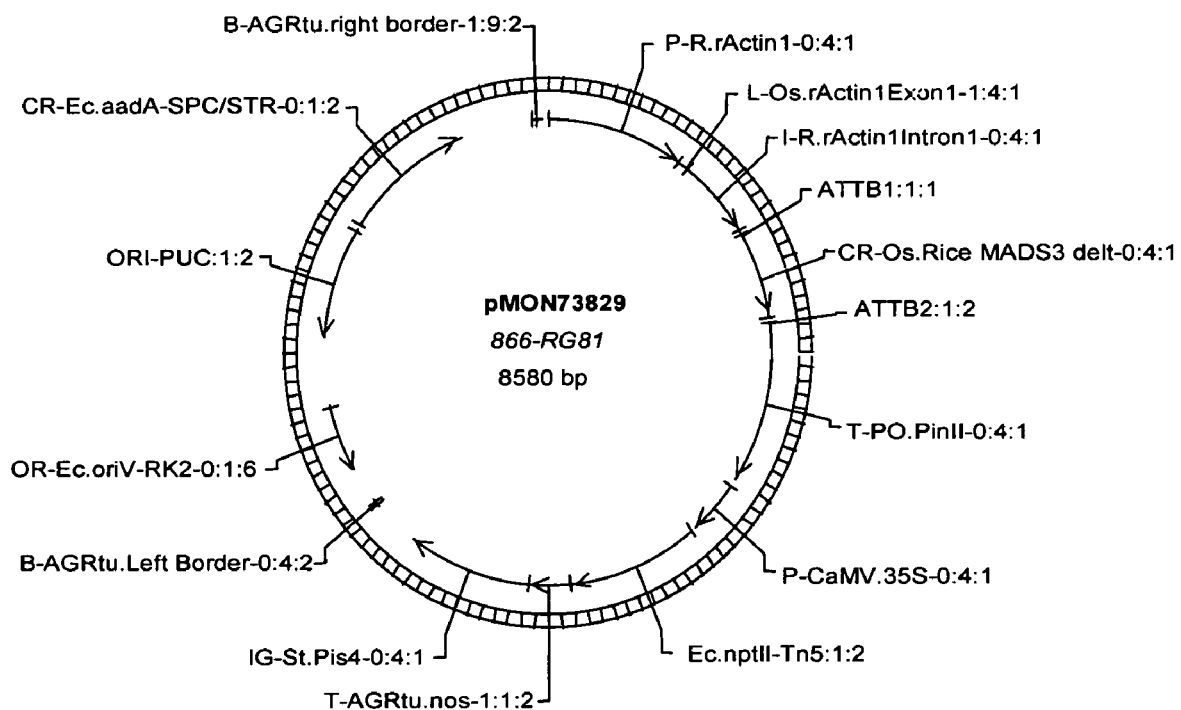
FIG. 23 is a diagram of the physical map of plasmid pMON73829.

The delta MADS-box constructs were created by deletion of the MADS-box domain of the MADS-box protein with addition of the ATG start codon to the remaining fragment and cloning the piece into the GATEWAY™ site of pMON72472 as described for the FLORFs. For the *Arabidopsis* MADS-box truncation, bases 210–690 of SEQ ID NO: 67 were cloned into pMON72472 at the GATEWAY™ site to create plant transformation vector pMON73764 (FIG. 21). For the soybean MADS-box truncation, bases 294–747 of SEQ ID NO: 68 were cloned into pMON72472 at the GATEWAY™ site to create plant transformation vector pMON73766 (FIG. 22). For the maize MADS-box truncation, bases 275–899 of SEQ ID NO: 69 were cloned into pMON72472 at the GATEWAY™ site to create the plant transformation vector. For the rice MADS-box truncation, bases 447–945 of SEQ ID NO: 70 were cloned into pMON72472 at the GATEWAY™ site to create vector pMON73829 (FIG. 23) for transformation.

EXAMPLE 8

This example describes the identification of AGL11 homologs in soybean, maize, and rice.

Using the AGL11 sequence from *Arabidopsis thaliana* (SEQ ID NO: 6), a sequence database was searched using a standard BLAST program, namely TBLASTX 2.0.12 (Altschul et al., *Nucleic Acids Res.*, 25:3389–3402 (1997)), using a cutoff value of $10^{-8}$. The soybean, maize, and rice homologs identified by this search were SEQ ID NO: 68, SEQ ID NO: 69, and SEQ ID NO: 70, respectively.

The various constructs set forth herein above are used to transform plants, and their propagation effects on protein and oil content of seed is tested.

EXAMPLE 9

This example describes the transformation of maize immature embryos using an *Agrobacterium tumefaciens*—mediated transformation protocol.

Corn plants (inbred line LH59) are grown in the greenhouse under standard practices. The ears of the plants are harvested when the embryos are 1.5 to 2.0 mm in length, usually 10–15 days after pollination. The ears are surface sterilized by spraying or soaking them in 80% ethanol.

The immature embryos are isolated from individual seeds using methods known to those of skill in the art. Immature embryos are cultured on medium 211 (N6 salts, 2% sucrose, 1 mg/L 2,4-dichlorophenyoxyacetic acid (2,4-D), 0.5 mg/L niacin, 1.0 mg/L thiamine-HCl, 0.91 g/L L-asparagine, 100 mg/L myo-inositol, 0.5 g/L MES, 100 mg/L casein hydrolysate, 1.6 g/L MgCl2, 0.69 g/L L-proline, 2 g/L GELGRO™, pH 5.8) containing 16.9 mg/L AgNO3 (designated medium 2112V) for 3–6 days prior to transformation.

Methods of *Agrobacterium*-mediated transformation of maize cells and other monocots are known (U.S. Pat. Nos. 5,591,616 and 5,981,840; incorporated herein by reference). The *Agrobacterium* strain ABI (Koncz and Schell, *Molecular and General Genetics*, 204(3):383–96 (1986)), and an *Agrobacterium tumefaciens* binary vector system are used for the transformations.

Prior to co-culture with the maize embryo cells, *Agrobacterium* cells are grown at 28° C. in Luria broth ("LB" a DIFCO product) liquid medium containing approximately 50 μg/ml kanamycin and 100 μg/ml spectinomycin to select for maintenance of the modified Ti plasmid and binary vector. Prior to inoculation of maize cells, the *Agrobacterium* cells are grown overnight at room temperature in AB medium (Chilton et al., *Proc. Nat. Acad. Sci.* (U.S.A.), 71:3672–3676 (1974)) comprising appropriate antibiotics for plasmid maintenance and 200 μM acetosyringone. Immediately prior to inoculation the *Agrobacterium* cells are pelleted by centrifugation, washed in ½ MSVI medium (defined as: 2.2 g/L GIBCO MS basal salts (Murashige and Skoog, *Physiol. Plant*, 15:473–497 (1962)), 2 mg/L glycine, 0.5 g/L niacin, 0.5 g/L L-pyridoxin-HCl, 0.1 mg/L thiamine, 115 g/L L-proline, 10 g/L D-glucose, and 10 g/L sucrose, pH 5.4) containing 200 μM acetosyringone.

The immature maize embryos described above, are excised and immersed in an *Agrobacterium* suspension in ½ MSPL medium (defined as: 2.2 g/L MS salt (Murashige and Skoog, supra) 1 mL of a 1000× stock of MS vitamins (Murashige and Skoog, supra), 115 mg/L proline, 26 g/L glucose, 68.5 g/L sucrose). The embryos are then incubated at room temperature with *Agrobacterium* for approximately 5 minutes.

Following *Agrobacterium* infection and co-culture, the embryos are transferred to delay medium for 5 to 7 days and cultured at 27° C. in the dark. Delay medium consists of MS basal salts containing 2.0 mg/L 2,4-D (GIBCO), 100 mg/L-casamino acids, 12 mM proline, 500 mg/L carbenicillin, and 20 μM silver thiosulfate. Once signs of type II callus initiation from immature embryos are observed, as defined by Selman et al. (*In The Maize Handbook*, Freeling and Walbot, eds., Springer Verlag, p. 672 (1994)), the coleoptiles are removed from the embryos. The embryos are then transferred to MS medium containing 2.0 mg/L 2,4-D, 12 mM proline, 20 μM silver thiosulfate, 500 mg/L carbenicillin, and 0.5 mM glyphosate and incubated at 27° C. in the dark for 2 weeks.

Embryos forming callus are transferred to the MS medium described above, but additionally containing 1.0 mM glyphosate. The cultures were then incubated for 2 weeks in the dark at 27° C. The embryos still having callus were then transferred to MS medium containing 3.0 mM glyphosate for an additional 2 weeks.

Plant regeneration was achieved by transferring the callus to MS medium containing 0.1 mg/L 2,4-D and 0.1 μM abscisic acid (ABA) for 2 weeks and then to MS medium containing 6% sucrose and no 2,4-D for another 2 weeks. Both incubations were done in the dark at 27° C. to permit somatic embryo maturation and conversion in the regeneration process.

Somatic embryos that are ready to germinate are transferred to hormone-free MS medium, and incubated in the light until shoots with attached roots are produced. After approximately 2 to 3 weeks, plantlets are produced.

Plantlets are then transferred to the greenhouse and grown under standard greenhouse conditions.

EXAMPLE 10

This example describes the analysis of transgene expression and seed protein levels in transformed maize plants.

For seed protein analysis, small bulk samples consisting of 30–50 seeds for each treatment were measured using near infrared reflectance spectroscopy in accordance with the method set forth at Example 2. Prior to analyzing unknown samples, spectral data was collected with calibration samples that were subsequently analyzed using a primary analysis technique. The primary technique used was nitrogen combustion as described by Galbiati et al. (*Funct. Integr. Genomics*, 1:25–34 (2000)). A multivariate model was developed using the spectral data from the spectrometer and the primary data. In the present case a PLS-1 (Partial Least Squares Regression Type I) multivariate model was constructed using 152 calibration samples. Each unknown sample was scanned on the spectrometer at least 5 times and its protein content predicted with each scan. Each time the sample was scanned it was added back to the sample cuvette to minimize multiplicative scattering effects, which are not correlated to a chemical property of interest. The predicted protein is averaged for the multiple scans and then reported for each sample.

EXAMPLE 11

This illustrates the cloning of the AGL11 promoter from *Arabidopsis thaliana*.

Figure 24:
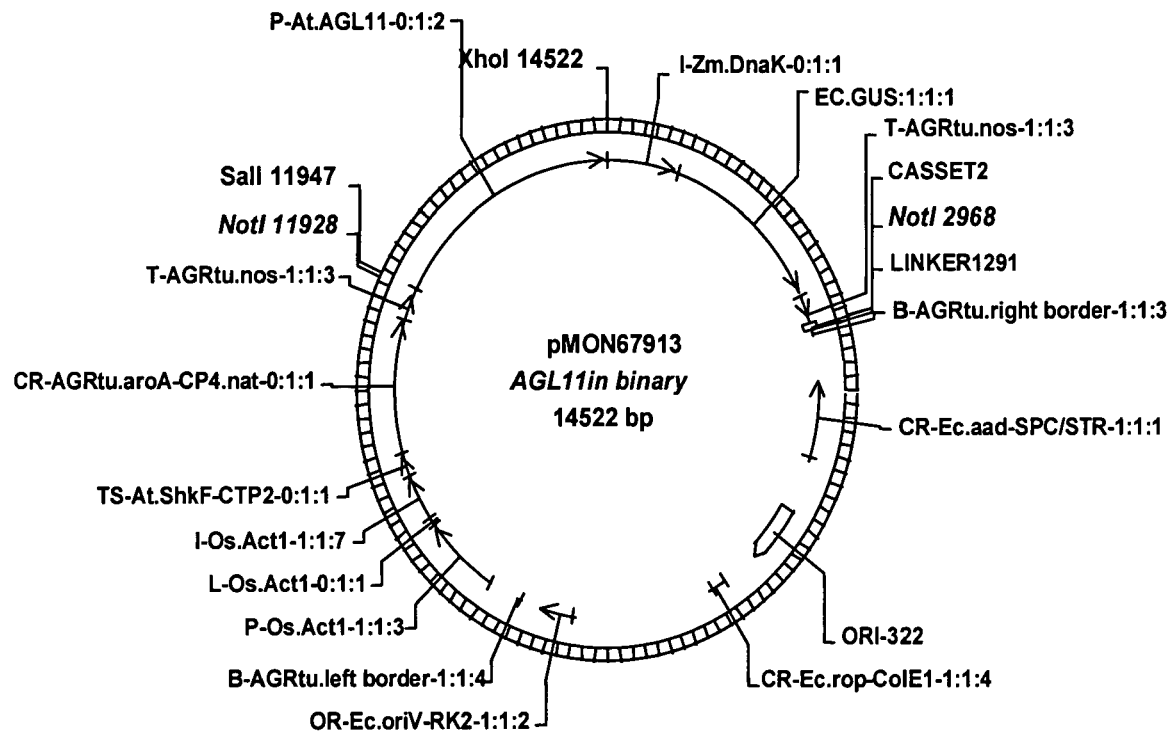
FIG. 24 is a diagram of the physical map of plasmid pMON67913.
Figure 25:
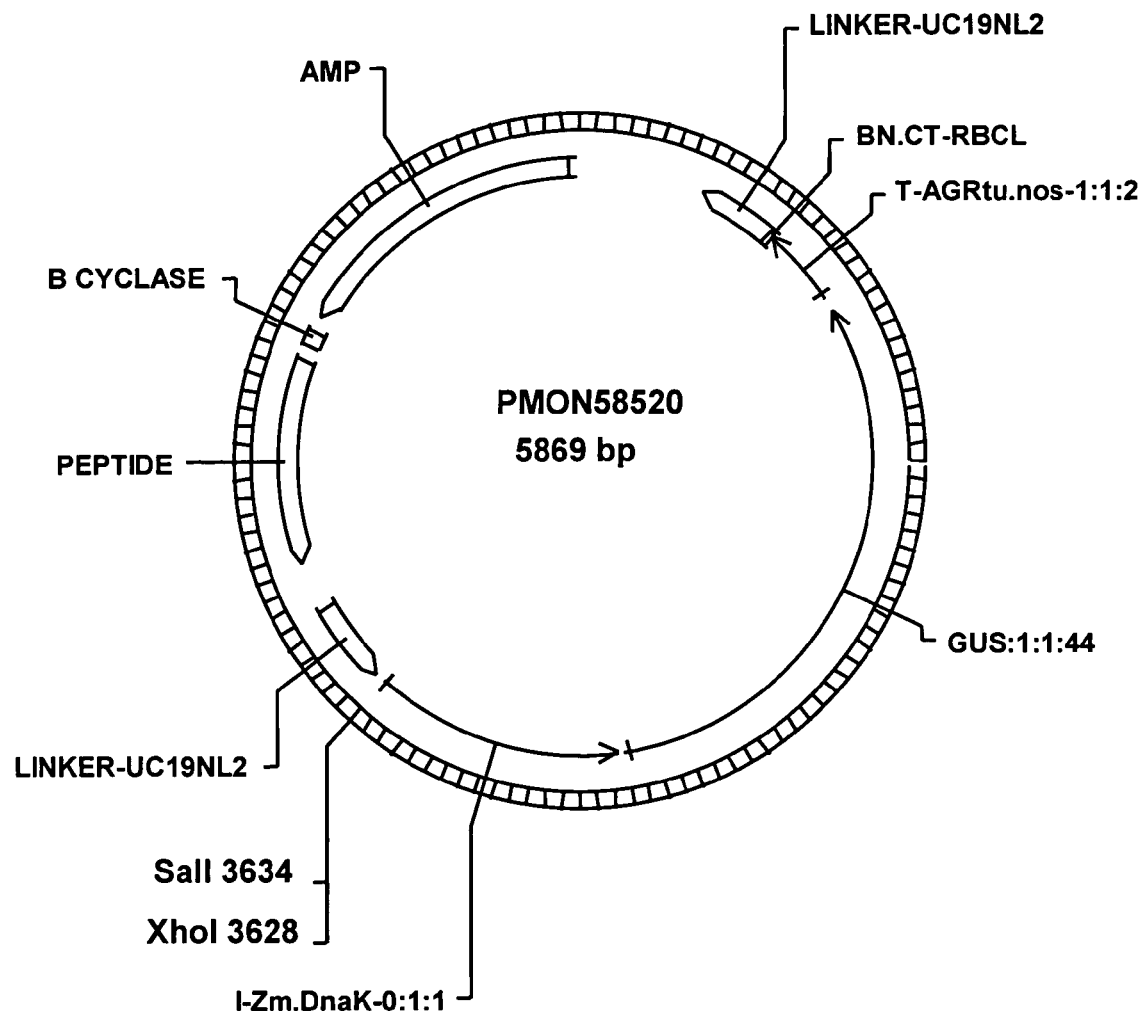
FIG. 25 is a diagram of the physical map of plasmid pMON58520.

The AGL11 promoter was isolated by PCR amplification of a 2 kb region of genomic DNA upstream of the AGL11 ATG start site. The plasmid pMON67913 (FIG. 24) contains an *Arabidopsis* AGL11 promoter cassette expressing GUS. Primers AGL11 saiI (SEQ ID NO: 71) and AGL11 xhoI (SEQ ID NO: 72) were used to PCR the AGL11 promoter using genomic DNA isolated from *Arabidopsis thaliana*. The PCR product (SEQ ID NO: 73) was inserted between the salI and xhoi sites of pMON58520 (FIG. 25), resulting in the generation of plasmid pMON67913. A similar process can isolate promoters from AGL11 homologues.

Having illustrated and described the principles of the present invention, it should be apparent to persons skilled in the art that the present invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

We claim:

1. A method of altering the nitrogen or oil content of a seed of a transgenic plant comprising suppressing transcription of an AGL11 gene and/or accumulation of an AGL11 mRNA transcript wherein the nitrogen content of the seed of the transgenic plant is increased and/or the oil content of the seed of the transgenic plant is decreased as compared to a seed from a plant of the same laboratory or field stock without such suppression.

2. The method of claim 1 wherein the concentration of an AGL11 gene product is downregulated by introduction of a transformation vector that produces RNA capable of duplex formation with a transcript thereof, and wherein the nitrogen content of the seed is increased.

3. The method of claim 1, wherein suppressing transcription of an AGL11 gene and/or accumulation of AGL11 mRNA is accomplished by insertional mutagenesis.

4. The method of claim 1, wherein suppressing transcription of an AGL11 gene and/or accumulation of AGL11 mRNA is accomplished by anti-sense suppression.

5. The method of claim 1, wherein suppressing transcription of an AGL11 gene and/or accumulation of AGL11 mRNA is accomplished by co-suppression.

6. The method of claim 1, wherein suppressing transcription of an AGL11 gene and/or accumulation of AGL11 mRNA is accomplished by RNA interference.

* * * * *

SEQUENCE LISTING

<160> NUMBER OF SEQ ID NOS: 73

<210> SEQ ID NO 1
<211> LENGTH: 27
<212> TYPE: DNA
<213> ORGANISM: Artificial sequence
<220> FEATURE:
<223> OTHER INFORMATION: Fully synthetic sequence

<400> SEQUENCE: 1
cgtccatact ggaatagtgg ggatcct                                27

<210> SEQ ID NO 2
<211> LENGTH: 22
<212> TYPE: DNA
<213> ORGANISM: Artificial sequence
<220> FEATURE:
<223> OTHER INFORMATION: Fully synthetic sequence

<400> SEQUENCE: 2
gtaatacgac tcactatagg gc                                     22

<210> SEQ ID NO 3
<211> LENGTH: 27
<212> TYPE: DNA
<213> ORGANISM: Artificial sequence
<220> FEATURE:
<223> OTHER INFORMATION: Fully synthetic sequence

<400> SEQUENCE: 3
gcagactcta aatctgccgt catcgac                                27

<210> SEQ ID NO 4

-continued

```
<211> LENGTH: 19
<212> TYPE: DNA
<213> ORGANISM: Artificial sequence
<220> FEATURE:
<223> OTHER INFORMATION: Fully synthetic sequence

<400> SEQUENCE: 4
actatagggc acgcgtggt                                                    19

<210> SEQ ID NO 5
<211> LENGTH: 480
<212> TYPE: DNA
<213> ORGANISM: Artificial sequence
<220> FEATURE:
<223> OTHER INFORMATION: Fully synthetic sequence
<220> FEATURE:
<221> NAME/KEY: misc_feature
<222> LOCATION: (69)..(69)
<223> OTHER INFORMATION: n is a, c, g, or t

<400> SEQUENCE: 5
gtttcgcttc gaggttcgaa tccttccccc ccccgggatc ggcatgcaag cttagcttga        60
gcttggatng attgtcgttt cccgccttca gtttaaacta tcagtgttta aaacagcatg       120
agttgctttt agttgaaatc gaaaacgcgc agaaagggt aagcaaagct caagttggtt       180
gctctaaatt ttaattgtgt gaatctttga atatggtata gttaattttg caggagattg      240
agcttgacaa tgagaacatc tatctaagaa ctaaggtaat attagtgtgt gtgaagtcca      300
tagacatgtc gaatcaatca cttgttatac taatttttat gtttcttaac aggtagcaga      360
agtggagagg tatcaaccac accatcatca aatggttagt ggttcagaga ttaatgcaat      420
tgaagcttta gcctcacgca attactttgc tcatagcatt atgactgctg gttctggatc      480

<210> SEQ ID NO 6
<211> LENGTH: 905
<212> TYPE: DNA
<213> ORGANISM: Arabidopsis thaliana

<400> SEQUENCE: 6
acgagagcaa attctcagga tgggaagagg aaagatagaa ataaagagga tagagaactc        60
aacaaatcga caagtgacgt tttgcaaaag aagaaatgga cttctgaaga aagcctatga       120
gctttcggtc ctttgcgatg cagaagttgc gctcattgtt ttctccactc gtggccgtct       180
ctatgaatac gccaataaca acataagatc aaccattgag aggtacaaga agcttgttc       240 tgatagcacc aacactagca ctgtccaaga aatcaatgcc gcgtactatc aacaagaatc       300
tgctaagctg agacaacaga tccaaacgat tcaaaactcc aacaggaatc tgatgggaga       360
ctctttgagt tccttaagtg tcaaggaact aaaacaagtt gagaatcgcc ttgagaaagc       420
tatctctagg atcaggtcca agaagcatga gttgcttcta gttgaaatcg aaaacgcgca       480 gaaagggag attgagcttg acaatgagaa catctatcta agaactaagg tagcagaagt       540
ggagaggtat caacaacacc atcatcaaat ggttagtggt tcagagatta acgcaattga       600
agctttagcc tcacgcaatt actttgctca tagcattatg actgctggtt ctggatctgg       660
taatggaggt tcttactctg atcccgacaa gaaaattctt catctcggat aatctcgtct       720
gcgaaaaacc gagctgcaat aactctctgc atgcatctgg ggattctttg ctcagattta      780
tctctacata aaatatgttt tggtgcaaaa taattcaaag tacaatgaag gtattggtcc       840
ttcaagactc attgcaattt gtgttgtgta atgattaaga catactctag ttttattgc       900 ttcgt                                                                  905
```

<210> SEQ ID NO 7
<211> LENGTH: 1268
<212> TYPE: DNA
<213> ORGANISM: Artificial sequence
<220> FEATURE:
<223> OTHER INFORMATION: Fully synthetic sequence

<400> SEQUENCE: 7

```
acatcctctt tcagttccct ctctggatct cttcctgaag agaggcactg ccacaccacc      60
acgccaccca tgctcaacat gatgaccgat ctgagctgcg gccgtcgtc caaggcgaaa      120
ggagggcagc cggcagcgac gacgggctcc ggcggcgaca ggcaggggag gggcaagatc     180
gagatcaagc gcatcgagaa cacgacgaac cggcaggtca ccttctgcaa cgccgcaac     240
ggcctgctca agaaggcgta cgagctctcg gtgctctgcg acgccgaggt cgcgctcgtc     300
gtccctcca gccgcggccg cctctacgag gacgccaaca cagtgtgaa gtccaccatt      360
gagaggtaca agaaggccaa cagtgacacc tccaactctg gcacagttgc agaagtcaat    420
gctcagcact accagcagga gtcctccaag ctgcgccagg cgatcgatag cttgcaaaac    480
gcaaacagga ccatagtggg agattcaatc cacaccatgg gcctcaggga gcttaagcag    540
atggagggca agctggagaa ggccataaac aagattaggg ctagaaagaa tgagctcttg    600
tatgctgaag ttgaatatat gcaaagaagg atggatctgc agactgacaa catgtacctg    660
aggagcaaga tcgccgagaa taataatgaa acggggcagc cagcgatgaa catgattgga    720
gtgccgtcga cgagcgagta cgatcacatg gcctcttttg ttgactcgag aaactttctt    780
caggtgaaca tgcagcagca gcagcctcag cactactccc atcagctgca accaacgacc    840
ctccaactcg gatgatgaaa ttaagaatct tcggccaaca atccatgcac gcaagcacgc    900
agtaaatcat gtgtgtccaa ctcagataaa aaatctact ctagcgtttg tataattatt    960
aataatcgtg actagtaaac tgttatatat atatgtatgc catgtgtgtg gtggcgccta   1020
catatatgtc atgtggctgt acggcgagtt ttttttttcac aagcgtttgc agcagcattt  1080
ggtgttgctc atccatcaat taatcgcaag aaattaaacc tgtcaccacc gtgtgtgcat   1140
ttgtacgtgt taatgcagtt gttgtatccg ttaattgtac cctccatcag ataaacgcgg  1200
gtgcgcgtat gcataaaaaa aaaaaaaact tatttatgtg tatgattatt tgtgtagttt   1260
atatcgcc                                                            1268
```

<210> SEQ ID NO 8
<211> LENGTH: 1575
<212> TYPE: DNA
<213> ORGANISM: Artificial sequence
<220> FEATURE:
<223> OTHER INFORMATION: Fully synthetic sequence

<400> SEQUENCE: 8

```
tacctcgag gccggccggg ccgggcagga gcaagaaaca ctcagaagct gcccagagct       60
accaccctc ttatcccac ccctcctcct cctacctttt ctccttcaga cctcaaaatc      120
tgtgtgtctc ctgccgcggc tagctgatag gaacaagagc atgcacatcc gagaagagga    180
ggctacacca tccacagtaa caggcatcat gtcgaccctg acttcggcgg gcagcagaa    240
gctgaaggag cccatatccc ctggtggcgg ctccgcgtcg gtcgctgggt ccgctgcgga   300
gaggaacaac ggcggcaggg gcaagggcaa gactgagatc aagcgcatcg agaacacgac   360
caacaggcag gtcaccttct gcaagcgccg caacggcctc ctcaagaagg cgtacgagct   420
```

-continued

```
ctccgtgctc tgcgacgccg aggtcgcgct catcgtcttc tccagccgcg gccgcctcta    480
cgagtacgcc aacaacagcg tgaagggcac cattgagagg tacaagaagg caaccagtga    540
caactccagc gcagctggta cgattgcaga ggtcaccatt cagcattaca agcaggaatc    600
tgctaggctg aggcagcaga tcgttaactt gcagaactcc aacagggccc tgataggtga    660
ttctatcaca accatgagcc acaaggaact taagcacttg gagactaggt tagacaaagc    720
tctcggaaag attagagcaa aaagaacga tgtgctgtgt tctgaagtcg agtacatgca    780
gagaagggaa atggagttgc agaatgacaa cttgtactta aggagccggg ttgatgagaa    840
tgaaagggca caacagacag cgaacatgat ggggcacca tcgacaagtg agtatcagca    900
gcacggtttt actccttatg atccaataag gagcttcctg cagttcaaca tcgtgcagca    960
gcctcagttc tattctcagc aggaggaccg gaaagacttc aacgaccaag gtggaagata   1020
aatattggac ctctcaagct tcagtactta tccgtgatga tgcatgactg ccagtgagaa   1080
actgagctac attactgtgg aattatatgt aaagactagt actactgctt catatatgtg   1140
catgtgcgca cacgcgcacg tagtatgcac aatttcatcc cactattatg cttggcacc    1200
aactatgtct ccttaattat cataggagaa aaataagtca cgcacaaaaa aattctaaag   1260
atgaggcaaa gagttggatg actgaaactg aaagatagga ttctcgtgga tggcggtgga   1320
catatatatg ccatgcacat ctgatctctg gccagtgtg tttaattgac tgcactttat    1380
atacggttg aacagatgta attcgagggc tgcaaccagg ctaagggcat acgcggctgg    1440
cagccgtatg cccgcgtgca ggcgctgcca atgcagcagc acacaaaacg atgtatagtt   1500
tatgtgtgtt tttctattat atctttcaat aaaaagattt aaccactaaa aaaaaaaga   1560
aaaaaaaaaa aaaaa                                                   1575
```

<210> SEQ ID NO 9
<211> LENGTH: 1373
<212> TYPE: DNA
<213> ORGANISM: Artificial sequence
<220> FEATURE:
<223> OTHER INFORMATION: Fully synthetic sequence

<400> SEQUENCE: 9

```
gaactcgtaa atcttgtgtt cctgtgtggc tgctttcgtt agatctctcg gctatgtcta     60
tatgatcgtc ttggccagca tctctgggtt cttttcgcgg ccgagaggaa acttactaac    120
tgatcgagtg tgccaggcat caatctgtcg aatcgtgact cgtcgctttt tcatgtcttc    180
agattttgtc catctgtcaa atcatgtgga aaaattggca tatcttcttg tattctcttc    240
tgtccttttt aatgcctcca gcggattaat ttctagctag ttccgttcca ttgatctgcc    300
ttcagataat ataacttaaa ttctcgcttt cttatgcaag aactaaatta cttgcatttc    360
agctgagatc tccagcatgg ggagggaag gattgagatc aagaggatcg agaacaacac    420
gagccggcag gtcaccttct gcaagcgccg caatgggctc tcaagaaggc gtacgagct    480
ctccgtcctc tgcgacgccg aggtggcgct cgtcgtcttc tccagccgcg gacgcctcta    540
cgagtacgcc aacaacagtg tgaaggctac gatcgagagg tacaagaagg cacacgccgt    600
tggctcttcc tctggccccc cactcttaga gcacaatgcc cagcaattct accagcaaga    660
atccgcaaaa ctgcgcaacc agatccgat gctgcaaaac actaacaggc acttggttgg    720
tgactctgtg ggaaacttgt cactcaaaga gctgaagcag ctggagagcc gccttgagaa    780
aggcatctct aagatcaggg ccaggaagag tgagctgctg gctgccgaga tcaattacat    840
ggccaaaagg gagactgagc ttcagaatga ccacatgaac ctcaggacca agattgagga    900
```

-continued

```
gggagagcaa cagctgcagc aggtgactgt ggcccagtct gtcgcagcag cagcggccac    960
cgacgtggag ctgaatccgt tcttggagat ggataccaaa tgcttcttcc ctggcggccc   1020
cttcgcgaca ctggacatga agtgcttctt ccccggcagc ttgcagatgc tggaggcaca   1080
gcagcgccag atgcttgcca ccgagctgaa cctcggctac caactggcgc cgcctgacac   1140
tgacgttgcc aacaataacc ctcagcagtt ctaaactgga tccatgagaa agccaactgt   1200
gaccgatgga agctggctgt tgcctctaga tgatattggc ttccataacc tagcttatta   1260
tggtgtgtat tgttgccttt tgtgtgtgat tctccttgct actgatggag aataaaccta   1320
atcgattggg cataatgatc aaatgctaca gcacccgtga ggctgtgatc agg          1373
```

<210> SEQ ID NO 10
<211> LENGTH: 1259
<212> TYPE: DNA
<213> ORGANISM: Artificial sequence
<220> FEATURE:
<223> OTHER INFORMATION: Fully synthetic sequence

<400> SEQUENCE: 10

```
acttccggtt acaaaagctg cagctcctcc gcgcttcgcc ggtctagcag cagcgcctcc     60
ccgccgctcc tgcacaacgg catgacctct ttcatccaga gcgcgacgta ctgcgagacc    120
agagccacga ccaccaccac cacgacacca tgctgaacat gatgactgat cggagaggcg    180
ggccgtcggc gaatcgagaa gagcaggtgg cggcagcgca cattcggcaa gcgccgcgac    240 gggggggcgcg ggaaggcata agagctctca gggccatccg gagcacgagt agccggcagg    300
tgaccttctg caagcgccgg aacggcctgc tcaagaaggc atacgagctc tcggtgctct    360
gcgaggccga agtagcgctc gacggcttct ccagccgctg ccgcctctac gagtacgcca    420
acaacagtgt gaagtccacc attgagaggt acaagaaggc caacagtgac tcctccaact    480
ctggcacagt tgcagaagtc aatgcccagt actaccagca ggagtcctcc aagctgcgac    540
agatgatcca cagcttgcaa acgcaaaaca ctaggaacat agtgggagat tccatccaca    600
ccatgggcct cagggatctt aaacaaatgg agggcaagct ggagaaagcc ataatcaaga    660
ttagagctag aaagaatgag ctgctatacg ctgaagttga ctatatgcaa aaagggaga    720 tggatctgca gactgacaac atgtacctga ggagcaagat cgctgagagt aatgaaacgg    780
ggcagccggc gatgcacatg acgatgggag cgccgccgac gagcgagtac gaccacatgg    840 ccccttcga ctcgagaaac tttctgcaag tgagcatgcc tcagcactac tcccatcagc    900
tgcaacctac aaccctccag ctcggatgat gaaatcagcg ctataccbgg cggcgcccgg    960 ccccaatcg agatagatca cgcatgcagt tatatcatgt gccaaatcga gatctcaagt   1020
aactctacgt acgtttgctt aattattaat aattgtgatt agtgcaactg ttagggtata   1080
tatatttgtg agtgccacca ctgtgtgcgt gcatttgtac gtgtgaattt agctgttgca   1140
tctactacta ttgtaccctc cggccaggcc atatcatcag aaacgcgggt ttatatacgc   1200
acacatatat atatatataa tttgtatgct taatatagat tgaaaatagt atgttgggc    1259
```

<210> SEQ ID NO 11
<211> LENGTH: 1448
<212> TYPE: DNA
<213> ORGANISM: Artificial sequence
<220> FEATURE:
<223> OTHER INFORMATION: Fully synthetic sequence

<400> SEQUENCE: 11

| | |
|---|---|
| agcacttgtc ctcgaggccg gccgggacag gggcagccag gcacacacac acacagtgac | 60 |
| cctgcccctt ttcccggccg tctcgctctc caccgatatt ccgctcctcc tgtccagtcc | 120 |
| tcctcccccg agccggctca ttatatcgtc cgtcgcgcag cacaacgcaa gtttgctagc | 180 |
| ggccggatca gcagccacaa aacgaggaga gcaaccacgc tgcacacaga gacgcccgtg | 240 |
| tgtgagatat agagcaagct cgatcgaagg aaggagggaa gctagagatc gtacgtcgcc | 300 |
| atggggaggg gacgagttga gctcaagcgg atcgagaaca agatcaaccg ccaggtcacc | 360 |
| ttctccaagc gccgcaacgg cctgctcaag aaggcctacg agctctccgt gctctgcgac | 420 |
| gccgaggtcg cgctcatcat cttctccagc gcggcaagc tctacgagtt cggcagcgcc | 480 |
| ggcataacaa aaactttaga aaggtaccaa cattgctgct acaatgctca agattccaat | 540 |
| ggcgcactct ctgaaactca gagctggtac caggaaatgt caaaactgag ggcaaaattc | 600 |
| gaggccttgc agcgcactca gaggcacttg cttggggagg aacttggccc actgagtgtg | 660 |
| aaggagttgc agcagctaga gaaacagctc gaatgtgctt tgtcacaggc aagacagaga | 720 |
| aagacacaac ttatgatgga gcaagtggaa gagctccgca gaaaggagcg cacctgggag | 780 |
| gaaatgaaca gcaactcaa acacaagctt gaagctgaag gttgtagcaa ctacagaacc | 840 |
| ctgcagcatg cagcctggcc agctcccggc agcaccatgg tggagcatga cggcgccacc | 900 |
| tatcatgtgc atccaacaac tgctcaatcg gttgcaatgg actgtgaacc cactctgcaa | 960 |
| atcgggtacc ctcctcatca ccagtttctg ccttccgagg cagccaataa tatcccaagg | 1020 |
| agcccccctg gaggcgagaa caacttcatg ctgggatggg ttctttgagt tgctctgtta | 1080 |
| atcatccatc catcagatgg atgtccaaac taataaaagg cactcagtgc taccatatgc | 1140 |
| atatccatgc ttaagtgctt gatttgccac gacgtgggat atcttttaaa tttatcgttc | 1200 |
| tggtgtgtaa taactaatta agaacggcac cttcattcta tggttgtggt gtggcacttc | 1260 |
| tatctatggt ttttgtattt ggaccacgaa tgttgtaatt tgtaaaaaaa atttaaagat | 1320 |
| ttatctatgc tgccggtgct gcggtgcata gcccggtgca tagaatccaa aaaaaaaaaa | 1380 |
| aaaaaaaaa aaaaaaaaa aaaaaaaaa aaaaaaaaa aaaaaaaaa aaaaaaaaa | 1440 |
| aaaagaaa | 1448 |

<210> SEQ ID NO 12
<211> LENGTH: 1169
<212> TYPE: DNA
<213> ORGANISM: Artificial sequence
<220> FEATURE:
<223> OTHER INFORMATION: Fully synthetic sequence
<220> FEATURE:
<221> NAME/KEY: misc_feature
<222> LOCATION: (1161)..(1169)
<223> OTHER INFORMATION: n is a, c, g, or t

<400> SEQUENCE: 12

| | |
|---|---|
| gccggccggg ccgggctcca ttagcgccga gcatcagatc tcgccccaag cccccaaccc | 60 |
| agggtacgaa tacgatgacg ctctataagc atctctcact gctgcttaca gcaacccagg | 120 |
| actctgctgc ttatagctag agagaggaca cggaggcaga gagagaccaa gctagaggga | 180 |
| cgcaaaacaa gctagctagg aggaagatgg gtcgcggcaa ggaggagctg aagcggatcg | 240 |
| agaacaagat cagccggcag gtgacgttcg ccaagcgccg gaacgggctg ctcaagaagg | 300 |
| cgtacgagct gtcggtgctc tgcgacgccg aggtcgccct tatcatcttc tccagccgcg | 360 |
| gccgcctctt cgagttctcc acctcctcat gcatctacaa gacgctggag cgataccgca | 420 |
| gctgcagctt tgcatccgaa gcatcagctc cactagaggc tgaattaaat aattatcagg | 480 |

| | |
|---|---|
| agtacttgaa gttaaagaca agagttgagt tcttacaaac aactcagaga aatctacttg | 540 |
| gtgaggactt gggtccactt agcgtgaagg agttagagca acttgagaac caaattgaga | 600 |
| tatctctcaa gcaaatccga tcatcaaaga accagcagat gctcgaccag ctctttgatc | 660 |
| tcaagcgcaa ggaacaacaa ctgcaagatg ctaacaaaga tttaagaatg aagatagaag | 720 |
| aaactagtga agaaaatgtg ctgcgactgt ctagccagga tattgggtgt agtggatcta | 780 |
| gtgggcatgg tgatgaagcc aaccaagaac accttcaact tgctcttgat ccttcgctgc | 840 |
| atatagggta tcaagcttac atggaccacc tgaacaatga ttaagttgct tctttgtgcg | 900 |
| ctgtgtgctc tagtggccat ggatcttcta tatatgttgg acgtaatgct tttgataaat | 960 |
| cctctatata taaccatatc ggtcctagct ttatgcatgc tactgtatgt actaaactaa | 1020 |
| gaagccctac gacttctgtt gaggaagaat gttctgacga tcatgacttt ttcttgctaa | 1080 |
| ataataacta ctgtatctca ttttgaattg atcgtctact gaagagccat gcttttgtga | 1140 |
| gtacttaaaa aaaaaaaaaa nnnnnnnnn | 1169 |

<210> SEQ ID NO 13
<211> LENGTH: 1453
<212> TYPE: DNA
<213> ORGANISM: Artificial sequence
<220> FEATURE:
<223> OTHER INFORMATION: Fully synthetic sequence

<400> SEQUENCE: 13

| | |
|---|---|
| attccggttt ctcgataccg gctcgggtgc tccctcctcc cctcccctcc gatcaagtcg | 60 |
| gggcaacgcg catcactcgc tttaaatccg cacctcccgg ccggtcccct tatcacctca | 120 |
| ccttctcctt tgagtcctct ctctccgccg ccgcagctag ctgtgacgtt atgctctcgc | 180 |
| cggcgccata gcgccagcgc ctaccgtcta caactatcca gccttaggct tacctatccc | 240 |
| gtcaatcaag cctctcgtaa ggaacaagga agtagctag ctagttctat agctgctgtc | 300 |
| gtcgtcgtca tcggcggcgg cggcgcctgt tcttagagga taaggttgtc ctagcggaga | 360 |
| gggagctagc caggatttcg gttgagatca agaggggaga caggcggcgg cggcggcgat | 420 |
| ggggcgcggg aaggtgcagc tgaagcggat cgagaacaag atcaaccgcc aggtgacctt | 480 |
| ctccaagcgc cgctcgggc tgctcaagaa ggcgcacgag atctccgtgc tctgcgacgc | 540 |
| cgaggtcgcg ctcatcatct tctccaccaa agggaagctc tacgagtatt ccaccgattc | 600 |
| atgtatggac aaaattcttg accggtacga gcgctactcc tatgcagaaa aggttcttat | 660 |
| ttcagcagaa tctgaaactc agggcaattg gtgccacgag tatagaaaac taaaggcgaa | 720 |
| ggtcgagaca atacaaaaat gtcaaaagca cctcatggga gaggatcttg aaacgttgaa | 780 |
| tctcaaagag cttcagcaac tagagcagca gctggagagt tcactgaaac atatcagaac | 840 |
| caggaagaac caactatgc tcgagtcaat ttcggagctc caacggaagg agaagtcgct | 900 |
| gcaggaggag aacaaggttc tgcagaagga gctcgcggag aagcagaaag cccagcggaa | 960 |
| gcaagtgcaa tggggccaaa cccaacagca gaccagttcg tcttcctcgt gcttcgtgat | 1020 |
| aagggaagct gccccaacaa caaatatcag cattttttcct gtggcagcag gcgggaggtt | 1080 |
| ggtgaaggt gcagcagcgc agccacaggc tcgcgttgga ctaccaccat ggatgcttag | 1140 |
| ccacctgagc agctgaaggt ttcagcaact cttcccgttt atccgcctgg tgcagtatag | 1200 |
| tatcatcgtg atcgcgagag cagcagcagt gggtttgccg tatcttttt taccaatgta | 1260 |
| tgtctatata tgtaagtatc aaatctgcaa tgtgttaatc accatttccg ctgggacgcc | 1320 |

```
tgtcatatat gtgcttcatc aaatcacttt cactaaaata aaaagtaccg gtttgtggta   1380
gtttcatgtc tcacataaca gatacacaat ctgttccctg tggtcccgcc gcttcctgct   1440
ggggcggccg aaa                                                      1453

<210> SEQ ID NO 14
<211> LENGTH: 1764
<212> TYPE: DNA
<213> ORGANISM: Artificial sequence
<220> FEATURE:
<223> OTHER INFORMATION: Fully synthetic sequence
<220> FEATURE:
<221> NAME/KEY: misc_feature
<222> LOCATION: (35)..(35)
<223> OTHER INFORMATION: n is a, c, g, or t

<400> SEQUENCE: 14
aagctggagc tccccgcggt ggcggccgct ctagnaacta gtggatcccc cgggctgcag     60
gaattcggca cgagagagaa ctagtccccc cccccccccg ccctgagatg catgggggtag   120 ccaatcgggt gtcgccgtgc gcgcgcgcg gcgtctggcc tcctccttcc ctttccttgc    180
taaataaagc aagtagcaga taggggaaag tctgctcgca agttgcatcc gccctgcgcc    240
aagaaaagcc atcgttcttc ccacaaacgc acacatagaa gcatcattcc cctctcggct    300
agcttcctcc tctctcccctc ctcttcgtct tcctcttttcc ttctcccttg ggaaacctgc   360
tgcctttgag ctttcttctt cgagtgctcc caccagatct cctcctcctt accttctttg   420
gcacgttcgg cggcgcgcgc ggagatagat agatcccgcc atcgtcgtcg ccgtccttgc    480
ttccgatcgg agggccacaa ccacaacctc tcgctcctta gcgtgcgcgc gcgagccagg   540
gtcaagaaga gagctagcta gcttaggccg gagatcgatg gggaggggaa agatcgtgat   600
ccgcaggatc gataactcca cgagccggca ggtgaccttc tccaagcgcc ggaacgggat   660
cttcaagaag gccaaggagc tcgccatcct ctgcgatgcg gaggtcggcc tcgtcatctt   720
ctccagcacc ggccgcctct acgagtactc tagcaccagc atgaaatcag ttatagatcg   780
gtacggcaag gccaaggaag agcagcaagt cgtcgcaaat cccaactcgg agcttaagtt    840
ttggcaaagg gaggcagcaa gcttgagaca acaactgcac aacttgcaag aaaattatcg   900
gcagttgacg ggagatgatc tttctgggct gaatgtcaaa gaactgcagt ccctggagaa   960
tcaattggaa acaagcctgc gtggtgtccg cgcaaagaag gaccatctct tgatagatga   1020
gattcacgat ttgaatcgaa aggcaagttt atttcaccaa gaaatacag acttgtacaa     1080 taagatcaac ctgattcgcc aagaaaatga tgagttacat aaaaagatct atgagactga   1140
aggaccaagt ggagttaatc gggagtcacc gactccattc aactttgcag tagtagaaac   1200
cagagatgtt ccagtgcaac ttgaactcag cacactgcca caacaaaata acattgagcc   1260
atctactgct cctaagctag gattgcaatt aattccatga agaagagtaa aactgccgtc   1320
ttatgatgct gaaggaaact atttattgtg aagagatgat actcagagaa agacatattt   1380
gtggcaggga gatttgagat atgaacttat aaatgtaatg caaataattt tcagactgga   1440
atggggtcgt ggaattcaga ggatgattgc tttctagttg catttgatgt ttgatgagac   1500
ttttctcatg tgaaacgttt attaaaactt caaaatggtg cagatgttgc tactacccctt   1560 gttaggcttg tataaatatt tgactttgtg tactagcatt acgaaaacag aaaagaagac   1620
agacagccgt gatagggagc aatgatgcga tctaggagta caaacagagt ctagtttcca   1680
ctcagttgag ttttatattg ctctcaagcg ttatcaaggg tttagtagga tacagatata   1740
attaagatac agtggttaaa tcgc                                          1764
```

<210> SEQ ID NO 15
<211> LENGTH: 261
<212> TYPE: PRT
<213> ORGANISM: Artificial sequence
<220> FEATURE:
<223> OTHER INFORMATION: Fully synthetic sequence

<400> SEQUENCE: 15

```
Met Leu Asn Met Met Thr Asp Leu Ser Cys Gly Pro Ser Ser Lys Ala
1               5                   10                  15

Lys Gly Gly Gln Pro Ala Ala Thr Thr Gly Ser Gly Gly Asp Arg Gln
            20                  25                  30

Gly Arg Gly Lys Ile Glu Ile Lys Arg Ile Glu Asn Thr Thr Asn Arg
        35                  40                  45

Gln Val Thr Phe Cys Lys Arg Arg Asn Gly Leu Leu Lys Lys Ala Tyr
    50                  55                  60

Glu Leu Ser Val Leu Cys Asp Ala Glu Val Ala Leu Val Val Pro Ser
65                  70                  75                  80

Ser Arg Gly Arg Leu Tyr Glu Asp Ala Asn Asn Ser Val Lys Ser Thr
                85                  90                  95

Ile Glu Arg Tyr Lys Lys Ala Asn Ser Asp Thr Ser Asn Ser Gly Thr
            100                 105                 110

Val Ala Glu Val Asn Ala Gln His Tyr Gln Gln Glu Ser Ser Lys Leu
        115                 120                 125

Arg Gln Ala Ile Asp Ser Leu Gln Asn Ala Asn Arg Thr Ile Val Gly
    130                 135                 140

Asp Ser Ile His Thr Met Gly Leu Arg Glu Leu Lys Gln Met Glu Gly
145                 150                 155                 160

Lys Leu Glu Lys Ala Ile Asn Lys Ile Arg Ala Arg Lys Asn Glu Leu
                165                 170                 175

Leu Tyr Ala Glu Val Glu Tyr Met Gln Arg Arg Met Asp Leu Gln Thr
            180                 185                 190

Asp Asn Met Tyr Leu Arg Ser Lys Ile Ala Glu Asn Asn Asn Glu Thr
        195                 200                 205

Gly Gln Pro Ala Met Asn Met Ile Gly Val Pro Ser Thr Ser Glu Tyr
    210                 215                 220

Asp His Met Ala Ser Phe Val Asp Ser Arg Asn Phe Leu Gln Val Asn
225                 230                 235                 240

Met Gln Gln Gln Gln Pro Gln His Tyr Ser His Gln Leu Gln Pro Thr
                245                 250                 255

Thr Leu Gln Leu Gly
            260
```

<210> SEQ ID NO 16
<211> LENGTH: 270
<212> TYPE: PRT
<213> ORGANISM: Artificial sequence
<220> FEATURE:
<223> OTHER INFORMATION: Fully synthetic sequence

<400> SEQUENCE: 16

```
Met Ser Thr Leu Thr Ser Ala Gly Gln Gln Lys Leu Lys Glu Pro Ile
1               5                   10                  15

Ser Pro Gly Gly Gly Ser Ala Ser Val Ala Gly Ser Ala Ala Glu Arg
            20                  25                  30

Asn Asn Gly Gly Arg Gly Lys Gly Lys Thr Glu Ile Lys Arg Ile Glu
```

```
                35                  40                  45
Asn Thr Thr Asn Arg Gln Val Thr Phe Cys Lys Arg Arg Asn Gly Leu
         50                  55                  60

Leu Lys Ala Tyr Glu Leu Ser Val Leu Cys Asp Ala Glu Val Ala
 65                  70                  75                  80

Leu Ile Val Phe Ser Ser Arg Gly Arg Leu Tyr Glu Tyr Ala Asn Asn
                 85                  90                  95

Ser Val Lys Gly Thr Ile Glu Arg Tyr Lys Lys Ala Thr Ser Asp Asn
            100                 105                 110

Ser Ser Ala Ala Gly Thr Ile Ala Glu Val Thr Ile Gln His Tyr Lys
            115                 120                 125

Gln Glu Ser Ala Arg Leu Arg Gln Gln Ile Val Asn Leu Gln Asn Ser
        130                 135                 140

Asn Arg Ala Leu Ile Gly Asp Ser Ile Thr Thr Met Ser His Lys Glu
145                 150                 155                 160

Leu Lys His Leu Glu Thr Arg Leu Asp Lys Ala Leu Gly Lys Ile Arg
                165                 170                 175

Ala Lys Lys Asn Asp Val Leu Cys Ser Glu Val Glu Tyr Met Gln Arg
            180                 185                 190

Arg Glu Met Glu Leu Gln Asn Asp Asn Leu Tyr Leu Arg Ser Arg Val
        195                 200                 205

Asp Glu Asn Glu Arg Ala Gln Gln Thr Ala Asn Met Met Gly Ala Pro
    210                 215                 220

Ser Thr Ser Glu Tyr Gln Gln His Gly Phe Thr Pro Tyr Asp Pro Ile
225                 230                 235                 240

Arg Ser Phe Leu Gln Phe Asn Ile Val Gln Gln Pro Gln Phe Tyr Ser
                245                 250                 255

Gln Gln Glu Asp Arg Lys Asp Phe Asn Asp Gln Gly Gly Arg
            260                 265                 270

<210> SEQ ID NO 17
<211> LENGTH: 265
<212> TYPE: PRT
<213> ORGANISM: Artificial sequence
<220> FEATURE:
<223> OTHER INFORMATION: Fully synthetic sequence

<400> SEQUENCE: 17

Met Gly Arg Gly Arg Ile Glu Ile Lys Arg Ile Glu Asn Asn Thr Ser
 1               5                  10                  15

Arg Gln Val Thr Phe Cys Lys Arg Arg Asn Gly Leu Leu Lys Lys Ala
                20                  25                  30

Tyr Glu Leu Ser Val Leu Cys Asp Ala Glu Val Ala Leu Val Val Phe
            35                  40                  45

Ser Ser Arg Gly Arg Leu Tyr Glu Tyr Ala Asn Asn Ser Val Lys Ala
        50                  55                  60

Thr Ile Glu Arg Tyr Lys Lys Ala His Ala Val Gly Ser Ser Ser Gly
 65                  70                  75                  80

Pro Pro Leu Leu Glu His Asn Ala Gln Gln Phe Tyr Gln Gln Glu Ser
                 85                  90                  95

Ala Lys Leu Arg Asn Gln Ile Gln Met Leu Gln Asn Thr Asn Arg His
            100                 105                 110

Leu Val Gly Asp Ser Val Gly Asn Leu Ser Leu Lys Glu Leu Lys Gln
        115                 120                 125

Leu Glu Ser Arg Leu Glu Lys Gly Ile Ser Lys Ile Arg Ala Arg Lys
```

-continued

```
            130                 135                 140
Ser Glu Leu Leu Ala Ala Glu Ile Asn Tyr Met Ala Lys Arg Glu Thr
145                 150                 155                 160

Glu Leu Gln Asn Asp His Met Asn Leu Arg Thr Lys Ile Glu Glu Gly
                165                 170                 175

Glu Gln Gln Leu Gln Gln Val Thr Val Ala Gln Ser Val Ala Ala Ala
            180                 185                 190

Ala Ala Thr Asp Val Glu Leu Asn Pro Phe Leu Glu Met Asp Thr Lys
            195                 200                 205

Cys Phe Phe Pro Gly Gly Pro Phe Ala Thr Leu Asp Met Lys Cys Phe
210                 215                 220

Phe Pro Gly Ser Leu Gln Met Leu Glu Ala Gln Gln Arg Gln Met Leu
225                 230                 235                 240

Ala Thr Glu Leu Asn Leu Gly Tyr Gln Leu Ala Pro Pro Asp Thr Asp
                245                 250                 255

Val Ala Asn Asn Asn Pro Gln Gln Phe
                260                 265

<210> SEQ ID NO 18
<211> LENGTH: 259
<212> TYPE: PRT
<213> ORGANISM: Artificial sequence
<220> FEATURE:
<223> OTHER INFORMATION: Fully synthetic sequence

<400> SEQUENCE: 18

Met Leu Asn Met Met Thr Asp Arg Arg Gly Gly Pro Ser Ala Asn Arg
1               5                   10                  15

Glu Glu Gln Val Ala Ala His Ile Arg Gln Ala Pro Arg Arg Gly
            20                  25                  30

Ala Arg Glu Gly Ile Arg Ala Leu Arg Ala Ile Arg Ser Thr Ser Ser
        35                  40                  45

Arg Gln Val Thr Phe Cys Lys Arg Arg Asn Gly Leu Leu Lys Lys Ala
    50                  55                  60

Tyr Glu Leu Ser Val Leu Cys Glu Ala Glu Val Ala Leu Asp Gly Phe
65                  70                  75                  80

Ser Ser Arg Cys Arg Leu Tyr Glu Tyr Ala Asn Asn Ser Val Lys Ser
                85                  90                  95

Thr Ile Glu Arg Tyr Lys Lys Ala Asn Ser Asp Ser Ser Asn Ser Gly
            100                 105                 110

Thr Val Ala Glu Val Asn Ala Gln Tyr Tyr Gln Gln Glu Ser Ser Lys
        115                 120                 125

Leu Arg Gln Met Ile His Ser Leu Gln Asn Ala Asn Thr Arg Asn Ile
    130                 135                 140

Val Gly Asp Ser Ile His Thr Met Gly Leu Arg Asp Leu Lys Gln Met
145                 150                 155                 160

Glu Gly Lys Leu Glu Lys Ala Ile Ile Lys Ile Arg Ala Arg Lys Asn
                165                 170                 175

Glu Leu Leu Tyr Ala Glu Val Asp Tyr Met Gln Lys Arg Glu Met Asp
            180                 185                 190

Leu Gln Thr Asp Asn Met Tyr Leu Arg Ser Lys Ile Ala Glu Ser Asn
        195                 200                 205

Glu Thr Gly Gln Pro Ala Met His Met Thr Met Gly Ala Pro Pro Thr
    210                 215                 220

Ser Glu Tyr Asp His Met Ala Pro Phe Asp Ser Arg Asn Phe Leu Gln
```

```
                    225                 230                 235                 240
Val Ser Met Pro Gln His Tyr Ser His Gln Leu Gln Pro Thr Thr Leu
                245                 250                 255

Gln Leu Gly

<210> SEQ ID NO 19
<211> LENGTH: 255
<212> TYPE: PRT
<213> ORGANISM: Artificial sequence
<220> FEATURE:
<223> OTHER INFORMATION: Fully synthetic sequence

<400> SEQUENCE: 19

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Ile Thr Lys
    50                  55                  60

Thr Leu Glu Arg Tyr Gln His Cys Cys Tyr Asn Ala Gln Asp Ser Asn
65                  70                  75                  80

Gly Ala Leu Ser Glu Thr Gln Ser Trp Tyr Gln Glu Met Ser Lys Leu
                85                  90                  95

Arg Ala Lys Phe Glu Ala Leu Gln Arg Thr Gln Arg His Leu Leu Gly
                100                 105                 110

Glu Glu Leu Gly Pro Leu Ser Val Lys Glu Leu Gln Gln Leu Glu Lys
            115                 120                 125

Gln Leu Glu Cys Ala Leu Ser Gln Ala Arg Gln Arg Lys Thr Gln Leu
    130                 135                 140

Met Met Glu Gln Val Glu Leu Arg Arg Lys Glu Arg His Leu Gly
145                 150                 155                 160

Glu Met Asn Arg Gln Leu Lys His Lys Leu Glu Ala Glu Gly Cys Ser
                165                 170                 175

Asn Tyr Arg Thr Leu Gln His Ala Ala Trp Pro Ala Pro Gly Ser Thr
                180                 185                 190

Met Val Glu His Asp Gly Ala Thr Tyr His Val His Pro Thr Thr Ala
            195                 200                 205

Gln Ser Val Ala Met Asp Cys Glu Pro Thr Leu Gln Ile Gly Tyr Pro
    210                 215                 220

Pro His His Gln Phe Leu Pro Ser Glu Ala Ala Asn Asn Ile Pro Arg
225                 230                 235                 240

Ser Pro Pro Gly Gly Glu Asn Asn Phe Met Leu Gly Trp Val Leu
                245                 250                 255

<210> SEQ ID NO 20
<211> LENGTH: 225
<212> TYPE: PRT
<213> ORGANISM: Artificial sequence
<220> FEATURE:
<223> OTHER INFORMATION: Fully synthetic sequence

<400> SEQUENCE: 20

Met Gly Arg Gly Lys Glu Glu Leu Lys Arg Ile Glu Asn Lys Ile Ser
1               5                   10                  15

Arg Gln Val Thr Phe Ala Lys Arg Arg Asn Gly Leu Leu Lys Lys Ala
```

```
                 20                  25                  30
Tyr Glu Leu Ser Val Leu Cys Asp Ala Glu Val Ala Leu Ile Ile Phe
             35                  40                  45
Ser Ser Arg Gly Arg Leu Phe Glu Phe Ser Thr Ser Ser Cys Ile Tyr
 50                  55                  60
Lys Thr Leu Glu Arg Tyr Arg Ser Cys Ser Phe Ala Ser Glu Ala Ser
 65                  70                  75                  80
Ala Pro Leu Glu Ala Glu Leu Asn Asn Tyr Gln Glu Tyr Leu Lys Leu
                 85                  90                  95
Lys Thr Arg Val Glu Phe Leu Gln Thr Thr Gln Arg Asn Leu Leu Gly
                100                 105                 110
Glu Asp Leu Gly Pro Leu Ser Val Lys Glu Leu Glu Gln Leu Glu Asn
                115                 120                 125
Gln Ile Glu Ile Ser Leu Lys Gln Ile Arg Ser Ser Lys Asn Gln Gln
                130                 135                 140
Met Leu Asp Gln Leu Phe Asp Leu Lys Arg Lys Glu Gln Gln Leu Gln
145                 150                 155                 160
Asp Ala Asn Lys Asp Leu Arg Met Lys Ile Glu Glu Thr Ser Glu Glu
                165                 170                 175
Asn Val Leu Arg Leu Ser Ser Gln Asp Ile Gly Cys Ser Gly Ser Ser
                180                 185                 190
Gly His Gly Asp Glu Ala Asn Gln Glu His Leu Gln Leu Ala Leu Asp
            195                 200                 205
Pro Ser Leu His Ile Gly Tyr Gln Ala Tyr Met Asp His Leu Asn Asn
        210                 215                 220
Asp
225

<210> SEQ ID NO 21
<211> LENGTH: 245
<212> TYPE: PRT
<213> ORGANISM: Artificial sequence
<220> FEATURE:
<223> OTHER INFORMATION: Fully synthetic sequence

<400> SEQUENCE: 21

Met Gly Arg Gly Lys Val Gln Leu Lys Arg Ile Glu Asn Lys Ile Asn
1               5                  10                  15
Arg Gln Val Thr Phe Ser Lys Arg Arg Ser Gly Leu Leu Lys Lys Ala
             20                  25                  30
His Glu Ile Ser Val Leu Cys Asp Ala Glu Val Ala Leu Ile Ile Phe
             35                  40                  45
Ser Thr Lys Gly Lys Leu Tyr Glu Tyr Ser Thr Asp Ser Cys Met Asp
 50                  55                  60
Lys Ile Leu Asp Arg Tyr Glu Arg Tyr Ser Tyr Ala Glu Lys Val Leu
 65                  70                  75                  80
Ile Ser Ala Glu Ser Glu Thr Gln Gly Asn Trp Cys His Glu Tyr Arg
                 85                  90                  95
Lys Leu Lys Ala Lys Val Glu Thr Ile Gln Lys Cys Gln Lys His Leu
                100                 105                 110
Met Gly Glu Asp Leu Glu Thr Leu Asn Leu Lys Glu Leu Gln Gln Leu
            115                 120                 125
Glu Gln Gln Leu Glu Ser Ser Leu Lys His Ile Arg Thr Arg Lys Asn
        130                 135                 140
Gln Leu Met Leu Glu Ser Ile Ser Glu Leu Gln Arg Lys Glu Lys Ser
```

```
                145                 150                 155                 160
Leu Gln Glu Glu Asn Lys Val Leu Gln Lys Glu Leu Ala Glu Lys Gln
                    165                 170                 175

Lys Ala Gln Arg Lys Gln Val Gln Trp Gly Gln Thr Gln Gln Gln Thr
                180                 185                 190

Ser Ser Ser Ser Cys Phe Val Ile Arg Glu Ala Ala Pro Thr Thr
                195                 200                 205

Asn Ile Ser Ile Phe Pro Val Ala Ala Gly Gly Arg Leu Val Glu Gly
                210                 215                 220

Ala Ala Ala Gln Pro Gln Ala Arg Val Gly Leu Pro Pro Trp Met Leu
225                 230                 235                 240

Ser His Leu Ser Ser
                245

<210> SEQ ID NO 22
<211> LENGTH: 240
<212> TYPE: PRT
<213> ORGANISM: Artificial sequence
<220> FEATURE:
<223> OTHER INFORMATION: Fully synthetic sequence

<400> SEQUENCE: 22

Met Gly Arg Gly Lys Ile Val Ile Arg Ile Asp Asn Ser Thr Ser
1                   5                   10                  15

Arg Gln Val Thr Phe Ser Lys Arg Arg Asn Gly Ile Phe Lys Lys Ala
                20                  25                  30

Lys Glu Leu Ala Ile Leu Cys Asp Ala Glu Val Gly Leu Val Ile Phe
            35                  40                  45

Ser Ser Thr Gly Arg Leu Tyr Glu Tyr Ser Ser Thr Ser Met Lys Ser
        50                  55                  60

Val Ile Asp Arg Tyr Gly Lys Ala Lys Glu Glu Gln Gln Val Val Ala
65                  70                  75                  80

Asn Pro Asn Ser Glu Leu Lys Phe Trp Gln Arg Glu Ala Ala Ser Leu
                85                  90                  95

Arg Gln Gln Leu His Asn Leu Gln Glu Asn Tyr Arg Gln Leu Thr Gly
            100                 105                 110

Asp Asp Leu Ser Gly Leu Asn Val Lys Glu Leu Gln Ser Leu Glu Asn
        115                 120                 125

Gln Leu Glu Thr Ser Leu Arg Gly Val Arg Ala Lys Lys Asp His Leu
    130                 135                 140

Leu Ile Asp Glu Ile His Asp Leu Asn Arg Lys Ala Ser Leu Phe His
145                 150                 155                 160

Gln Glu Asn Thr Asp Leu Tyr Asn Lys Ile Asn Leu Ile Arg Gln Glu
                165                 170                 175

Asn Asp Glu Leu His Lys Lys Ile Tyr Glu Thr Glu Gly Pro Ser Gly
            180                 185                 190

Val Asn Arg Glu Ser Pro Thr Pro Phe Asn Phe Ala Val Val Glu Thr
        195                 200                 205

Arg Asp Val Pro Val Gln Leu Glu Leu Ser Thr Leu Pro Gln Gln Asn
    210                 215                 220

Asn Ile Glu Pro Ser Thr Ala Pro Lys Leu Gly Leu Gln Leu Ile Pro
225                 230                 235                 240

<210> SEQ ID NO 23
<211> LENGTH: 509
<212> TYPE: DNA
```

<210> SEQ ID NO 23
<211> LENGTH: (not shown)
<212> TYPE: DNA
<213> ORGANISM: Artificial sequence
<220> FEATURE:
<223> OTHER INFORMATION: Fully synthetic sequence

<400> SEQUENCE: 23

```
gtgtgaagtc caccattgag aggtacaaga aggccaacag tgacacctcc aactctggca      60
cagttgcaga agtcaatgct cagcactacc agcaggagtc ctccaagctg cgccaggcga     120
tcgatagctt gcaaaacgca aacaggacca tagtgggaga ttcaatccac accatgggcc     180
tcagggagct taagcagatg gagggcaagc tggagaaggc cataaacaag attagggcta     240
gaaagaatga gctcttgtat gctgaagttg aatatatgca agaaggatg  gatctgcaga     300
ctgacaacat gtacctgagg agcaagatcg ccgagaataa taatgaaacg gggcagccag     360
cgatgaacat gattggagtg ccgtcgacga gcgagtacga tcacatggcc tcttttgttg     420
actcgagaaa ctttcttcag gtgaacatgc agcagcagca gcctcagcat tactcccatc     480
agctgcaacc aacgaccctc caactcgga                                       509
```

<210> SEQ ID NO 24
<211> LENGTH: 520
<212> TYPE: DNA
<213> ORGANISM: Artificial sequence
<220> FEATURE:
<223> OTHER INFORMATION: Fully synthetic sequence

<400> SEQUENCE: 24

```
gcgtgaaggg caccattgag aggtacaaga aggcaaccag tgacaactcc agcgcagctg      60
gtacgattgc agaggtcacc attcagcatt acaagcagga atctgctagg ctgaggcagc     120
agatcgttaa cttgcagaac tccaacaggg ccctgatagg tgattctatc acaaccatga     180
gccacaagga acttaagcac ttggagacta ggttagacaa agctctcgga aagattagag     240
caaaaaagaa cgatgtgctg tgttctgaag tcgagtacat gcagagaagg gaaatggagt     300
tgcagaatga caacttgtac ttaaggagcc gggttgatga gaatgaaagg gcacaacaga     360
cagcgaacat gatgggggca ccatcgacaa gtgagtatca gcagcacggt tttactcctt     420
atgatccaat aaggagcttc ctgcagtcca acatcgtgca gcagcctcag ttctattctc     480
agcaggagga ccggaaagac ttcaacgacc aaggtggaag                           520
```

<210> SEQ ID NO 25
<211> LENGTH: 243
<212> TYPE: DNA
<213> ORGANISM: Artificial sequence
<220> FEATURE:
<223> OTHER INFORMATION: Fully synthetic sequence

<400> SEQUENCE: 25

```
attgaggagg gagagcaaca gctgcagcag gtgtccgtgg cacggtcagt tgcagcagca      60
gcagctgcca ccaacttgga gctgaaccca ttcttggaga tggataccaa atgcttcttc     120
actggcggcc ccttcgcgac gctggtacat caagggcttt ctccccggca gcttgcagca     180
gatgctgcga ggcacagcag cgccagatgc atgcgccacc gagctgaacc tcggctacca     240
act                                                                   243
```

<210> SEQ ID NO 26
<211> LENGTH: 182
<212> TYPE: DNA
<213> ORGANISM: Artificial sequence
<220> FEATURE:
<223> OTHER INFORMATION: Fully synthetic sequence

<400> SEQUENCE: 26

```
gcaagatcgc tgagagtaat aatgaaagcg gggcagccag cgatgaacat gattggagtg        60
ccgtcgacga gcgagtacga tcacatggcc tcttttgttg actcgagaaa ctttcttcag       120
gtgaacatgc agcagcagca gcctcagcac tactcccatc agctgcaacc tacaaccctc       180
ca                                                                      182
```

<210> SEQ ID NO 27
<211> LENGTH: 461
<212> TYPE: DNA
<213> ORGANISM: Artificial sequence
<220> FEATURE:
<223> OTHER INFORMATION: Fully synthetic sequence

<400> SEQUENCE: 27

```
ctcggaaggc agaaactggt gatgaggagg gtacctgaaa acagagtcag ttttgtttgg        60
ttaattatta gtacgctgca atgacgatca ggtttattag tgatcagtga gcaccagcag       120
catgtgtgtg tgtgtgtttg cgtttcttga atatatataa ttacgatcga ccagggtatt       180 atcccgatt tgcagagtgg gttcacagtc cattgcaacc gattgagcag ttgttggatg        240
cacatgatag gtggcgccgt catgctccac catggtgctg ccgggagctg gccaggctgc       300
atgctgcagg gttctgtagt tgctacaacc ttcagcttca agctgtagaa tcggataaca       360
tataagccat ttattcagct ctaatgtata tagcttccat tccattatag ggaagagata       420
aggaccttgt gtttgagttg cctgttcatt tctcccaggt g                           461
```

<210> SEQ ID NO 28
<211> LENGTH: 170
<212> TYPE: DNA
<213> ORGANISM: Artificial sequence
<220> FEATURE:
<223> OTHER INFORMATION: Fully synthetic sequence

<400> SEQUENCE: 28

```
caagatgcta acaagaaact aagaatgaag atagaagaaa ctagtgaaaa aaatgtgctg        60
cgcactgtct agccaggcat attgggtgta gtggcatcta gtgggacatg gtgcatgaag       120
ccaagccaag agacaccgtt caacttgctc ttgatccttc gcagcatata                  170
```

<210> SEQ ID NO 29
<211> LENGTH: 172
<212> TYPE: DNA
<213> ORGANISM: Artificial sequence
<220> FEATURE:
<223> OTHER INFORMATION: Fully synthetic sequence

<400> SEQUENCE: 29

```
gcccagcgga agcaagtgca atggggccaa acccaacagc agaccagttc gtcttcctcg        60
tgcttcgtga taagggaagc tgccccaaca acaaatatca gcattttttcc tgtggcagca      120 ggcgggaggt tggtggaagg tgcagcagcg cagccacagg ctcgcgttgg ac                172
```

<210> SEQ ID NO 30
<211> LENGTH: 314
<212> TYPE: DNA
<213> ORGANISM: Artificial sequence
<220> FEATURE:
<223> OTHER INFORMATION: Fully synthetic sequence

<400> SEQUENCE: 30

```
cttaggagca gtagatggct caatgttatt ttgttgtggc agtgtgctga gttcaagttg    60
cactggaaca tctctggttt ctactactgc aaagttgaat ggagtcggtg actcccgatt   120
aactccactt ggtccttcag tctcatatat ctgagaacaa ttaatatcat gtcatatgtg   180
tggttaggca gttacttagt ggtatttttg ttcaattcat cagctacctt tttatgtaac   240
tcatcatttt cttggcgaat caggttgatc ttattgtaca agtctgtatt ttcttggtga   300
aataaacttg cctt                                                    314
```

<210> SEQ ID NO 31
<211> LENGTH: 25
<212> TYPE: DNA
<213> ORGANISM: Artificial sequence
<220> FEATURE:
<223> OTHER INFORMATION: Fully synthetic sequence
<400> SEQUENCE: 31

```
ccatgggatc aaccattgag aggta                                         25
```

<210> SEQ ID NO 32
<211> LENGTH: 25
<212> TYPE: DNA
<213> ORGANISM: Artificial sequence
<220> FEATURE:
<223> OTHER INFORMATION: Fully synthetic sequence
<400> SEQUENCE: 32

```
gaattctccg agatgaagaa ttttc                                         25
```

<210> SEQ ID NO 33
<211> LENGTH: 24
<212> TYPE: DNA
<213> ORGANISM: Artificial sequence
<220> FEATURE:
<223> OTHER INFORMATION: Fully synthetic sequence
<400> SEQUENCE: 33

```
agatctgatc aaccattgag aggt                                          24
```

<210> SEQ ID NO 34
<211> LENGTH: 25
<212> TYPE: DNA
<213> ORGANISM: Artificial sequence
<220> FEATURE:
<223> OTHER INFORMATION: Fully synthetic sequence
<400> SEQUENCE: 34

```
agatcttccg agatgaagaa ttttc                                         25
```

<210> SEQ ID NO 35
<211> LENGTH: 19
<212> TYPE: DNA
<213> ORGANISM: Artificial sequence
<220> FEATURE:
<223> OTHER INFORMATION: Fully synthetic sequence
<400> SEQUENCE: 35

```
gaattctccg agttggagg                                                19
```

<210> SEQ ID NO 36
<211> LENGTH: 20
<212> TYPE: DNA
<213> ORGANISM: Artificial sequence
<220> FEATURE:
<223> OTHER INFORMATION: Fully synthetic sequence

<400> SEQUENCE: 36
ccatgggtgt gaagtccacc                                                  20

<210> SEQ ID NO 37
<211> LENGTH: 19
<212> TYPE: DNA
<213> ORGANISM: Artificial sequence
<220> FEATURE:
<223> OTHER INFORMATION: Fully synthetic sequence

<400> SEQUENCE: 37
agatcttccg agttggagg                                                   19

<210> SEQ ID NO 38
<211> LENGTH: 20
<212> TYPE: DNA
<213> ORGANISM: Artificial sequence
<220> FEATURE:
<223> OTHER INFORMATION: Fully synthetic sequence

<400> SEQUENCE: 38
agatctgtgt gaagtccacc                                                  20

<210> SEQ ID NO 39
<211> LENGTH: 19
<212> TYPE: DNA
<213> ORGANISM: Artificial sequence
<220> FEATURE:
<223> OTHER INFORMATION: Fully synthetic sequence

<400> SEQUENCE: 39
gaattctctt ccaccttgg                                                   19

<210> SEQ ID NO 40
<211> LENGTH: 20
<212> TYPE: DNA
<213> ORGANISM: Artificial sequence
<220> FEATURE:
<223> OTHER INFORMATION: Fully synthetic sequence

<400> SEQUENCE: 40
ccatgggcgt gaagggcacc                                                  20

<210> SEQ ID NO 41
<211> LENGTH: 19
<212> TYPE: DNA
<213> ORGANISM: Artificial sequence
<220> FEATURE:
<223> OTHER INFORMATION: Fully synthetic sequence

<400> SEQUENCE: 41
agatcttctt ccaccttgg                                                   19

<210> SEQ ID NO 42
<211> LENGTH: 20
<212> TYPE: DNA
<213> ORGANISM: Artificial sequence
<220> FEATURE:
<223> OTHER INFORMATION: Fully synthetic sequence

<400> SEQUENCE: 42
agatctgcgt gaagggcacc                                                  20

<210> SEQ ID NO 43

<211> LENGTH: 23
<212> TYPE: DNA
<213> ORGANISM: Artificial sequence
<220> FEATURE:
<223> OTHER INFORMATION: Fully synthetic sequence

<400> SEQUENCE: 43
gaattcagtt ggtagccgag gtt                                      23

<210> SEQ ID NO 44
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 44
ccatggattg aggagggaga gca                                      23

<210> SEQ ID NO 45
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 45
agatctagtt ggtagccgag gtt                                      23

<210> SEQ ID NO 46
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 46
agatctattg aggagggaga gca                                      23

<210> SEQ ID NO 47
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 47
gaattctgga gggttgtagg ttg                                      23

<210> SEQ ID NO 48
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 48
ccatgggcaa gatcgctgag agt                                      23

<210> SEQ ID NO 49
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 49
agatcttgga gggttgtagg ttg                                               23

<210> SEQ ID NO 50
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 50
agatctgcaa gatcgctgag agt                                               23

<210> SEQ ID NO 51
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 51
gaattcctcg gaaggcagaa act                                               23

<210> SEQ ID NO 52
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 52
ccatggcacc tgggagaaat gaa                                               23

<210> SEQ ID NO 53
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 53
agatctctcg gaaggcagaa act                                               23

<210> SEQ ID NO 54
<211> LENGTH: 23
<212> TYPE: DNA
<213> ORGANISM: Artificial sequence
<220> FEATURE:
<223> OTHER INFORMATION: Fully synthetic sequence

<400> SEQUENCE: 54
agatctcacc tgggagaaat gaa                                               23

<210> SEQ ID NO 55
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 55
gaattcctat atgcagcgaa ggat                                              24

<210> SEQ ID NO 56
<211> LENGTH: 24
<212> TYPE: DNA

```
<213> ORGANISM: Artificial sequence
<220> FEATURE:
<223> OTHER INFORMATION: Fully synthetic sequence

<400> SEQUENCE: 56
ccatggcaag atgctaacaa agat                                          24

<210> SEQ ID NO 57
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 57
agatctctat atgcagcgaa ggat                                          24

<210> SEQ ID NO 58
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 58
agatctcaag atgctaacaa agat                                          24

<210> SEQ ID NO 59
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 59
gaattcgtcc aacgcgagcc tgtg                                          24

<210> SEQ ID NO 60
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 60
ccatgggccc agcggaagca agtg                                          24

<210> SEQ ID NO 61
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 61
agatctgtcc aacgcgagcc tgtg                                          24

<210> SEQ ID NO 62
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 62
agatctgccc agcggaagca agtg                                          24
```

<210> SEQ ID NO 63
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 63
gaattcctta ggagcagtag atgg                                              24

<210> SEQ ID NO 64
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 64
ccatggaagg caagtttatt tcac                                              24

<210> SEQ ID NO 65
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 65
agatctctta ggagcagtag atgg                                              24

<210> SEQ ID NO 66
<211> LENGTH: 24
<212> TYPE: DNA
<213> ORGANISM: Artificial sequence
<220> FEATURE:
<223> OTHER INFORMATION: Fully synthetic sequence

<400> SEQUENCE: 66
agatctaagg caagtttatt tcac                                              24

<210> SEQ ID NO 67
<211> LENGTH: 693
<212> TYPE: DNA
<213> ORGANISM: Arabidopsis thaliana

<400> SEQUENCE: 67
atgggaagag gaaagataga aataaagagg atagagaact caacaaatcg acaagtgacg        60
ttttgcaaaa gaagaaatgg acttctgaag aaagcctatg agctttcggt cctttgcgat       120
gcagaagttg cgctcattgt tttctccact cgtggccgtc tctatgaata cgccaataac       180
aacataagat caaccattga gaggtacaag aaagcttgtt ctgatagcac caacactagc       240
actgtccaag aaatcaatgc cgcgtactac caacaagaat ctgctaagct gagacaacag       300
atccaaacga ttcaaaactc caacaggaat ctgatgggag actctttgag ttccttaagt       360
gtcaaggaac taaacaagt tgagaatcgc cttgagaaag ctatctctag gatcaggtcc       420
aagaagcatg agttgctttt agttgaaatc gaaacgcgc agaaaaggga gattgagctt       480
gacaatgaga acatctatct aagaactaag gtagcagaag tggagaggta tcaacaacac       540
catcatcaaa tggttagtgg ttcagagatt aatgcaattg aagctttagc ctcacgcaat       600
tactttgctc atagcattat gactgctggt tctggatctg gtaatggagg ttcttactct       660

```
gatcccgaca agaaaattct tcatcacgga tag                                  693
```

<210> SEQ ID NO 68
<211> LENGTH: 939
<212> TYPE: DNA
<213> ORGANISM: Glycine max

<400> SEQUENCE: 68

```
gatagcgcag tttcatttct ttggattaga aattttcccc aaagctgatc gagaagccag     60
ccaggccaga gttgaagaag aatgggaagg gggaagatcg aaatcaaaag gattgagaac    120
acaacaaatc ggcaagtgac cttctgcaag agaagaaatg gcttctgaa gaaagcttat    180
gagctgtcag tgctgtgtga tgcagaagtt gccctcatcg tcttctccag ccgtggccgt    240
ctctatgagt attccaacaa caacataaga tcaacaatag agaggtacaa aaaggcatgt    300
tctgatcact caagcgcgag cactaccaca gaaatcaatg ctcagtatta tcaacaagaa    360
tctgcaaagc tgcgacagca aatacagatg ctgcaaaatt ctaacaggca cctgatgggt    420
gatgccttaa gcacactgac tgtgaaggaa cttaagcagt tggagaatag acttgaaaga    480
ggaatcacta gaatcagatc taagaaacat gagatgctac tggctgaaat tgaatacttc    540
cagaaaaggg agattgaact ggaaaatgaa aatctttgcc tccgaactaa gataactgac    600
gtggagagga ttcagcaagt aaacatggtt tctgggccag aactgaatgc cattcaggca    660
ttagcttccc gtagcttctt caatccaaat atgttggaag gtggaactgt ttaccctcac    720
tcagataaga agattcttca tcttgggtga tcaataatat atgatcttgg ctagcctatg    780
gcatgtctat ccaattagcc ggtggctaaa tgcattatta ttactactct tttggttgct    840
cattaactag accatgtgat ctatatacta cttatggatt atggatactt atgtatgatg    900
attgtatgat atcataacaa tcagttagaa ataataatt                            939
```

<210> SEQ ID NO 69
<211> LENGTH: 1133
<212> TYPE: DNA
<213> ORGANISM: Zea mays

<400> SEQUENCE: 69

```
gccctgatca catcatcctg cttgtctctc cccaacctag ctccatctct ctttcatcta     60
ctcttccatc gatcgatcca tcgtactgcg tgaggatggg gaggggaaag attgagatca    120
agaggatcga gaacaccacc agccgccagg tgaccttctg caagcgcagg aatgggctgc    180
tgaagaaggc ctacgagctc tccatcctct gcgacgctga tcgctttg atcgtcttct    240
ctacccgagg ccgcctatat gaatattcca gtaacagcgt aaggtcgacg atcgagaggt    300
acaagaaagc ctctgccagc acttcaggaa cagctccagt gacagatgtc aactctcttc    360
aatactttca gcaagaagcg gcaaaactgc gccagcagat acaaaccttg cagaattcaa    420
acaggcacct gatgggtgaa tctactggca atatgactgc aaaggagcta aagggccttg    480
aaagcaggct tgaaagaggc attgggagga tccggtccaa aaagcatgag ctgctgctcg    540
cggagatcga atatatgcag aagagggaat cagatctgca caatgaaaac atgttcctgc    600
gggccaaggt tgcggaggct gagcgagctc tggagcagga ggcggcagaa gaccagacga    660
tgatggtgcc ggcggcggtc cgcggggcta cgacggagct gaaagcgctg ccggcgtcgt    720
tcgacgcgag tggctactac cagtaccagc agcatcagca tgtggtggcc gccgcctccg    780
ctgcctcctc gtcgcagtac gcggagcagc cccagggcca gcaggagtac caccaccaga    840
ctgccctcca cctcggctac cacgtcaaga tcgactccgc cgccgacaaa ggcttcctct    900
```

```
aggcgctcgc gcgcatgcat gcgtgaagcg tctcatctca taatctgacg tacggacgat     960
gggtgccgga cagctaacgt aaggcacgtt gtcatcgcct gaccatggag tggagtggtt    1020
gttgctatat gtgcttctat atagagagag aaaataaggt gtcgatccgc gagtacctat    1080
atacgcaagc tgtatcaaac aatattgtca tgagatatat agattaacta tat           1133
```

<210> SEQ ID NO 70
<211> LENGTH: 1361
<212> TYPE: DNA
<213> ORGANISM: Oryza sativa

<400> SEQUENCE: 70

```
tctttaatac ctctcctcct cctgttgctg cttctgcctc tctcacatct tctttctttc      60
cttctctgga tctcttccat cttcagaaga gagagcacta gttagcatac ccatccatga     120
tgaacatgat gaccgatctg agctgcgggc catcgtcgat gacggagctg accgcggcag     180
gcgccggctg ggtcaggatc gtcggcggcg gtggcggcgg ggagcagcga aagatgggg     240 agggggaaga tcgagataaa gcggatcgag aacacgacga accggcaggt gaccttctgc     300
aagcgccgca atggcctcct gaagaaggcg tacgagctgt ccgtcctctg cgacgccgag     360
gttgccctca tcgtcttctc cagccgcggg cgcctctacg agtacgccaa caacagtgtg     420
aaatccaccg ttgagaggta caagaaggca acagtgaca cctccaactc tggcacagtt     480
gcagaagtca atgcccagca ctaccagcag gagtcctcca aactgcgcca acaaatcagt     540
agcttacaga acgcaaacag taggaccata gtgggggatt ctatcaacac catgagcctc     600 agggaccta aacaggtaga gaacaggctg gagaaaggca tagctaagat aagggctaga     660
aagaatgagc tgttatatgc tgaagttgag tacatgcaga aaagggaagt tgagctgcag     720
aatgacaaca tgtacctgag gagcaaggtt gttgagaatg agaggggaca gcagccactg     780
aacatgatgg gggcagcatc aacaagtgaa tacgatcata tggttaataa cccatatgat     840
tccaggaact ttcttcaagt gaacatcatg cagcagcctc agcattacgc ccatcagctg     900
cagccaacta cccttcaact cgggcagcag ccggccttca attagtttg gtgtagacac     960 cgtacgtaca cacatgaaat ctgaaggcgt cgatacccgc ggctacgtaa cagcgtgatc    1020
aacctgaaga atcgatgca gtaattctat gtgttcgtca gatcatcata accagtattg    1080
tcattaggcg ttgtgaaaaa aaaatgtgtc agcatgcatt gcaagctagc gtttgtggct    1140
gctcatcagc tgcatgcgta attgcgtacg tgcacaaatt aaacagacct tgctaccatt    1200
gtgccatatt gtgtgtgttg tatgatatat atatatatat atatatatat atatatatat    1260
atatatatat aaacagcacg tttgtgctct gattcgtgta actgatcagc agatcaaact    1320
ctaccactgc cgatatatat gtgaggacca tggattgatg c                        1361
```

<210> SEQ ID NO 71
<211> LENGTH: 25
<212> TYPE: DNA
<213> ORGANISM: Artificial sequence
<220> FEATURE:
<223> OTHER INFORMATION: Fully synthetic sequence

<400> SEQUENCE: 71

```
acgcgtcgac atggattctt ccaat                                           25
```

<210> SEQ ID NO 72
<211> LENGTH: 26
<212> TYPE: DNA

<213> ORGANISM: Artificial sequence
<220> FEATURE:
<223> OTHER INFORMATION: Fully synthetic sequence

<400> SEQUENCE: 72

| | |
|---|---|
| ccgctcgagc cttcatttta aacatc | 26 |

<210> SEQ ID NO 73
<211> LENGTH: 2569
<212> TYPE: DNA
<213> ORGANISM: Arabidopsis thaliana

<400> SEQUENCE: 73

| | |
|---|---|
| atggattctt ccaattacaa aaattatgcc tcaaatatgt tccttacata tggctgaaaa | 60 |
| tggttgtaaa aaaaagttaa cgaatgtttt tttttttta cttttccctt attttgtttc | 120 |
| tttttaccat tttggagagg agattaatta ttataatcat caaaaaactg aaaataacga | 180 |
| gaaagtatta caagacaata atgtggtaaa atgttgactg tctcaaaata caaaatgtcg | 240 |
| cttaagaaag gagctatata ttttctactg ctcgcaatct tagaattaat ttttaaaaat | 300 |
| aatttcaaaa ttttagtaat aatattatat gttatgaact aattaaaacct taatgtactg | 360 |
| ccaatcatat taagaatgaa ataaatattt cttattgttc tttgtcaaaa aaaagctatt | 420 |
| tcttattgtt ttatatattt tagtgaaact atataaatgt tttttttgaa gttttctttg | 480 |
| taaccgggaa attaaaaaaa ccgtgattgc aattgcaaaa tttgagatta taaattcata | 540 |
| atgataagcc taatcactga aacaccatgg ttttattatt tcacttttt ttaccatgca | 600 |
| attaattttt ttacctcatt atatatccag taatgaaagt tagaacaatt aatataattg | 660 |
| catcttcgga gatcccaaat cttggtcttg ccgtgaactt ggccaaagta tgaaatgatg | 720 |
| gcgcatgtag cttagctaga gtctccattt ctctacaaaa ataagaatta aacaacaaat | 780 |
| actcacactt aagagttttg taggaatctt aaatactact aatactttat atgtgcgatt | 840 |
| tagcttaaaa gaaaggttaa aataactttt tttggttgct cgttattttt tcctttcatt | 900 |
| cttaaaattt tttctattca aaattaagat tcaggtttt ttttataata tagcaaatgc | 960 |
| attggcaagt ggcaaccgca accgcagcaa tcgcaatctc actttggaca ttggaaggtg | 1020 |
| agcaaagaaa gaaacgtcta caaatagaca tattgagtga aagcttagg gttttgaag | 1080 |
| agaaagaat ttgggtttgt ttttgggatt ctcaaaaaac tcaaatraaa ctttcctcat | 1140 |
| tttttttttc tttctttgt tttgttttct ttataaagga gaaagaaaga gaaagagagt | 1200 |
| ttccgaaagc tgaattgagt tgggtgaagc aaattctcag gtctgtctgt catgtcttta | 1260 |
| cttcttcttc tcataaagga aaacacttct tgatctcatc aagttcccat ctttgtacac | 1320 |
| atctcttcat tcaaaaactc tacatttata tctctatata tgcagattcc aagcttgtaa | 1380 |
| taattcttgt catcatgggt tttttttcttg ccttgtctct ccagaaaact taattttcac | 1440 |
| aattatgaat tattttcctt attttttgtta ctttcttctg tttgatgctc tttccccatg | 1500 |
| aaagaaagaa agagaaagaa agatcacaag ggttttattt ggtcaccaga ttaagaatta | 1560 |
| ggttatcttt ttttttttt tagttttctca catgtagatc tctgctagat tctctttcct | 1620 |
| ttcttgtcag ctaaagtgga gttttttgagt ctgaaaatct tccaaatctg ttgtatttct | 1680 |
| tcttcctctc ttctcgaaac taagcatggt tttgtctctc tcttctttct gtgtaataat | 1740 |
| gtttcttgtg tttcccttat gtactataac ttcagtttca tgtgcatcag tgccttcttc | 1800 |
| ttcttcctct tcaatatcaa tttgattgt tttctctctc catatttcca attttttttc | 1860 |
| tttatcaaaa gttatttaat cttttgctct gtgaaaacaa actaaagaat gcgtaagaat | 1920 |

```
gcctacatac atcagatcaa tgaatttgta agacatatta catatgtcta aagtatttac    1980
atcttccaga tctaagatca ttacgtatat gttgttttcc attttgaccc cgtgaagcct    2040
tatagacatt tattgaagag ggagggagat agtacacggg atgggtcaaa attatttgta    2100
tctgggtacc aaaaaaccat gtaatatatt gtcagatttt atctccctgg ctttaaaaaa    2160
acaattcctg atgagttagt taagtatata gataatacat atagaaccta tctagctaac    2220
aagaattaca tgtaatatat attaataatc ttgtaatttg aataaattct taaactctag    2280
ttccaacaac atcagattca gttgattctt gtctgtcctt gagatcaatc aacaacatcc    2340
ttaattgaat ttcccgagaa agttggatac agaaagaaaa cttttttttt aatatatata    2400
acaaaagtcg agtttggtat gtattaatta agtacattaa ttcaaaccct agctttagtt    2460 tttttttttat cttcttgcag tctgccacta gtttgtgtgt taatatttat cttaccaata  2520
ctgccgaaat tgagcaattc taagtgttgt ttgatgttta aaatgaagg               2569
```